(12) United States Patent
Wang et al.

(10) Patent No.: US 7,081,192 B1
(45) Date of Patent: Jul. 25, 2006

(54) METHODS FOR MANIPULATING MOIETIES IN MICROFLUIDIC SYSTEMS

(75) Inventors: Xiaobo Wang, San Diego, CA (US); Lei Wu, San Diego, CA (US); Jing Cheng, Beijing (CN); Weiping Yang, San Diego, CA (US); Junquan Xu, Fujian (CN)

(73) Assignee: Aviva Biosciences Corporation, San Diego, CA (US)

( * ) Notice: Subject to any disclaimer, the term of this patent is extended or adjusted under 35 U.S.C. 154(b) by 648 days.

(21) Appl. No.: 09/636,104

(22) Filed: Aug. 10, 2000

(30) Foreign Application Priority Data

Aug. 8, 2000 (CN) .............................. 00 1 22631

(51) Int. Cl.
*G01N 27/447* (2006.01)
*G01N 33/48* (2006.01)
*C12Q 1/00* (2006.01)

(52) U.S. Cl. .......................... 204/547; 435/4; 422/68.1
(58) Field of Classification Search ................ 204/547, 204/643; 422/100, 50, 55, 68.1, 82.05, 101; 210/748; 435/4
See application file for complete search history.

(56) References Cited

U.S. PATENT DOCUMENTS

| | | | | |
|---|---|---|---|---|
| 4,743,361 A * | 5/1988 | Schram | .......................... | 209/1 |
| 4,894,443 A | 1/1990 | Greenfield et al. | .......... | 530/388 |
| 5,302,898 A | 4/1994 | Pethig et al. | ................ | 324/316 |
| 5,612,474 A | 3/1997 | Patel | ........................ | 536/27.14 |
| 5,620,857 A * | 4/1997 | Weetall et al. | ................. | 435/7.1 |
| 5,630,924 A * | 5/1997 | Fuchs et al. | ................. | 204/601 |
| 5,653,859 A * | 8/1997 | Parton et al. | ................. | 204/450 |
| 5,683,859 A | 11/1997 | Nothnagle et al. | ........... | 430/488 |
| 5,705,813 A * | 1/1998 | Apffel et al. | ................ | 250/288 |
| 5,795,457 A | 8/1998 | Pethig et al. | ................ | 204/547 |
| 5,800,690 A | 9/1998 | Chow et al. | ................. | 204/451 |
| 5,814,200 A | 9/1998 | Pethig et al. | ................ | 204/547 |
| 5,944,971 A | 8/1999 | Foote | .......................... | 204/456 |
| 5,948,231 A * | 9/1999 | Fuchs et al. | ................. | 204/601 |
| 5,993,631 A | 11/1999 | Parton et al. | ................ | 204/547 |
| 6,029,518 A | 2/2000 | Oeftering | .................... | 73/570.5 |
| 6,071,394 A | 6/2000 | Cheng et al. | ................ | 204/547 |
| 6,159,749 A * | 12/2000 | Liu | ............................. | 436/527 |
| 6,221,677 B1 * | 4/2001 | Wu et al. | .................... | 436/518 |

(Continued)

FOREIGN PATENT DOCUMENTS

WO    WO 93/16383    8/1993

(Continued)

OTHER PUBLICATIONS

Michael P. Hughes and Hywel Morgan, "Dielectrophoretic Characterization and Separation of Antibody-Coated Submicrometer Latex Spheres" Analytical Chemistry, vol. 71, No. 16, pp. 3441-3445, Aug. 15, 1999.*

(Continued)

*Primary Examiner*—Alex Noguerola
(74) *Attorney, Agent, or Firm*—Morrison & Foerster LLP

(57) ABSTRACT

This invention relates generally to the field of moiety or molecule manipulation in a chip format. In particular, the invention provides a method for manipulating a moiety in a microfluidic application, which method comprises: a) coupling a moiety to be manipulated onto surface of a binding partner of said moiety to form a moiety-binding partner complex; and b) manipulating said moiety-binding partner complex with a physical force in a chip format, wherein said manipulation is effected through a combination of a structure that is external to said chip and a structure that is built-in in said chip, thereby said moiety is manipulated.

46 Claims, 21 Drawing Sheets

U.S. PATENT DOCUMENTS

| | | | |
|---|---|---|---|
| 6,245,207 B1 * | 6/2001 | Yasuda et al. | 204/600 |
| 6,296,810 B1 * | 10/2001 | Ulmer | 422/82.07 |
| 6,355,491 B1 * | 3/2002 | Zhou et al. | 436/518 |
| 6,544,734 B1 * | 4/2003 | Briscoe et al. | 435/6 |

FOREIGN PATENT DOCUMENTS

| | | |
|---|---|---|
| WO | WO 96/07917 | 3/1996 |
| WO | WO-96/09379 A1 * | 3/1996 |
| WO | WO 97/27933 | 8/1997 |
| WO | WO 97/34689 | 9/1997 |
| WO | WO 98/04355 | 2/1998 |
| WO | WO 98/10869 | 3/1998 |
| WO | WO 99/12016 | 3/1999 |
| WO | WO 99/38612 | 8/1999 |
| WO | WO 00/32744 | 6/2000 |
| WO | WO 00/37163 | 6/2000 |
| WO | WO 00/47322 | 8/2000 |
| WO | WO 01/05511 | 1/2001 |
| WO | WO 01/05512 | 1/2001 |
| WO | WO 01/05513 | 1/2001 |
| WO | WO 01/05514 | 1/2001 |

OTHER PUBLICATIONS

CAPLUS abstract of Drake et al. ("Silyl and germyl derivatives of trifluoroacetic and trichloroacetic acid," Inorganic Chemistry (1977), !6(7), 1682-6).*
CAPLUS abstract of Ma et al. ("Synthesis of uniform microspheres with higher content of 2-hydroxylmethacrylate by employing SPH (Shirasu porous glass) emulsification technique followed by swelling process of droplets," Journal of Applied Polymer Science (1997) 66(7) 1325-1341).*
CAPLUS abstract of Chen et al. (CN 1145410 A).*
CAPLUS abstract Yang et al. ("New, porous microsphere of bisphenol A epoxy resin," Gaofenzi Xuebao (1997), (1), 119-120).*
CAPLUS abstract of Yuan et al. ("Protein-loaded poly (ε-caprolactone) microparticles. I. Optimization of the preparation by (water-in-oil)-in water emulsion solvent evaporation," journal of Encapsulation 91999), 16(5), 587-599).*
CAPLUS abstract of Rojas et al. ("A polysorbate-based nonionic surfactant can modulate loading and release of (β-lactoglobulin entrapped in multiphase poly(DL-lactide-co-glycolide) microspheres," Pharmaceutical Research (1999), 16(2), 255-260).*
CAPLUS abstract Hernandez et al. ("Influence of shaking and surfactants on the release of BSA from PLGA microspheres," European journal of Drug Metabolism and Pharmacokinetics (1998), 23(2), 92-96).*
CAPLUS abstract Shen ("Preparation, characterization and application of magnetic microsphere," Huaxue tongbao (1997), (9), 55-57).*
Ahn C. et al. *J of Microelectromechanical Systems* 5:151-157 (1996).
Ashkin A. *Biophys J* 61:569-582 (1992).
Batra et al., *Molecular Immunol.*, 30:379-386 ((1993).
Becker et al. *J Phys D: Appl Phys* 27:2659-2662 (1994).
Becker et al. *Proc Natl Acad Sci* 92:860-864 (1995).
Blankenstein et al., *Biosensors & Bioelectronics* 13(3-4):427-438 (1998).
Block S. *Nature* 360:493-496 (1992).
Cheng et al., *Nature Biotechnology* 16:541-546 (1998).
Coakley et al. *Bioseparation* 4:73-83 (1994).
Cumber et al., *Bioconj. Chem.*, 3:397-401 (1992).
Fan et al., *Anal. Chem.*, 71(21):4851-9 (1999).

Fattom et al., *Infection & Immun.*, 60:584-589 (1992).
Fiedler et al. *Microsystem Technologies* 2:1-7 (1995).
Fiedler et al. *Anal Chem* 70:1909-1915 (1998).
Fuhr et al. *Biochim Biophys Acta* 1108:215-233 (1992).
Fuhr et al. *Sensors and Actuators A* 41:230-239 (1994).
Fuhr et al. *Sensors and Materials* 7:131-146 (1995A).
Fuhr G. et al. In *Cellular Engineering*. Autumn: pp. 47-57, 1995.
Gascoyne et al. *IEEE Transaction on Industry Applications* 33(3):670-678 (1997).
Goldmacher et al. *Bioconj Chem* 3:104-107 (1992).
Green and Morgan. *J Phys D: Appl Phys* 30:L41-L44 (1997).
Hagedorn et al., *Electrophoresis* 13:49-54 (1992).
Hagedorn et al., *Journal of Electrostatics* 33:159-185 (1994).
Hawkes et al. *Microbios* 73:81-86 (1993).
Hazum et al., in *Pept., Proc. Eur. Pept. Symp.*, 16th, Brunfeldt, K (Ed), pp. 105-110 (1981).
Huang and Pethig. *Meas Sci Technol* 2:1142-1146 (1991).
Huang et al. *J Phys D: Appl Phys* 26:1528-1535 (1993).
Huang et al. *Biophys J* 73:1118-1129 (1997).
Hughes et al. *Biochem Biophys Acta* 1425:119-126 (1998).
Huston et al., *Proc. Natl. Acad. Sci. U.S.A.*, 85:5879-5883 (1988).
Kilburn et al. *Biotechnol Bioeng* 34:559-562 (1989).
Kronick P. In Methods of Cell Preparation, vol. 3, edited by N.Catsimpoolas, 1980, pp. 115-139.
Ladurner et al., *J. Mol. Biol.*, 273:330-337 (1997).
Lichtenberg, et al., in Micro Total Analysis Systems 2000 edited by A. van den Berg et al., pp. 307-310.
Morgan et al. *J Micromech Microeng* 7:65-70 (1997).
Morgan et al. *Biophys J* 77:516-525 (1999).
Muller et al. *Biosensors and Bioelectronics* 14:247-256 (1999).
Newton et al., *Biochemistry*, 35:545-553 (1996).
Pethig e al. *J Phys D: Appl Phys* 25:881-888 (1992).
Safarik I. and Safarikova M. *J Chromatogr* 722(b):33-53 (1999).
Schnelle et al. *Biochim Biophys Acta* 1157:127-140 (1993).
Schram, C.J. In *Advances in Sonochemistry*; Mason, T.J., Ed.; JAI Press Ltd., London, 1991; vol. 2: pp. 293-322.
Senter et al., *Photochem. Photobiol*, 42:231-237 (1985).
Stephens et al. *Bone Narrow Transplantation* 18:777-782 (1996).
Wang et al. *J Phys D: Appl Phys* 26:1278-1285 (1993).
Wang et al. *Biochim Biophys Acta* 1243:185-194 (1995).
Wang et al. *IEEE Transaction on Industry Applications* 33(3):660-669 (1997).
Wang et al. *Biophys J* 72:1887-1899 (1997).
Wang et al. *Biophys J* 74:2689-2701 (1998).
Washizu et al. *IEEE Transaction on Industry Applications* 26:352-358 (1990).
Washizu et al. *IEEE Transaction on Industry Applications* 30:835-843 (1994).
Welhoner et al. *J Biol Chem* 266:4309-4314 (1991).
Whitlow, et al., *Protein Engineering*, 6:989-995 (1993).
Whitworth et al. *J Accost Soc Am* 91:79-85 (1992).
Wright et al. *IEEE J of Quantum Electronics* 26:2148-2157 (1990).
Yang et al. *Anal Chem* 71(5):911-918 (1999).
Yasuda K. et al. *Jpn J Appl Physics* 35:3295-3299 (1996).
Yen et al., *Makromol. Chem*, 190:69-82 ((1989).
Yoshioka K. and Kawashima Y. *Acustica* 5:167-174 (1955).

* cited by examiner

120

130

METHODS FOR MANIPULATING MOIETIES IN MICROFLUIDIC SYSTEMS

RELATED APPLICATION

This application is related to a Chinese national patent application, 00122631.2 filed Aug. 8, 2000, entitled "METHODS FOR MANIPULATING MOIETIES IN MICROFLUIDIC SYSTEMS." The disclosure of the above Chinese national patent application is incorporated by reference in its entirety.

TECHNICAL FIELD

This invention relates generally to the field of moiety or molecule manipulation in a chip format. In particular, the invention provides a method for manipulating a moiety in a microfluidic application, which method comprises: a) coupling a moiety to be manipulated onto surface of a binding partner of said moiety to form a binding partner-moiety complex; and b) manipulating said binding partner-moiety complex with a physical force in a chip format, wherein said manipulation is effected through a combination of a structure that is external to said chip and a structure that is built-in in said chip, thereby said moiety is manipulated.

BACKGROUND ART

Intensive research efforts in developing microfluidic systems have been pursued by academic and industrial institutions over recent years. These microfluidic devices and apparatus are developed for performing various fluidics-related functions, processes and activities. Almost all microfluidic devices involve manipulating, handling, and processing molecules and particles. However, up to now, there is not a general method for manipulating molecules in microfluidic devices. Some examples of physical methods for manipulating molecules used in biochips include electric field based electrophoresis, optical radiation force related optical tweezers and others. All these methods have many limitations. Electrophoresis utilizes direct current (DC) electrical field. Generating sufficient DC field in aqueous solutions without causing undesired effects, e.g., surface electrochemistry, gas bubble generation, is very difficult. Electric field can only guide molecules either with or against with the field direction. There won't be any force induced if the molecule charges are small. Most importantly, the DC electrical field cannot be readily structured to generate manipulation forces in a versatile way. Also, electrode polarization determines that over 80% of the applied DC voltage is dropped across the electrode-solution double layer and there is only a very small percent of the applied voltage that is actually across the bulk solution. Optical radiation force can operate on large molecules, e.g., DNA molecules, but there are certain difficulties in generating 3-D, flexible, optical manipulation forces.

Despite the existence of a number of physical forces applicable to molecule manipulation, several key difficulties exist. First, many physical forces are proportional to the volume of the particles that are manipulated. Direct manipulation of many types of molecules with these forces requires extremely high field strength because of the relative small dimensions of molecules, and effective manipulation of molecules is almost impossible. High field strengths tend to induce undesired fluid motion for manipulation forces such as dielectrophoresis or traveling-wave-dielectrophoresis. Secondly, certain types of physical forces can be generated on molecules, but the 3-D distributions of these physical forces cannot be readily structured for flexible, versatile handling and manipulation of molecules. Thirdly, there is still no general method for manipulating and handling molecules in microfluidic systems and devices.

Microparticles have been used for manipulating molecules in biological fields. One example is the use of magnetic microparticles to harvest and isolate nucleic acid molecules, e.g., mRNAs or DNAs, from a solution suspension. Typically, the separation process takes place in an Eppendorf tube in which paramagnetic particles are mixed with solutions containing target nucleic acid molecules. The modification of the paramagnetic particles' surface molecules allows the binding of the target molecules to paramagnetic particles' surfaces. After incubation of the magnetic particles with nucleic acid molecules in the Eppendorf tube, the nucleic acid molecules are bound to the paramagnetic particles. An external magnetic field is then applied to the Eppendorf tube from one side by using a permanent magnet. All the magnetic particles are collected onto the regions of the tube wall, which are closest to the magnet. Micropipette is then used to pipette out the solutions while the magnetic particles being retained on the tube wall by the magnetic field. This step leaves all the magnetic particles in the tube. New buffer solutions are then introduced into the Eppendorf tube, which is taken away from the magnet. After resuspending magnetic particles into the solution, the new buffer may allow the bound nucleic acid molecules to de-couple from the magnetic particle surfaces. Then a magnet may be applied to attract and trap magnetic particles on the tube wall. Micropipette is then used to pipette solutions out of the tube and to collect the nucleic acid molecules. Recently, similar methods have been used on a chip using paramagnetic beads and an externally applied, off-chip permanent magnet (Fan et al., *Anal. Chem.*, 71(21):4851–9 (1999)). This method has certain limitations. Reducing such permanent magnet size and handling a large number of these small permanent magnets automatically for manipulation of particles in a chip format will be a very difficult, if not impossible, challenge. Thus, the method cannot be readily miniaturized and automated. Furthermore, the permanent magnet-based methods are not applicable to many steps in bioanalytical procedures. Thus, the biochip-system integration based this method will be difficult, if not impossible.

U.S. Pat. No. 5,653,859 discloses a method of analysis or separation comprising: treating a plurality of original, particles to form a subplurality of altered particles from at least some of said plurality of original particles, said subplurality of altered particles having travelling wave field migration properties distinct from those of said plurality of original particles; and producing translatory movement of said subplurality of altered particles and/or said plurality of original particles by travelling wave field migration using conditions such that said translatory movement of said subplurality of altered particle differs from said translatory movement of said plurality of original particles under the same conditions. The physical force used in the methods of U.S. Pat. No. 5,653,859 is limited to the force effected via travelling wave field. In addition, to be used in the methods of U.S. Pat. No. 5,653,859, the original particles have to be partially, but not completely, converted into a subplurality of altered particles because the methods are based upon detecting different translatory movement of the altered particles and the original particles.

In summary, the currently available manipulation methods suffer from the following deficiencies: (1) it is difficult to directly apply effective, physical manipulation forces to many types of molecules because of the relative small dimensions of molecules; and (2) some physical forces that can be generated on molecules often have limitations in 3-D structuring of the force distribution and (3) it is difficult to use currently available biochip-based methods for developing fully automated, miniaturized and integrated biochip systems.

The present invention addresses these and other related needs in the art. It is an objective of the present invention to provide a general method for manipulating a variety of moieties including molecules. It is another objective of the present invention to make full use of a number of force mechanisms effectively for manipulating the moieties. It is still another objective of the present invention to provide for standardized on-chip manipulation procedure, leading to simplification and standardization of the design of microchips and the associated systems. It is yet another objective of the present invention to expand and enhance the capabilities of molecule manipulation with the choice of microparticles with special physical properties. It is yet another objective of the present invention to provide a general, effective procedure for on-chip molecule manipulation that allows for fully integration of biochip-based analytical systems and processes.

DISCLOSURE OF THE INVENTION

This invention relates generally to the field of moiety or molecule manipulation in a chip format. In one aspect, the invention is directed to a method for manipulating a moiety in a microfluidic application, which method comprises: a) coupling a moiety to be manipulated onto surface of a binding partner of said moiety to form a binding partner-moiety complex; and b) manipulating said binding partner-moiety complex with a physical force in a chip format, wherein said manipulation is effected through a combination of a structure that is external to said chip and a structure that is built-in in said chip, thereby said moiety is manipulated.

The present invention provides a general method for handling, processing and manipulating a variety of moieties including molecules in a chip format for numerous microfluidic applications. For biomedical applications, moieties such as cells, organelles, macromolecules, small molecules and molecule aggregates may be manipulated for various bioanalytical procedures. Target moiety types may be separated, concentrated, transported, selectively manipulated. Using numerous types of binding partners, multiple target moieties (e.g., certain mRNA and protein molecules from cell lysate) may be isolated and selectively manipulated from a moiety mixture. Molecules or certain moiety types that cannot be manipulated directed by chip-generated physical forces may now be handled and processed through the use of the binding-partner for forming the binding partner-moiety complexes. With the present invention, for example, small protein molecules that can not be effectively manipulated by dielectrophoresis forces because of the small volume may be now handled by on-chip generated dielectrophoresis forces through the procedure of coupling them onto the surfaces of microbeads and manipulating the protein-bead complexes with the built-in electrodes on a chip. Thus, the present invention addresses one critical limitation in current biochip application, i.e., the lack of general method for manipulation of a variety of moieties especially molecules.

The present invention provides a method for handling and manipulating a variety of moieties in a chip format by utilizing a number of force mechanisms. Coupling the moiety onto the binding partners expands the possibility of available force mechanisms for manipulating moieties. For example, cells that can not be directly manipulated by magnetic forces because of the lack of certain magnetic properties may now be processed by on-chip generated magnetic forces through the procedure of coupling them onto the surfaces of magnetic beads and manipulating the magnetic bead-cell complexes with the built-in electromagnetic units on a chip. Thus, the present invention improves significantly the flexibility and easiness for manipulating a variety of moieties in a chip format.

The present invention provides for the standardized on-chip manipulation procedure and allows for simplification and standardization of the design of microchips and the associated systems. The manipulation and processing of target moiety types is an essential requirement involved in almost all bioanalytical processes, procedures and steps. The present invention may be utilized for all these processes and steps, leading to additional advantages of fully integration of biochip-based analytical systems and processes.

Generally, biochip-based applications are divided into sample preparation, bio/chemical reactions and result-detection. Sample preparation refers to the isolation and preparation of certain target moiety (or moieties) from a mixture sample. Bio/chemical reactions refer to the reaction processes involving the prepared moiety (or moieties) for the follow-on detection and quantification. The result-detection refers to the detection and/or quantification steps to analyze the reaction-generated products. An example of these steps is the separation of target cancer cells from body fluid and the isolation of target mRNA molecules from the separated cancer cells, the reverse-transcription of mRNA to cDNA followed by cDNA amplification and detection. The present invention may be used in all these steps. Micorbeads with antibodies on the bead surfaces that are specific for target cancer cells may be used to isolate cancer cells through selective manipulation of microbead-cell complexes in a chip format. After the cancer cells are lysed to obtain cellular molecules, microbeads that allows for the specific hybridization of target mRNA molecules may be used to separate the mRNA molecules on a chip through selective manipulation of mRNA-bound microbeads from cell lysate mixture. The mRNA-bound microbeads may be further transported to a location on the chip for further reverse-transcription of mRNA to cDNA followed by cDNA amplification. The amplified cDNA molecules may then be manipulated using the present invention in a procedure of coupling the cDNA onto microbead surfaces and manipulating the cDNA-microbead complexes in a chip format.

Because the present invention can handle and process molecules and other moieties in a chip format and is applicable to all steps of bioanalytical steps and procedures, the method allows for a number of bioanalytical processes integrated on a chip and/or a number interconnected chips. Such integrated devices and systems have advantages in terms of automation, simplicity, flexibility, integration, reduced consumption of reagents, result accuracy and minimum contamination. Thus, the present invention addresses another critical limitation in current biochip application, i.e., the lack of integration capability. Currently, many biochip-based methods can be applied only to certain steps in bioanalytical procedures. Furthermore, certain biochip methods exploit physical forces generated using the external structures that are not incorporated in chip, imposing limitations for miniaturization, automation and integration of biochip-based systems. Both these shortcomings are addressed by the present invention.

The present invention further expands and enhances the capabilities of molecule manipulation in a chip-format with the choice of binding partners, e.g., microparticles, with special physical properties. By utilizing different types of microparticles with unique physical properties, the molecule manipulation can be achieved using a variety of physical force generation mechanisms. In addition, different particles having different physical properties can be used simultaneously to handle and manipulate multiple types of moieties (e.g., DNAs, proteins, mRNAs and other biomolecules) because these particles can be selectively manipulated.

The present methods can be used for manipulating any types of moieties when the moieties are involved in certain processes, such as physical, chemical, biological, biophysical or biochemical processes, etc., in a chip format. The moieties include the ones that can be manipulated directly by various physical forces and preferably, the ones that cannot be manipulated directly by various physical forces and have to be manipulated through the manipulation of their binding partners. In specific embodiments, moieties to be manipulated are cells, cellular organelles, viruses, molecules or an aggregate or complex thereof. Non-limiting examples of manipulatable cells include animal, plant, fungus, bacterium, recombinant cells or cultured cells. Non-limiting examples of manipulatable cellular organelles include nucleus, mitochondria, chloroplasts, ribosomes, ERs, Golgi apparatuses, lysosomes, proteasomes, secretory vesicles, vacuoles or microsomes. Manipulatable molecules can be inorganic molecules such as ions, organic molecules or a complex thereof. Non-limiting examples of manipulatable ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of manipulatable organic molecules include amino acids, peptides, proteins, nucleosides, nucleotides, oligonucleotides, nucleic acids, vitamins, monosaccharides, oligosaccharides, carbohydrates, lipids or a complex thereof.

Any binding partners that both bind to the moieties with desired affinity or specificity and are manipulatable with the desired physical force(s) can be used in the present methods. Unlike the moieties to be manipulated, which can or cannot be manipulated directly by the physical forces, the binding partners must be directly manipulatable with the desired physical force(s). One type of binding partner can possess properties that make it manipulatable by various physical forces. The binding partners can be cells such as animal, plant, fungus, bacterium or recombinant cells; cellular organelles such as nucleus, mitochondria, chloroplasts, ribosomes, ERs, Golgi apparatuses, lysosomes, proteasomes, secretory vesicles, vacuoles or microsomes; viruses, natural microparticles, synthetic microparticles or an aggregate or complex thereof. The microparticles used in the methods could have a dimension from about 0.01 micron to about ten centimeters. Preferably, the microparticles used in the methods have a dimension from about 0.1 micron to about several thousand microns. Microparticles could have any compositions, shapes and structures, provided that they properties that make them manipulatable by physical forces. Examples of microparticles that can be used in the methods include, but not limited to, plastic particles, polystyrene microbeads, glass beads, magnetic beads, hollow glass spheres, metal particles, or particles of complex compositions, microfabricated free-standing microstructures. In utilizing the present inventions, it is necessary that the choice of the binding partners in terms of physical properties, e.g., size, shape, density, structural composition, dielectric characteristics, magnetic properties, acoustic impedance, optical refractive index, should match the choice of the type of the manipulation forces and manipulation methods. In the case of utilizing multiple types of binding partners for simultaneous manipulation of multiple types of moieties, physical properties of each binding partner should be chosen so that they can be selectively manipulated in a chip format.

The moiety to be manipulated can be coupled to the surface of the binding partner with any methods known in the art. For example, the moiety can be coupled to the surface of the binding partner directly or via a linker, preferably, a cleavable linker. The moiety can also be coupled to the surface of the binding partner via a covalent or a non-covalent linkage. Additionally, the moiety can be coupled to the surface of the binding partner via a specific or a non-specific binding. Preferably, the linkage between the moiety and the surface of the binding partner is a cleavable linkage, e.g., a linkage that is cleavable by a chemical, physical or an enzymatic treatment. The coupling step or the decoupling step, if there is one, can be carried out on or off the chip.

Any physical forces can be used in the present methods. For instances, a dielectrophoresis force or a traveling-wave dielectrophoresis force such as the ones effected on electrically polarized particles via electrical fields generated by microelectrodes energized with AC (alternating current) electric signals, a magnetic force such as one effected on magnetic particles via magnetic fields generated by ferromagnetic material or by a microelectromagnetic unit, an acoustic force such as one effected on many types of particles via a standing-wave acoustic field, a traveling-wave acoustic field generated by a piezoelectric material energized with electrical signals, an electrostatic force such as one effected on charged particles via a DC electric field, a mechanical force such as fluidic flow force, an optical radiation force such as one effected on various types of particles via laser tweezers, or a thermal convection force, can be used. In utilizing the present inventions, it is necessary that the choice of the type of the manipulation forces and manipulation methods should match the choice of the binding partners in terms of physical properties and manipulation methods are realized in a chip format.

The present methods can be used in any chip format. For example, the methods can be used on silicon, silicon dioxide, silicon nitride, plastic, glass, ceramic, photoresist or rubber chips. In addition, the methods can be used on a chemchip, i.e., on which chemical reactions are carried out, a biochip, i.e., on which biological reactions are carried out, or a combination of a biochemchip. The chip used for the present invention has the built-in structures that can be energized by an external energy source and can produce physical forces to act on the binding partners and binding partner-moiety complexes. In many cases, the built-in structures are fabricated on or in a chip substrate. For example, microfabricated spiral electrode structures on a glass chip may be used for isolating, concentrating and manipulating microparticles.

The physical force used in the present methods are effected through a combination of the structure that is external to the chip and the structure that is built-in on the chip. The external structures are energy sources that can be connected to the built-in structures for energizing the built-in structures to generate a physical force such as dielectrophoresis force, magnetic force, acoustic force, electrostatic force, mechanical force or optical radiation force. The built-in structures can comprise a single unit or a plurality of units, each unit is, when energized and in combination with the external structure, capable of effecting the physical force on the binding partner. In the case of a plurality of units, the built-in structure may further comprise the means for selectively energizing any one of the plurality of units.

The present methods can be used for any type of manipulations. Non-limiting examples of the manipulations include transportation, focusing, enrichment, concentration, aggregation, trapping, repulsion, levitation, separation, fractionation, isolation or linear or other directed motion of the moieties. Of particular importance is the selective manipulation, e.g., separation, isolation, fractionation, enrichment, of one or more target moieties from a mixture.

In another aspect, the invention is directed to a method for manipulating a moiety which further comprises a step of decoupling the moiety from the surface of the binding partner after the moiety is manipulated. The nature of the decoupling step depends on the nature of the moiety, the binding partner, the surface modification of the partner and the manipulation step. Generally, the condition of the decoupling step is the opposite of the conditions that favor the binding between the moiety and the binding partner. For example, if a moiety binds to the binding partner at a high salt concentration, the moiety can be decoupled from the binding partner at a low salt concentration. Similarly, if a moiety binds to the binding partner through a specific linkage or a linker, the moiety can be decoupled from the binding partner by subjecting the linkage to a condition or agent that specifically cleaves the linkage.

In a specific embodiment, the moiety to be manipulated is a DNA, the binding partner is a porous bead and the DNA is reversibly absorbed onto the surface of the porous bead in a buffer containing high salt concentration. Alternatively, the DNA specifically binds to the surface of a binding partner (e.g., polystyrene beads) via sequence specific hybridization or binding to an anti-DNA antibody.

In another specific embodiment, the moiety to be manipulated is a mRNA and the mRNA specifically binds to the surface of a binding partner (e.g., polystyrene beads and magnetic beads) that is modified to contain oligo-dT polynucleotide.

In still another specific embodiment, the moiety to be manipulated is a protein and the protein non-specifically binds to the surface of a binding partner that is modified with a detergent, e.g., SDS. Alternatively, the protein specifically binds to the surface of a binding partner that is modified with an antibody that specifically recognizes the protein.

In still another specific embodiment, the moiety to be manipulated is a cell and the cell specifically binds to the surfaces of a binding partner (e.g. magnetic beads) that is modified to contain specific antibodies against the cells.

In yet another specific embodiment, the moiety to be manipulated is substantially coupled onto surface of the binding partner. Preferably, the moiety to be manipulated is completely coupled onto surface of the binding partner.

In yet another specific embodiment, a plurality of moieties is manipulated. The plurality of moieties can be manipulated sequentially or simultaneously. The plurality of moieties can be manipulated via a single binding partner or a plurality of binding partners. Preferably, the plurality of moieties is manipulated via a plurality of corresponding binding partners.

In still another aspect, the invention is directed to a method for isolating an intracellular moiety from a target cell, which method comprises: a) coupling a target cell to be isolated from a biosample onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) obtaining an intracellular moiety from said isolated target cell; d) coupling said obtained intracellular moiety onto surface of a second binding partner of said intracellular moiety to form an intracellular moiety-binding partner complex; and e) isolating said intracellular moiety-binding partner complex with a physical force in a chip format, wherein said isolation is effected through a combination of a structure that is external to said chip and a structure that is built-in in said chip.

In yet another aspect, the invention is directed to a method for generating a cDNA library in a microfluidic application, which method comprises: a) coupling a target cell to be isolated onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) lysing said isolated target cell; d) decoupling and removing said first binding partner from said lysed target cell; e) coupling mRNA to be isolated from said lysed target cell onto surface of a second binding partner of said mRNA to form a mRNA-binding partner complex; f) isolating said mRNA-binding partner complex with a physical force in a chip format, wherein said isolation is effected through a combination of a structure that is external to said chip and a structure that is built-in in said chip, and g) transporting said isolated mRNA-binding partner complex to a different chamber and reverse transcribing said transported mRNA into a cDNA library.

In yet another aspect, the invention is directed to a method for determining the gene expression a target cell in a microfluidic application, which method comprises: a) coupling a target cell to be isolated onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) lysing said isolated target cell; d) decoupling and removing said first binding partner from said lysed target cell; e) coupling mRNA to be isolated from said lysed target cell onto surface of a second binding partner of said mRNA to form a mRNA-binding partner complex; f) isolating said mRNA-binding partner complex with a physical force in a chip format, wherein said isolation is effected through a combination of a structure that is external to said chip and a structure that is built-in in said chip; and g) determining the quantities of the isolated mRNA molecules.

In yet another aspect, the invention is directed to a kit for manipulating a moiety in a microfluidic application, which kit comprises: a) a binding partner onto the surface of which a moiety to be manipulated can be coupled to form a moiety-binding partner complex; b) means for coupling said moiety onto the surface of said binding partner; and c) a chip on which said moiety-binding partner complex can be manipulated with a physical force that is effected through a combination of a structure that is external to said chip and a structure that is built-in in said chip.

(A) Molecules are suspended in a solution placed on a biochip;

(B) Molecules are coupled onto microparticle surfaces;

(C) Under applied electrical signals to the linear, parallel electrode elements on the biochip, molecule-microparticle complexes are levitated (or manipulated) onto certain heights above the chip surface.

Figure 2:
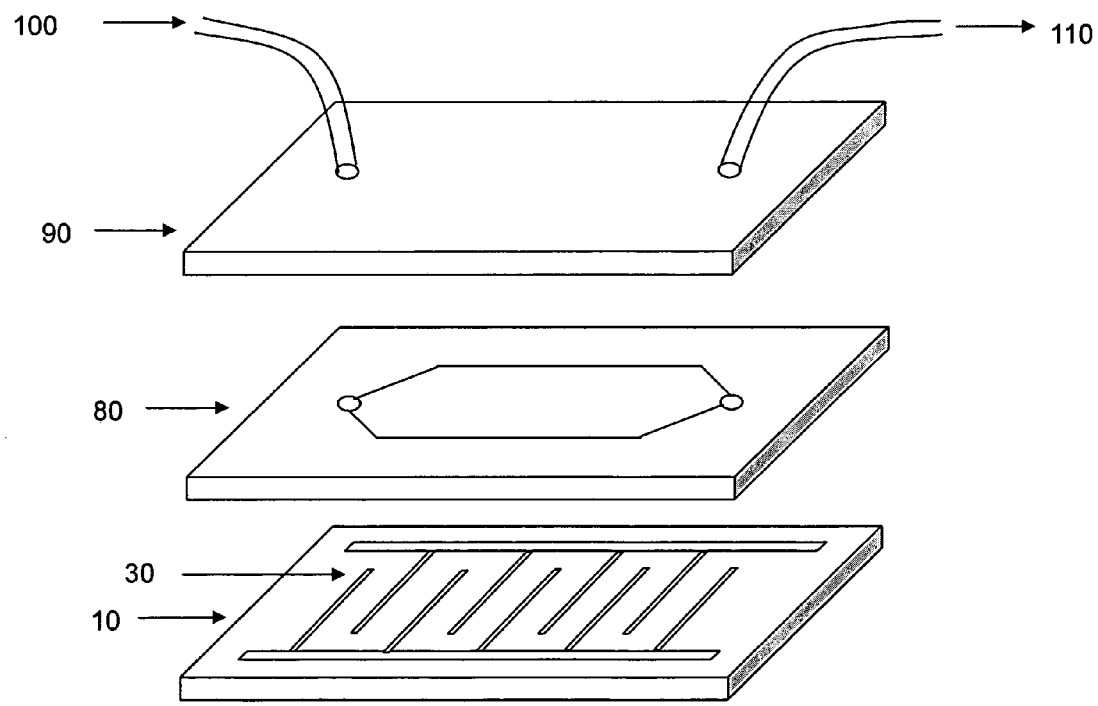

FIG. 2 depicts schematic representation of a fluidic chamber for moiety, e.g., molecule, manipulation that includes a biochip on the bottom, a spacer and a top plate. The molecule manipulation utilizes dielectrophoresis forces.

FIG. 3 depicts exemplary electrode structures that may be used for dielectrophoretic manipulation of binding partners and moieties complexes, e.g., molecules and molecule-particle complexes.

Figure 4:
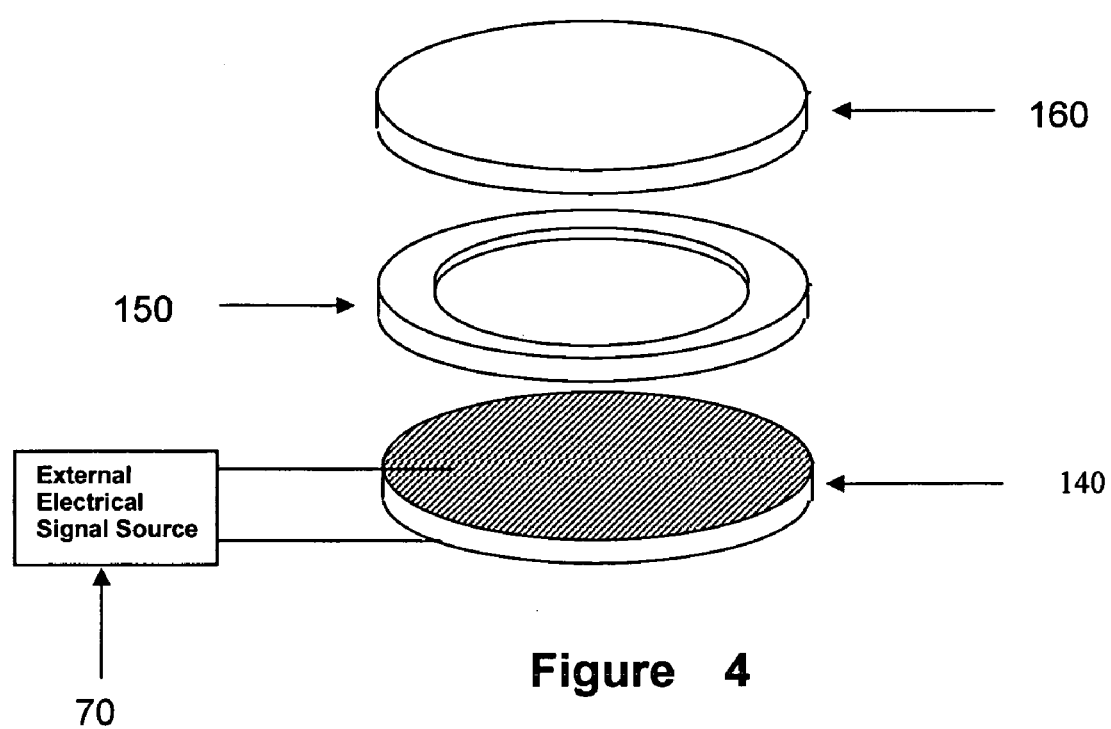

FIG. 4 depicts schematic representation of a fluidic chamber for acoustic manipulation of moieties, e.g., molecules. The chamber includes a piezoelectric transducer element on the bottom, a spacer, and a top reflective plate.

FIG. 5 depicts exemplary electrode structures that may be used for transportation of moieties, e.g., molecules, through traveling-wave-dielectrophoresis of binding partner-moiety complexes, e.g., molecules-particle complexes. Linear, parallel electrode array is used:

(A) Schematic drawing of the top view of the electrode array with molecule-microparticle complexes introduced on the electrodes;

(B) Schematic drawing of the cross-sectional view of the electrode array and molecules-microparticle complexes are subjected to a traveling-wave-dielectrophoresis force; and (C) Schematic drawing of the cross sectional view showing that molecules-microparticle complexes are transported to the end of the electrode array.

Figure 6:
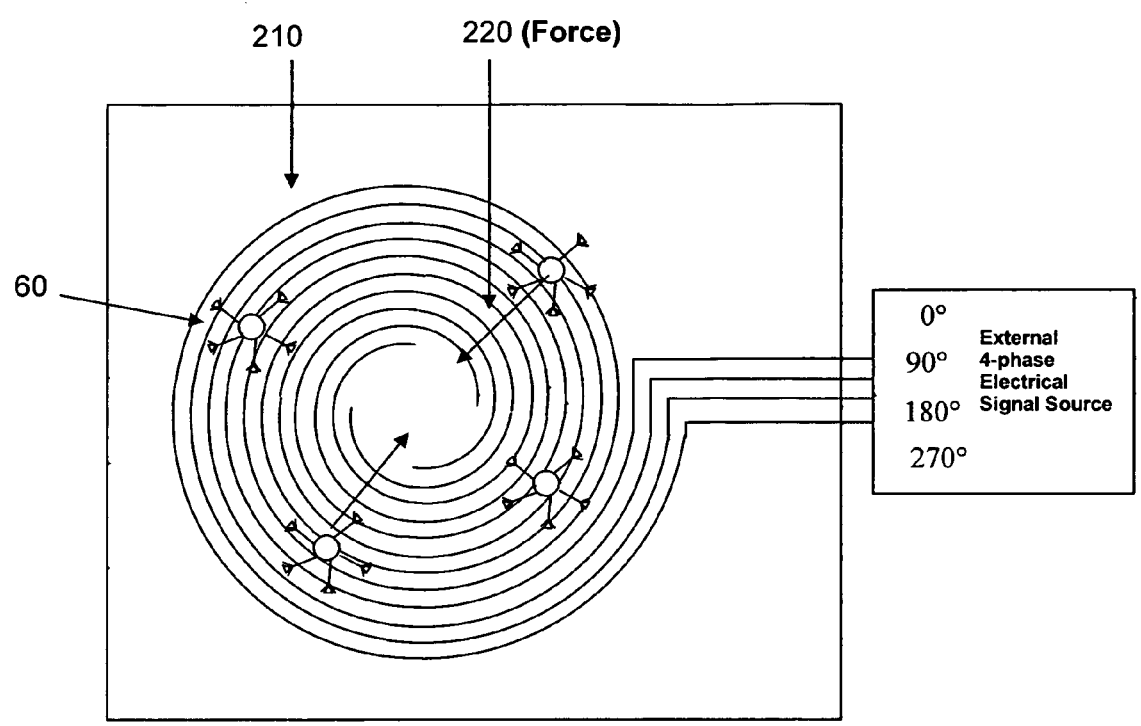

FIG. 6 depicts exemplary electrode structures that may be used for focusing, transporting, isolating and directing moieties, e.g., molecules, through traveling-wave dielectrophoresis of complexes of binding partners and moieties, e.g., molecule-particle complexes. Spiral electrode array comprising four parallel, linear spiral electrode elements is used.

FIG. 7 depicts exemplary electrode structures that may be used for transporting moieties, e.g., molecules, through traveling-wave electrophoresis of complexes of binding partners and moieties, e.g., molecule-microparticle complexes. Microparticles are electrically charged. Linear electrode array is used.

FIG. 8 depicts schematic representative example of binding partner, e.g., micro-particle, based on-chip manipulation of moieties, e.g., molecules, for directing and focusing on to the chip surfaces:

(A) Molecules are suspended in a solution placed on a biochip;

(B) Molecules are coupled onto microparticle surfaces; and (C) Under applied electrical signals to the electrode elements on the biochip, molecule-microparticle complexes are directed (focused or manipulated) into the chip surfaces.

FIG. 9 depicts exemplary manipulation of binding partners and moieties complexes, e.g., molecules and molecule-particle complexes, using dielectrophoresis due to a polynomial electrode array:

(A) Molecule-microparticle complexes are manipulated into the center region between the electrode elements; and (B) Molecule-microparticle complexes are manipulated onto the electrode edges.

FIG. 10 depicts exemplary manipulation of binding partners and moieties complexes, e.g., molecules and molecule-particle complexes, using dielectrophoresis due to an interdigitated, castellated electrode array:

(A) Molecule-microparticle complexes are manipulated into and trapped at the electrode bay regions between the electrode edges; and (B) Molecule-microparticle complexes are manipulated onto and trapped at the electrode edges.

FIG. 11 depicts exemplary manipulation of mixtures of different types of moieties, e.g., molecule mixtures:

(A) Molecule mixtures are placed in a chamber comprising a biochip at a chamber bottom;

(B) Microparticles are used to couple/link/bind target molecules from a molecule mixture;

(C) Target-molecule-microparticle complexes are attracted onto the electrode plane and at electrode edge regions;

(D) Other unbound molecules are washed away from the chamber whilst the molecule-microparticle complexes are trapped on the electrode edges; and (E) Molecules are uncoupled or disassociated from microparticle surfaces.

FIG. 12 depicts exemplary manipulation of mixtures of different types of moieties, e.g., molecule mixtures:

(A) Molecule mixtures are placed in a chamber comprising a biochip at a chamber bottom;

(B) Two types of microparticles are used to couple/link/bind two types of target molecules from a molecule mixture;

(C) Molecule-microparticle complexes are attracted onto the electrode plane and at electrode edge regions;

(D) Other unbound molecules are washed away from the chamber whilst the molecule-microparticle complexes are trapped on the electrode edges; and (E) Two types of molecule-microparticle complexes are separated by addressing the electrodes with different electrical signals.

Figure 13A:
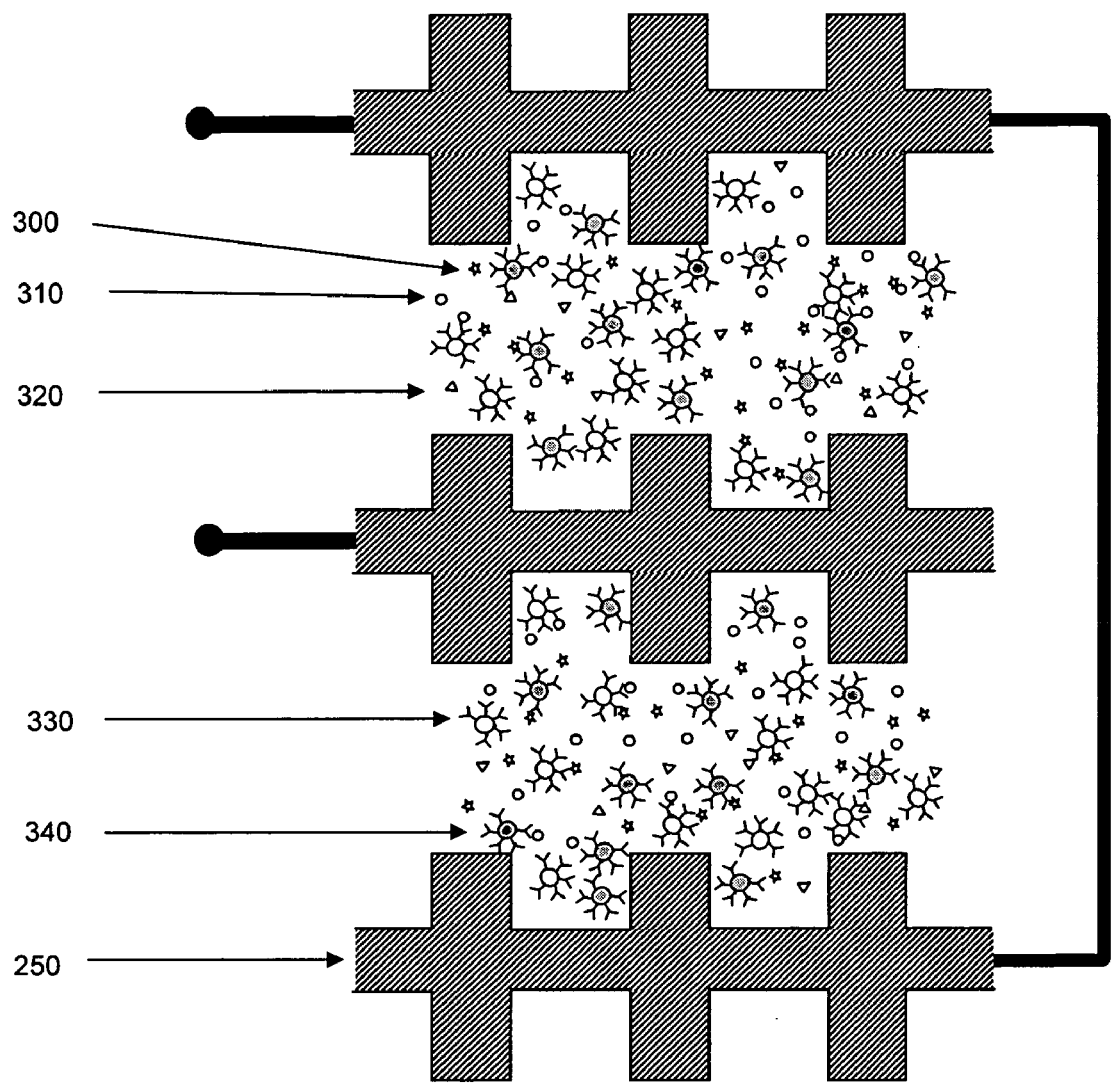
Figure 13B:
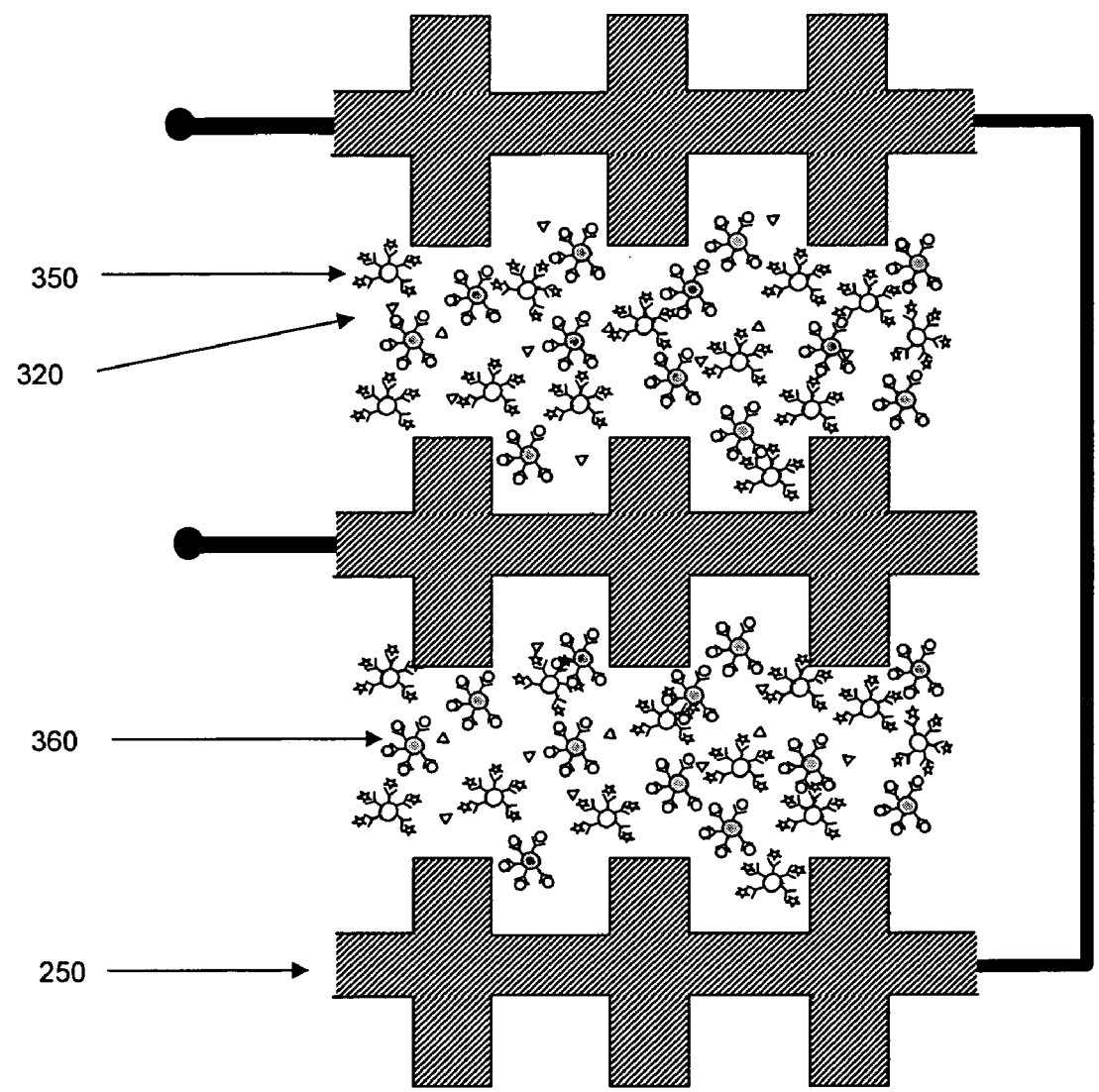
Figure 13C:
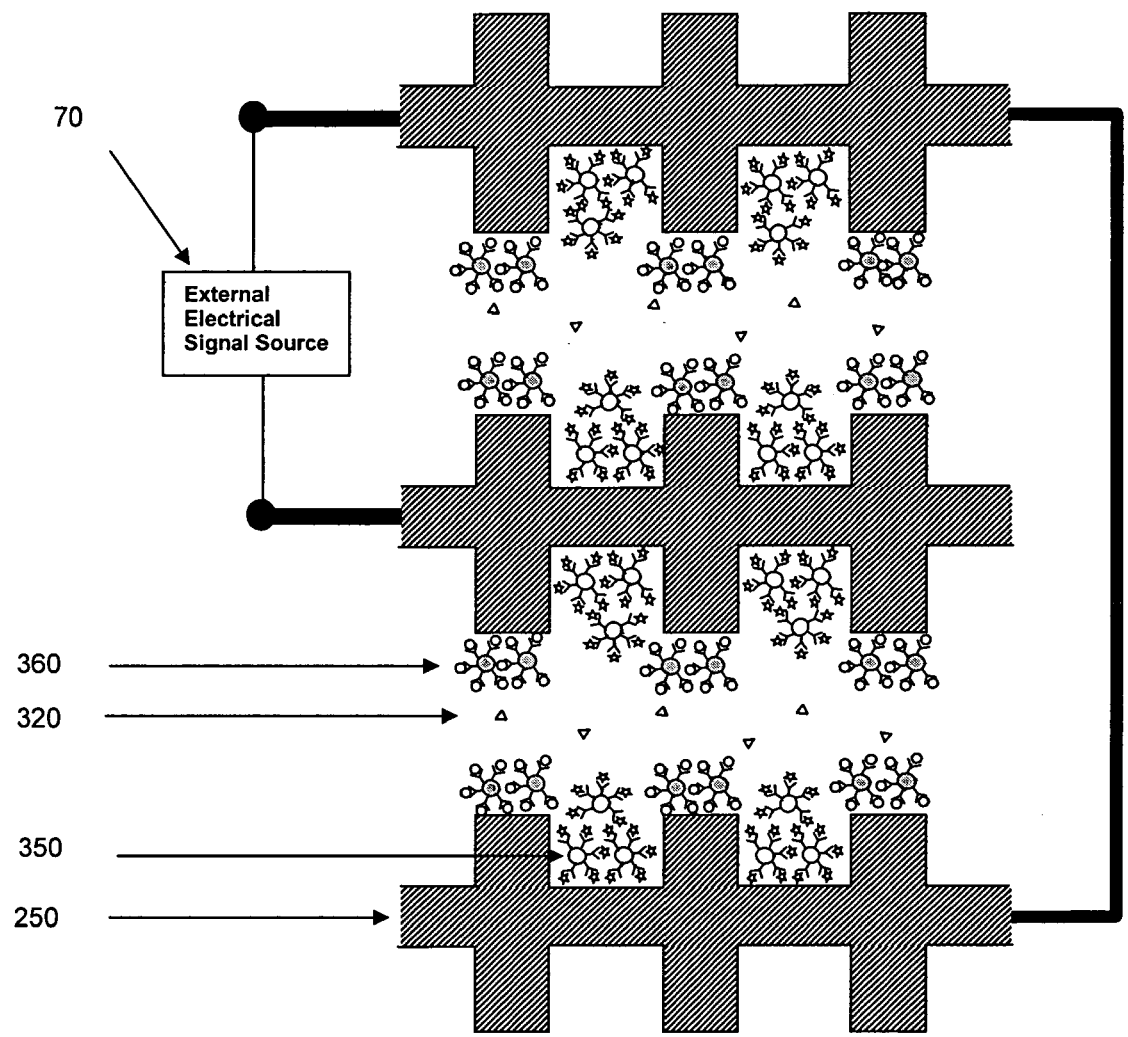

FIG. 13 shows an example of manipulating two types of target molecules from a molecule mixture simultaneously using a fluidic chamber similar to that shown in FIG. 2. FIG. 13A shows a molecule mixture introduced on an interdigitated electrode array. FIG. 13B shows that the two types of target molecules are coupled to their corresponding binding partners. FIG. 13C shows that the two types of target molecule-binding partner complexes are separated on the electrode chip.

Figure 14:
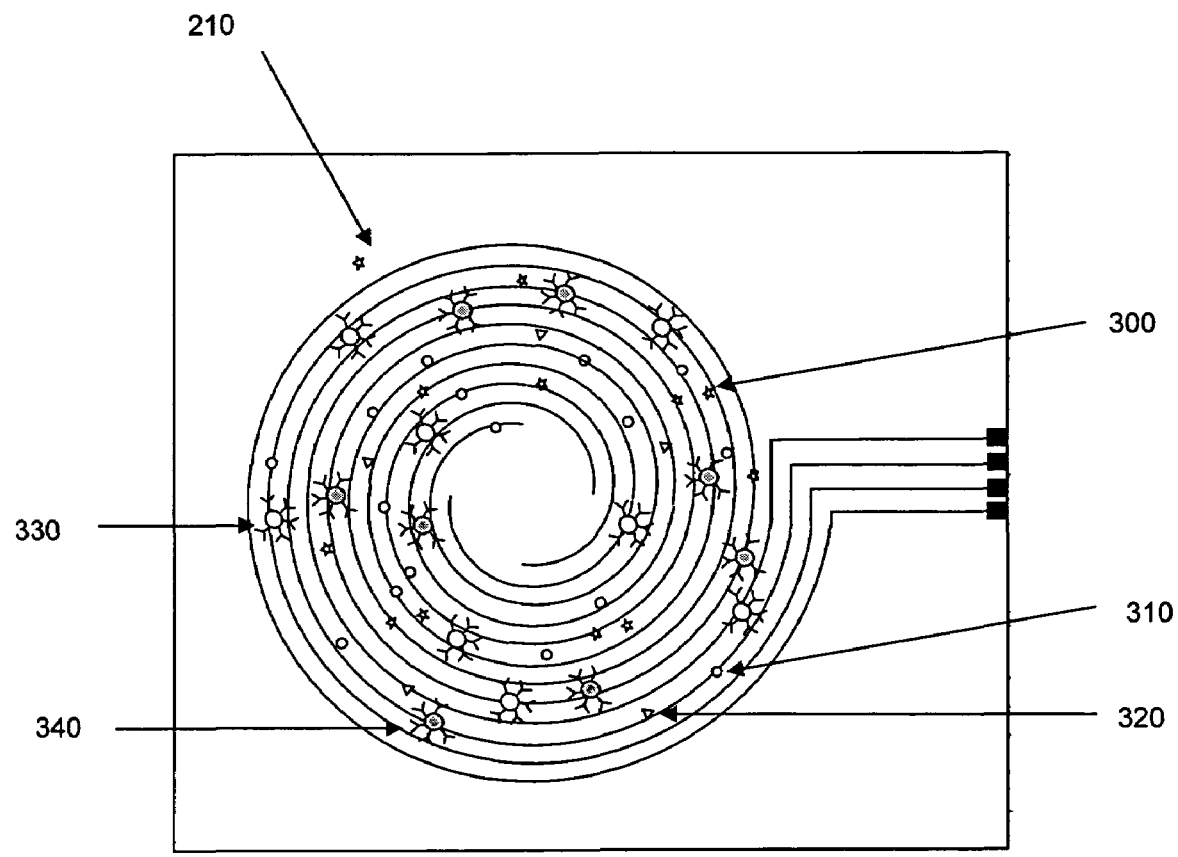
Figure 14:
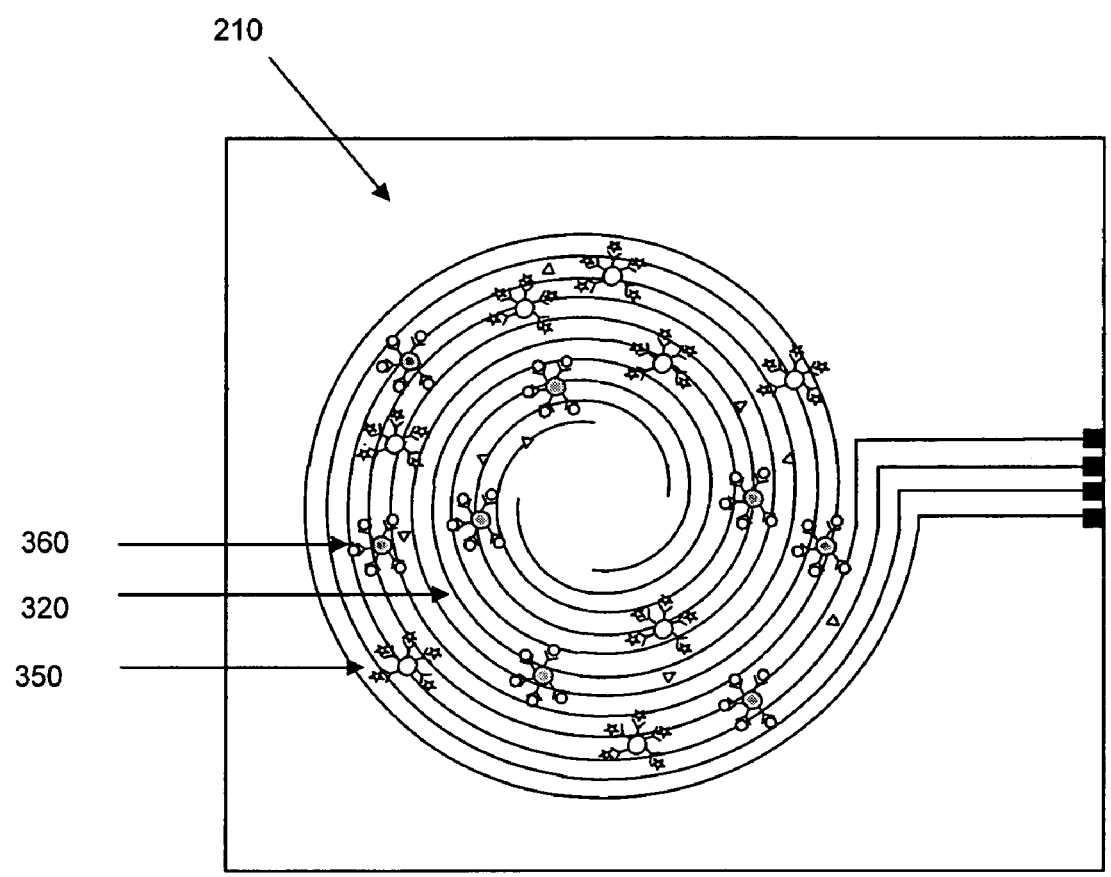
Figure 14:
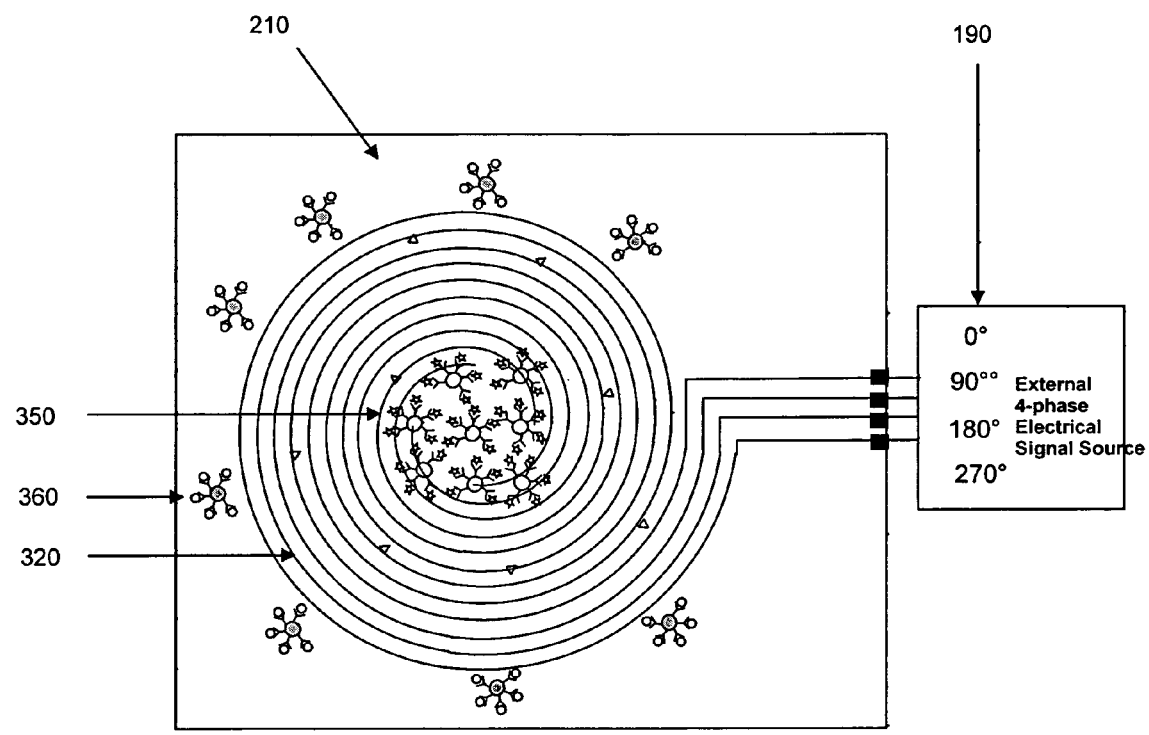

FIG. 14 shows an example of manipulating two types of target molecules from a molecule mixture simultaneously using a fluidic chamber similar to that shown in FIG. 2. FIG. 14A shows a molecule mixture introduced on a spiral electrode array. FIG. 14B shows that the two types of target molecules are coupled to their corresponding binding partners. FIG. 14C shows that the two types of target molecule-binding partner complexes are separated on the electrode chip.

Figure 15:
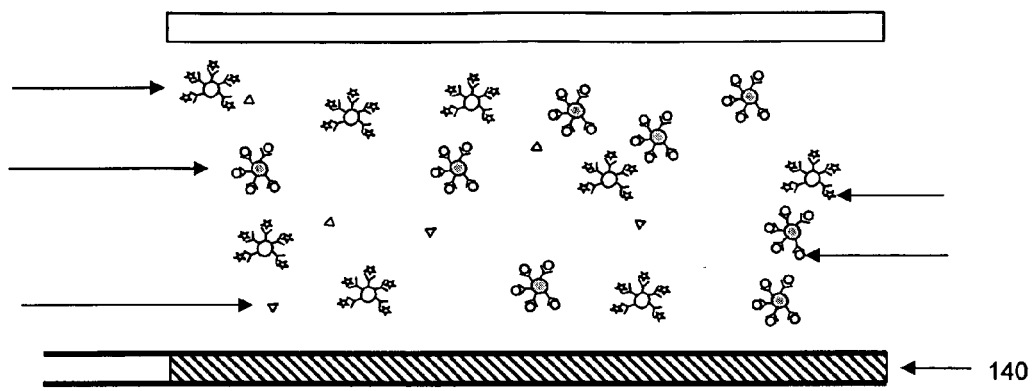
Figure 15:
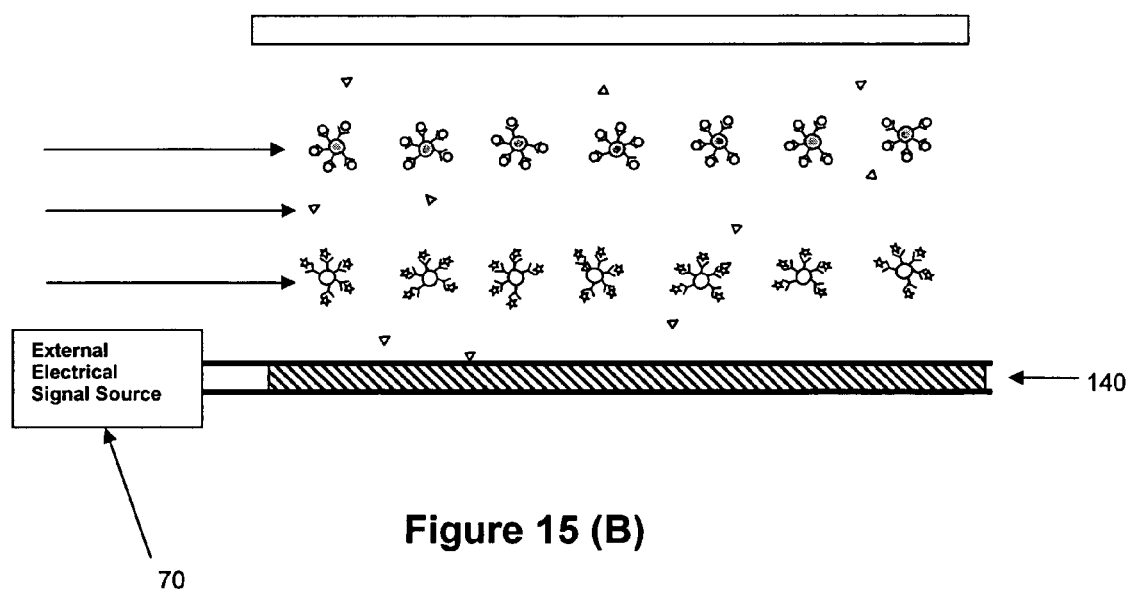

FIG. 15 shows an example of manipulating a molecule mixture in an acoustic fluidic chamber similar to that shown in FIG. 4. FIG. 15A shows the cross-sectional view of an acoustic chamber, in which two types of target molecules are coupled onto their corresponding binding partners. FIG. 15B shows that the two types of target molecule-binding partner complexes are positioned to different heights in the acoustic chamber.

MODES OF CARRYING OUT THE INVENTION

A. Definitions

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, "microfluidic application" refers to the use of microscale devices, e.g., the characteristic dimension of basic structural elements is in the range between less than 1 micron to cm scale, for fluidic manipulation and process, typically for performing specific biological, biochemical or chemical reactions and procedures. The specific areas include, but are not limited to, biochips, i.e., microchips for biologically related reactions and processes, chemchips, i.e., microchips for chemical reactions, or a combination thereof.

As used herein, "moiety" refers to any substance whose manipulation in a chip format is desirable. Normally, the dimension of the moiety should not exceed 1 cm. Preferably, the size of the moiety is too small to be manipulated directly by physical force in a chip format. Non-limiting examples of moieties that can be manipulated through the present methods include cells, cellular organelles, viruses, molecules, e.g., proteins, DNAs and RNAs, or an aggregate or complex thereof.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 μm) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein; "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "binding partners" refers to any substances that both bind to the moieties with desired affinity or specificity and are manipulatable with the desired physical force(s). Non-limiting examples of the binding partners include cells, cellular organelles, viruses, microparticles, or an aggregate or complex thereof, or an aggregate or complex of molecules.

As used herein, "microparticles" refers to particles of any shape, any composition, any complex structures that are manipulatable by desired physical force(s) in microfluidic settings or applications. The microparticles used in the methods could have a dimension from about 0.01 micron to about ten centimeters. Preferably, the microparticles used in the methods have a dimension from about 0.1 micron to about several thousand microns. Examples of the microparticles include, but are not limited to, plastic particles, polystyrene microbeads, glass beads, magnetic beads, hollow glass spheres, metal particles, particles of complex compositions, microfabricated free-standing microstructures, etc.

As used herein, "manipulation" refers to moving or processing of the moieties, which results in one-, two- or three-dimensional movement of the moiety, in a chip format, whether within a single chip or between or among multiple chips. Non-limiting examples of the manipulations include transportation, focusing, enrichment, concentration, aggregation, trapping, repulsion, levitation, separation, isolation or linear or other directed motion of the moieties. For effective manipulation, the binding partner and the physical force used in the method must be compatible. For example, binding partners with magnetic properties-must be used with magnetic force. Similarly, binding partners with certain dielectric properties, e.g., plastic particles, polystyrene microbeads, must be used with dielectrophoretic force. And binding partners with electrostatic charge(s) must be used with electrostatic force.

As used herein, "the moiety is not directly manipulatable" by a particular physical force means that no observable movement of the moiety can be detected when the moiety itself not coupled to a binding partner is acted upon by the particular physical force:

As used herein, "chip" refers to a solid substrate with a single or a plurality of one-, two- or three-dimensional micro structures on which certain processes, such as physical, chemical, biological, biophysical or biochemical processes, etc., can be carried out. The size of the chips useable in the present methods can vary considerably, e.g., from about 1 mm² to about 0.25 m². Preferably, the size of the chips useable in the present methods is from about 4 mm²-to about 25 cm² with a characteristic dimension from about 1 mm to about 5 cm. The shape of the chips useable in the present methods can also vary-considerably, from regular shapes such as square, rectangle or circle, to other irregular shapes. Examples of the chip include, but are not limited to the dielectrophoresis electrode array on a glass substrate (e.g., Dielectrophoretic Manipulation of Particles by Wang et al., in IEEE Transaction on Industry Applications, Vol. 33, No. 3, May/June, 1997, pages 660–669"), individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541–546), capillary electrophoresis chip (e.g., Combination of Sample-Preconcentration and Capillary Electrophoresis On-Chip by Lichtenberg, et al., in Micro Total Analysis Systems 2000 edited by A. van den Berg et al., pages 307–310), electromagnetic chip disclosed in the co-pending U.S. patent application Ser. No. 09/399,299, filed Sep. 17, 1999, and PCT/US99/21417, filed Sep. 17, 1999, the disclosure of which is incorporated by reference in their entireties.

As used herein, "physical force" refers to any force that moves the binding partners of the moieties without chemically or biologically reacting with the binding partners and the moieties, or with minimal chemical or biological reactions with the binding partners and the moieties so that the biological/chemical functions/properties of the binding partners and the moieties are not altered as a result of such reactions.

As used herein, "the moiety to be manipulated is substantially coupled onto surface of the binding partner" means that ascertain percentage, and preferably a majority, of the moiety to be manipulated is coupled onto surface of the binding partner and can be manipulated by a suitable physical force via manipulation of the binding partner. Ordinarily, at least 5% of the moiety to be manipulated is coupled onto surface of the binding partner. Preferably, at least 10%, 20%, 30%, 40%, 50%, 60%, 70%, 80% or 90% of the moiety to be manipulated is coupled onto surface of the binding partner. The percentage of the coupled moiety includes the percentage of the moiety coupled onto surface of a particular type of binding partner or a plurality of binding partners. When a plurality of binding partners is used, the moiety can be coupled onto surface of the plurality of binding partners simultaneously or sequentially.

As used herein, "the moiety to be manipulated is completely coupled onto surface of the binding partner" means that at least 90% of the moiety to be manipulated is coupled onto surface of the binding partner. Preferably, at least 91%, 92%, 93%, 94%, 95%, 96%, 97%, 98%, 99% or 100% of the moiety to be manipulated is coupled onto surface of the binding partner. The percentage of the coupled moiety includes the percentage of the moiety coupled onto surface of a particular type of binding partner or a plurality of binding partners. When a plurality of binding partners is used, the moiety can be coupled onto surface of the plurality of binding partners simultaneously or sequentially.

As used herein, "intracellular moiety" refers to any moiety that resides or is otherwise located within a cell, i.e., located in the cytoplasm or matrix of cellular organelle, attached to any intracellular membrane, resides or is otherwise located within periplasma, if there is one, or resides or is otherwise located on cell surface, i.e., attached on the outer surface of cytoplasm membrane or cell wall, if there is one.

For clarity of disclosure, and not by way of limitation, the detailed description of the invention is divided into the subsections that follow.

B. Moieties

The present methods can be used for manipulating any types of moieties when the moieties are involved in certain processes such as physical, chemical, biological, biophysical or biochemical processes, etc., in a chip format. Moieties to be manipulated can be cells, cellular organelles viruses, molecules or an aggregate or complex thereof. Moieties to be manipulated can be pure substances or can exist in a mixture of substances wherein the target moiety is only one of the substances in the mixture. For example, cancer cells in the blood from leukemia patients, cancer cells in the solid tissues from patients with solid tumors and fetal cells in maternal blood from pregnant women can be the moieties to be manipulated. Similarly, various blood cells such as red and white blood cells in the blood can be the moieties to be manipulated. DNA molecules, mRNA molecules, certain types of protein molecules, or all protein molecules from a cell lysate can be moieties to be manipulated.

Non-limiting examples of manipulatable cells include animal cells, plant cells, fungi, bacteria, recombinant cells or cultured cells. Animal, plant cells, fungus, bacterium cells to be manipulated can be derived from any genus or subgenus of the Animalia, Plantae, fungus or bacterium kingdom. Cells derived from any genus or subgenus of ciliates, cellular slime molds, flagellates and microsporidia can also be manipulated. Cells derived from birds such as chickens, vertebrates such fish and mammals such as mice, rats, rabbits, cats, dogs, pigs, cows, ox, sheep, goats, horses, monkeys and other non-human primates, and humans can be manipulated by the present methods.

For animal cells, cells derived from a particular tissue to organ can be manipulated. For example, connective, epithelium, muscle or nerve tissue cells can be manipulated. Similarly, cells derived from an accessory organ of the eye, annulospiral organ, auditory organ, Chievitz organ, circumventricular organ, Corti organ, critical organ, enamel organ, end organ, external female genital organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subformical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be manipulated. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be manipulated. Further, cells derived from any plants, fungi such as yeasts, bacteria such as eubacteria or archaebacteria can be manipulated. Recombinant cells derived from any eucaryotic or prokaryotic sources such as animal, plant, fungus or bacterium cells can also be manipulated. Cells from various types of body fluid such as blood, urine, saliva, bone marrow, sperm or other ascitic fluids, and subfractions thereof, e.g., serum or plasma, can also be manipulated.

Manipulatable cellular organelles include nucleus, mitochondria, chloroplasts, ribosomes, ERs, Golgi apparatuses, lysosomes, proteasomes, secretory vesicles, vacuoles or microsomes. Manipulatable viruses, whether intact viruses or any viral structures, e.g., viral particles, in the virus life cycle can be derived from viruses such as Class I viruses, Class II viruses, Class III viruses, Class IV viruses, Class V viruses or Class VI viruses.

Manipulatable molecules can be inorganic molecules such as ions, organic molecules or a complex thereof. Non-limiting examples of manipulatable ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of manipulatable organic molecules include amino acids, peptides, proteins, nucleosides, nucleotides, oligonucleotides, nucleic acids, vitamins, monosaccharides, oligosaccharides, carbohydrates, lipids or a complex thereof.

Any amino acids can be manipulated by the present methods. For example, a D- and a L-amino-acid can be manipulated. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be manipulated.

Any proteins or peptides can be manipulated by the present methods. For example, membrane proteins such as receptor proteins on cell membranes, enzymes, transport proteins such as ion channels and pumps, nutrient or storage proteins, contractile or motile proteins such as actins and myosins, structural proteins, defense protein or regulatory proteins such as antibodies, hormones and growth factors can be manipulated. Proteineous or peptidic antigens can also be manipulated.

Any nucleic acids, including single-, double and triple-stranded nucleic acids, can be manipulated by the present methods. Examples of such nucleic acids include DNA, such as A-, B- or Z-form DNA, and RNA such as mRNA, tRNA and rRNA.

Any nucleosides can be manipulated by the present methods. Examples of such nucleosides include adenosine, guanosine, cytidine, thymidine and uridine. Any nucleotides can be manipulated by the present methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be manipulated by the present methods. For example, water-soluble vitamins such as thiamine, riboflavin, nicotinic acid, pantothenic acid, pyridoxine, biotin, folate, vitamin $B_{12}$ and ascorbic acid can be manipulated. Similarly, fat-soluble vitamins such as vitamin A, vitamin D, vitamin E, and vitamin K can be manipulated.

Any monosaccharides, whether D- or L-monosaccharides and whether aldoses or ketoses, can be manipulated by the present methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be manipulated by the present methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters: The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

C. Binding Partners

Any binding partners that both bind to the moieties with desired affinity or specificity and are manipulatable with the compatible physical force(s) can be used in the present methods. The binding partners can be cells such as animal, plant, fungus or bacterium cells; cellular organelles such as nucleus, mitochondria, chloroplasts, ribosomes, ERs, Golgi apparatuses, lysosomes, proteasomes, secretory vesicles, vacuoles or microsomes; viruses, microparticles or an aggregate or complex thereof. The cells, cellular organelles and viruses described in Section B can also be used as binding partners.

Preferably, the microparticles used in the methods have a dimension from about 0.01 micron to about several thousand microns. Non-limiting examples of the microparticles used in the methods include plastic particles, polystyrene microbeads, glass beads, magnetic beads, hollow glass spheres, metal particles, particles of complex compositions, microfabricated free-standing microstructures (e.g., Design of asynchronous dielectric micromotors by Hagedom et al., in *Journal of Electrostatics,* 1994, Volume: 33, Pages 159–185). Particles of complex compositions refer to the particles that comprise or consists of multiple compositional elements, for example, a metallic sphere covered with a thin layer of non-conducting polymer film.

In choosing binding partners, the type, material, composition, structure and size of the binding partners have be comparable with the manipulation format in the specific applications. For example, magnetic beads should be used as binding partners if the means for manipulating moiety-binding-partner are magnetic field-based. Beads having appropriate dielectric properties should be used if dielectrophoretic field is used for manipulating moiety-binding-partner. The choice of the beads is further related with specific manipulation details. For example, for separating target moiety from a mixture of molecules and particles by dielectrophoresis manipulation, binding partner's dielectric properties should be significantly different from those of molecules and particles so that when binding partners are coupled with the target moiety, the moiety-binding-partner complexes may be selectively manipulated by dielectrophoresis. In an example of separating target cancer cells from a mixture of normal cells, the cancer cells have similar dielectric properties to those of normal cells and all the cells behave similarly in their dielectrophoretic responses, e.g., negative dielectrophoresis. In this case, the binding partners preferably should be more dielectrically-polarizable than their suspending medium and will exhibit positive dielectrophoresis. Thus, such binding partners-cancer-cell complexes can be selectively manipulated through positive dielectrophoresis forces while other cells experience negative dielectrophoresis forces.

The separation can be achieved by collecting and trapping the positive dielectrophoresis exhibiting cancer-cell-binding-partner complexes on electrode edges while removing other cells with forces such as fluidic forces. Similar methods may be applied for the case of using negative dielectrophoresis-exhibiting particles for selective separation of target cells from cell mixtures where most or many cell types exhibit positive dielectrophoresis. Those who are skilled in dielectrophoresis theory and application for manipulating cells and microbeads can readily determine what properties the binding partners should posses in terms of size, composition and geometry in order for them to exhibit positive and/or negative dielectrophoresis under specific field conditions and can readily choose appropriate dielectrophoresis-manipulation methods.

In the case of manipulating multiple types of moieties (e.g. certain mRNAs and protein molecules), numerous types of binding partners that have specific physical properties to allow them to be selectively manipulated may be used. An example is the use of microbeads that have unique dielectric properties to separate two types of molecules from a molecule mixture. The requirements for these two types of microbeads may be as follows. The surface of each particle type is modified so that each particle type allows for specific binding of one type of target molecules. If the target molecules are mRNA molecules and a type of protein, the surfaces of particles may be modified with poly-T (T-T-T-T . . . ) molecules and antibodies against the target protein for the two types of particles used for manipulation of mRNA and protein respectively. The dielectric properties of the two particle types may be chosen so that under one particular applied field frequency $f_1$, both types exhibit positive dielectrophoresis and under the field of another frequency $f_2$, one particle type exhibit positive and another type exhibit negative dielectrophoresis. Thus, in operation, both types of particles are introduced into the molecule mixture and are allowed for mRNA molecules and target protein from the mixture to bind to the particle surfaces. The separation of the mRNA-particle complexes and protein—protein complexes from the molecule mixture may be achieved by collecting and trapping the positive dielectrophoresis exhibiting mRNA-particle complexes and protein-particle complexes on electrode edges under the first field frequency $f_1$ in a chip comprising dielectrophoresis electrodes while removing other molecules in the mixture with additional forces such as fluidic forces (e.g., see example shown in FIG. 11). After removing the other unwanted molecules from the mixture and obtaining the target mRNA-particle complexes and protein-particle complexes on the chip, the additional forces that have removed the unwanted molecules are stopped and electrical field is changed to the second field frequency $f_2$. Under this field condition, only one type of molecule-particle complexes (e.g., protein-particle complexes) exhibit positive dielectrophoresis, and the other type of molecule-particle complexes (e.g., mRNA-particle complexes) exhibit negative dielectrophoresis. The additional force may be applied again to remove the molecule-particle complexes (e.g. mRNA-particle complex) that exhibit negative dielectrophoresis. This leaves behind on the chip the positive-dielectrophoresis exhibiting molecule-particle complexes (e.g., protein-particle complexes). Those who are skilled in dielectrophoresis theory and application for manipulating cells and microbeads can readily determine what properties the particles should posses in terms of size, composition and geometry in order for them to exhibit positive and/or negative dielectrophoresis under different field conditions and can readily choose appropriate dielectrophoresis-manipulation methods.

D. Coupling and Decoupling of the Moieties to the Surface of the Binding Partners The moiety to be manipulated can be coupled to the surface of the binding partner with any methods known in the art. For example, the moiety can be coupled to the surface of the binding partner directly or via a linker, preferably, a cleavable linker. The moiety can also be coupled to the surface of the binding partner via a covalent or a non-covalent linkage. Additionally, the moiety can be coupled to the surface of the binding partner via a specific or a non-specific binding. Preferably, the linkage between the moiety and the surface of the binding partner is a cleavable linkage, e.g., a linkage that is cleavable by a chemical, physical or an enzymatic treatment.

Linkers can be any moiety suitable to associate the moiety and the binding partner. Such linkers and linkages include, but are not limited to, amino acid or peptidic linkages, typically containing between about one and about 100 amino acids, more generally between about 10 and about 60 amino acids, even more generally between about 10 and about 30 amino acids. Chemical linkers, such as heterobifunctional cleavable cross-linkers, include but are not limited to, N-succinimidyl (4-iodoacetyl)-aminobenzoate, sulfosuccinimydil (4-iodoacetyl)-aminobenzoate, 4-succinimidyl-oxycarbonyl-a-(2-pyridyldithio)toluene, sulfosuccinimidyl-6-[a-methyl-a-(pyridyldithiol)-toluamido]hexanoate, N-succinimidyl-3-(-2-pyridyldithio)-proprionate, succinimidyl 6[3(-(-2-pyridyldithio)-proprionamido]hexanoate, sulfosuccinimidyl 6[3(-(-2-pyridyldithio)-propionamido] hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the moiety and the binding partner, photocleavable linkers and acid cleavable linkers.

Other exemplary linkers and linkages that are suitable for chemically linking the moiety and the binding partner include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H 1$, $C_H 2$, and $C_H 3$, from the constant region of human $IgG_1$ (Batra et al., *Molecular Immunol.*, 30:379–386 ((1993)). In some embodiments, several linkers may be included in order to take advantage of desired properties of each linker.

Acid cleavable linkers, photocleavable and heat sensitive linkers may also be used, particularly where it may be necessary to cleave the moiety from the surface of the binding partner after manipulation. Acid cleavable linkers include, but are not limited to, bismaleimideothoxy propane, adipic acid dihydrazide linkers (Fattom et al., *Infection & Immun.*, 60:584–589 (1992)) and acid labile transferrin conjugates that contain a sufficient portion of transferrin to permit entry into the intracellular transferrin cycling pathway (Welhöner et al., *J. Biol. Chem.*, 266:4309–4314(1991)).

Photocleavable linkers are linkers that are cleaved upon exposure to light (see, e.g., Goldmacher et al., *Bioconj. Chem.*, 3:104–107 (1992)), thereby releasing the moiety upon exposure to light. Examples of such photocleavable linkers include a nitrobenzyl group as a photocleavable protective group for cysteine (Hazum et al., in *Pept., Proc. Eur. Pept. Symp.,* 16th, Brunfeldt, K (Ed), pp. 105–110 (1981)), water soluble photocleavable copolymers, including hydroxypropylmethacrylamide copolymer, glycine copolymer, fluorescein copolymer and methylrhodamine copolymer (Yen et al., *Makromol. Chem,* 190:69–82 ((1989)), a cross-linker and reagent that undergoes photolytic degradation upon exposure to near UV light (350 nm) (Goldmacher et al., *Bioconj. Chem.,* 3:104–107 ((1992)) and nitrobenzyloxycarbonyl chloride cross linking reagents that produce photocleavable linkages (Senter et al., *Photochem. Photobiol,* 42:231–237 (1985)).

Other linkers, include trityl linkers, particularly, derivatized trityl groups to generate a genus of conjugates that provide for release of the moiety at various degrees of acidity or alkalinity, (U.S. Pat. No. 5,612,474). Additional linking moieties are described, for example, in Huston et al., *Proc. Natl. Acad. Sci. U.S.A.,* 85:5879–5883 (1988), Whitlow, et al., *Protein Engineering,* 6:989–995 (1993), Newton et al., *Biochemistry,* 35:545–553 (1996), Cumber et al., *Bioconj. Chem.,* 3:397–401 (1992), Ladumer et al., *J. Mol. Biol.,* 273:330–337 (1997) and in U.S. Pat. No. 4,894,443. In some cases, several linkers may be included in order to take advantage of desired properties of each linker.

The preferred linkage used in the present methods are those effected through biotin-straptoavidin interaction, antigen-antibody interaction, ligand-receptor interaction, or nucleic complementary sequence hybridization.

Chemical linkers and peptide linkers may be inserted by covalently coupling the linker to the moiety and the binding partner. Peptide linkers may also be linked to a peptide moiety by expressing DNA encoding the linker and the peptide moiety as a fusion protein. Peptide linkers may also be linked to a peptide binding partner by expressing DNA encoding the linker and the peptide binding partner as a fusion protein.

The following description illustrates how molecules, as the moieties to be manipulated, can be coupled onto surfaces of microparticles, which act as the binding partners. In one example, molecules may be passively absorbed on microparticle surface, depending on the nature of the molecules and the particle surface compositions. Such absorption may be specific as for the type of the molecules, e.g., protein vs. nucleic acids, and non-specific as for the specific molecule composition and structures. Protein molecules may be passively absorbed onto surfaces of polystyrene microbeads. Such passively absorbed proteins are generally stable. DNA molecules may be bound to glass bead surfaces under a high-salt condition. The physical forces such as hydrophobic interactions and ionic electrolyte-related electrostatic interactions may be involved in passive absorption.

In another example, molecules may be specifically bound to microparticle surfaces. The specific binding or coupling may involve a covalent or non-covalent reaction between the molecules to be manipulated and the molecules on microparticle surfaces. For example, protein molecules may be covalently attached to the surface of polystyrene microbeads by carbodiimide for carboxylate functional beads or glutaraldehyde for amino beads. Another example is concerned with straptoavidin-coated microbeads. Such microparticles may be coupled with biotinylated molecules through biotin-straptoavidin interaction.

In still another example, specific linking molecules may be used to couple the molecules to be manipulated on microparticle surfaces. The high affinity binding between straptoavidin and biotin molecules may be used. One embodiment of this linkage may be used follows. Straptoavidin molecules are first deposited or linked to microparticle surfaces so that all the microparticles are pre-covered with straptoavidin molecules. The molecules to be manipulated are linked to biotin molecules. The step of coupling the molecules onto microparticle surfaces may involve the reaction between biotin (that is linked with molecules to be manipulated) and straptoavidin (that is linked with microparticles to be manipulated) molecules. Furthermore, it is preferable to use cleavable linking molecules for such an application. So, if required, the linking molecules may be cleaved after manipulation so that the molecules may be de-coupled from microparticle surfaces.

The following description illustrates the coupling of three classes of bio-molecules, i.e., DNA, mRNA and protein molecules, to the surface of microparticles. DNA molecules can be bound onto particle surfaces in a specific or nonspecific manner. For non-specific binding, porous bead, such as glass particles, or particles having siloxy groups, can be used. DNA can be absorbed onto the beads under appropriate buffer conditions, such as high salt. The binding of DNA molecules on the beads is easily reversible by putting the bead in a low salt or no salt buffer. So DNA can be released for further analysis by simply reducing buffer salt concentration. Specific DNA binding to the beads can be realized through sequence specific hybridization, such as single strand DNA hybridization capture, DNA triplex formation and anti-DNA antibody binding.

For capturing mRNA molecules, microparticle surfaces are modified to attach oligo-dT poly-nucleotides. Under appropriate conditions, poly-A tails of mRNA molecules in a sample will specifically bind to poly-T at particle surfaces. By changing particle suspension temperature, mRNA molecules can be easily released from the micro-particles and be available for further bioanalysis. For specific mRNA isolation, complementary oligo-nucleotides or cDNA can be linked to the micro-particles and used to hybridize against target mRNA molecules. The release of mRNA from the micro-particles can be realized by denaturation.

Proteins can be bound to microparticles specifically or nonspecifically. For nonspecific protein binding, microparticle surfaces can be chemically modified by detergent molecules, such as SDS, since it is well known that protein molecules non-specifically bind to SDS. Thus, coupling the SDS on particle surface will then allow protein molecules to bind to particle surfaces. For specific protein capture, antibodies can be coupled onto the micro-particles.

In some cases, after manipulating the moiety-binding partner, e.g., molecule-microparticle, complexes to desired locations, microparticles do not interfere with reactions the molecules involve in. Thus, it may not be necessary to decouple molecules from microparticle surfaces. However, in other cases, it may be desirable or necessary after the manipulating step. The nature of the decoupling step depends on the nature of the moiety, the binding partner, the surface modification of the partner and the manipulation step. Generally, the condition of the decoupling step is the opposite of the conditions that favor the binding between the moiety and the binding partner. For example, if a moiety binds to the binding partner at a high salt concentration, the moiety can be decoupled from the binding partner at a low salt concentration. Similarly, if a moiety binds to the binding partner through a specific linkage or a linker, the moiety can be decoupled from the binding partner by subjecting the linkage to a condition or agent that specifically cleaves the linkage.

The following description illustrates the decoupling of several molecules from microparticle surfaces. If the molecules are specifically or non-specifically absorbed on microparticle surfaces, they may come off particle surfaces under proper physic-chemical conditions. For example, the DNA molecules absorbed onto glass surface under high-salt condition in solution may be re-dissolved in solutions if the salt (electrolyte) concentration is reduced. Certain covalent or non-covalent bindings between molecules and microparticle surfaces may be disrupted under proper conditions. For example, antibody-antigen binding occurs within certain pH values of the binding solution and electrolyte concentration and the antibody-antigen binding can be disrupted by changing the pH or electrolyte concentration to non-binding values or concentrations. For the case where linking molecules are used to couple molecules onto microparticle surfaces, it is preferable to use cleavable linking molecules. Thus, after manipulating molecule-microparticle complexes, linking molecules may be cleaved so that the molecules are de-coupled from microparticle surfaces.

E. Physical Forces

Any physical forces can be used in the present methods. For instances, a dielectrophoresis force, a traveling-wave dielectrophoresis force, a magnetic force such as one effected via a magnetic field generated by a ferromagnetic material or one effected via a microelectromagnetic unit, an acoustic force such as one effected via a standing-wave acoustic field or a traveling-wave acoustic field, an electrostatic force such as one effected via a DC electric field, a mechanical force such as fluidic flow force, or an optical radiation force such as one effected via a optical intensity field generated by laser tweezers, can be used.

Dielectrophoresis refers to the movement of polarized particles in a non-uniform AC electrical field. When a particle is placed in an electrical field, if the dielectric properties of the particle and its surrounding medium are different, dielectric polarization will occur to the particle. Thus, the electrical charges are induced at the particle/medium interface. If the applied field is non-uniform, then the interaction between the non-uniform field and the induced polarization charges will produce net force acting on the particle to cause particle motion towards the region of strong or weak field intensity. The net force acting on the particle is called dielectrophoretic force and the particle motion is dielectrophoresis. Dielectrophoretic force depends on the dielectric properties of the particles, particle surrounding medium, the frequency of the applied electrical field and the field distribution.

Traveling-wave dielectrophoresis is similar to dielectrophoresis in which the traveling-electric field interacts with the field-induced polarization and generates electrical forces acting on the particles. Particles are caused to move either with or against the direction of the traveling field. Traveling-wave dielectrophoretic forces depend on the dielectric properties of the particles and their suspending medium, the frequency and the magnitude of the traveling-field. The theory for dielectrophoresis and traveling-wave dielectrophoresis and the use of dielectrophoresis for manipulation and processing of microparticles may be found in various literatures (e.g., "Non-uniform Spatial Distributions of Both the Magnitude and Phase of AC Electric Fields determine Dielectrophoretic Forces by Wang et al., in *Biochim Biophys Acta Vol.* 1243, 1995, pages 185–194", "Dielectrophoretic Manipulation of Particles by Wang et al, in IEEE Transaction on Industry Applications, Vol. 33, No. 3, May/June, 1997, pages 660–669", "Electrokinetic behavior of colloidal particles in traveling electric fields: studies using yeast cells by Huang et al, in J. Phys. D: Appl. Phys., Vol. 26, pages 1528–1535", "Positioning and manipulation of cells and microparticles using miniaturized electric field traps and traveling waves. By Fuhr et al., in Sensors and Materials. Vol. 7: pages 131–146", "Dielectrophoretic manipulation of cells using spiral electrodes by Wang, X-B. et al., in *Biophys. J.* Volume 72, pages 1887–1899, 1997", "Separation of human breast cancer cells from blood by differential dielectric affinity by Becker et al, in *Proc. Natl. Acad. Sci., Vol.*, 92, January 1995, pages 860–864"). The manipulation of microparticles with dielectrophoresis and traveling wave dielectrophoresis include concentration/aggregation, trapping, repulsion, linear or other directed motion, levitation, separation of particles. Particles may be focused, enriched and trapped in specific regions of the electrode reaction chamber. Particles may be separated into different subpopulations over a microscopic scale. Particles may be transported over certain distances. The electrical field distribution necessary for specific particle manipulation depends on the dimension and geometry of microelectrode structures and may be designed using dielectrophoresis theory and electrical field simulation methods.

The dielectrophoretic force, $F_{DEP\,z}$ acting on a particle of radius r subjected to a non-uniform electrical field can be given by $$F_{DEP\,z} = 2\pi\epsilon_m r^3 \chi_{DEP} \nabla E_{rms}^2 \cdot \vec{a}_z$$

where $E_{rms}$ is the RMS value of the field strength, $\epsilon_m$ is the dielectric permitivity of the medium. $\chi_{DEP}$ is the particle dielectric polarization factor or dielectrophoresis polarization factor, given by $$\chi_{DEP} = \text{Re}\left(\frac{\varepsilon_p^* - \varepsilon_m^*}{\varepsilon_p^* + 2\varepsilon_m^*}\right),$$

"Re" refers to the real part of the "complex number". The symbol $$\varepsilon_x^* = \varepsilon_x - j\frac{\sigma_x}{2\pi f}$$

is the complex permitivity (of the particle x=p, and the medium x=m). The parameters $\epsilon_p$ and $\sigma_p$ are the effective permitivity and conductivity of the particle, respectively. These parameters may be frequency dependent. For example, a typical biological cell will have frequency dependent, effective conductivity and permitivity, at least, because of cytoplasm membrane polarization.

The above equation for the dielectrophoretic force can also be written as $$F_{DEP\,z} = 2\pi\epsilon_m r^3 \chi_{DEP} V^2 p(z) \vec{a}_z$$

where p(z) is the square-field distribution for a unit-voltage excitation (V=1 V) on the electrodes, V is the applied voltage.

There are generally two types of dielectrophoresis, positive dielectrophoresis and negative dielectrophoresis. In positive dielectrophoresis, particles are moved by dielectrophoresis forces towards the strong field regions. In negative dielectrophoresis, particles are moved by dielectrophoresis forces towards weak field regions. Whether particles exhibit positive and negative dielectrophoresis depends on whether particles are more or less polarizable than the surrounding medium.

Traveling-wave DEP force refers to the force that is generated on particles or molecules due to a traveling-wave electric field. A traveling-wave electric field is characterized by the non-uniform distribution of the phase values of AC electric field components.

Here we analyze the traveling-wave DEP force for an ideal traveling-wave field. The dielectrophoretic force $F_{DEP}$ acting on a particle of radius r subjected to a traveling-wave electrical field $E_{TWD}=E\cos(2\pi(ft-z/\chi_0))\vec{a}_x$ (i.e., a x-direction field is traveling along the z-direction) is given by $$F_{TWD} = -2\pi\epsilon_m r^3 \cdot \zeta_{TWD} E^2 \cdot \vec{a}_z$$

where E is the magnitude of the field strength, $\epsilon_m$ is the dielectric permittivity of the medium. $\zeta_{TWD}$ is the particle polarization factor, given by $$\zeta_{TWD} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $$\varepsilon_x^* = \varepsilon_x - j\frac{\sigma_x}{2\pi f}$$

is the complex permittivity (of the particle x=p, and the medium x=m). The parameters $\epsilon_p$ and $\sigma_p$ are the effective permittivity and conductivity of the particle, respectively. These parameters may be frequency dependent.

Particles such as biological cells having different dielectric property (as defined by permittivity and conductivity) will experience different dielectrophoretic forces. For traveling-wave DEP manipulation of particles (including biological cells), traveling-wave DEP forces acting on a particle of 10 micron in diameter can vary somewhere between 0.01 and 10000 pN.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

Both dielectrophoresis and traveling-wave dielectrophoresis forces acting on particles depend on not only the field distributions (e.g., the magnitude, frequency and phase distribution of electrical field components; the modulation of the field for magnitude and/or frequency) but also the dielectric properties of the particles and the medium in which particles are suspended or placed. For dielectrophoresis, if particles are more polarizable than the medium (e.g., having larger conductivities and/or permittivities depending on the applied frequency), particles will experience positive dielectrophoresis forces and are directed towards the strong field regions. The particles that are less polarizable than the surrounding medium will experience negative dielectrophoresis forces and are directed towards the weak field regions. For traveling wave dielectrophoresis, particles may experience dielectrophoresis forces that drive them in the same direction as the field traveling direction or against it, dependent on the polarization factor $\zeta_{TWD}$. The following papers provide basic theories and practices for dielectrophoresis and traveling-wave-dielectrophoresis: Huang, et al., *J. Phys. D: Appl. Phys.* 26:1528–1535 (1993); Wang, et al., *Biochim. Biophys. Acta.* 1243:185–194 (1995); Wang, et al., *IEEE Trans. Ind. Appl.* 33:660–669 (1997).

Microparticles may be manipulated with magnetic forces. Magnetic forces refer to the forces acting on a particle due to the application of a magnetic field. In general, particles have to be magnetic or paramagnetic when sufficient magnetic forces are needed to manipulate particles. We consider a typical magnetic particle made of super-dipole paramagnetic material. When the particle is subjected to a magnetic field $\overline{B}$, a magnetic dipole $\overline{\mu}$ is induced in the particle $$\overline{\mu} = V_p(\chi_p - \chi_m)\frac{\overline{B}}{\mu_m},$$
$$= V_p(\chi_p - \chi_m)\overline{H}_m$$

where $V_p$ is the particle volume, $\chi_p$ and $\chi_m$ are the volume susceptibility of the particle and its surrounding medium, $\mu_m$ is the magnetic permeability of medium, $\overline{H}_m$ is the magnetic field strength. The magnetic force $\overline{F}_{magnetic}$ acting on the particle is determined by the magnetic dipole moment and the magnetic field gradient:

$$\overline{F}_{magnetic} = 0.5\, V_p(\chi_p-\chi_m)\overline{H}_m \bullet \nabla \vec{B}_m,$$

where the symbols "●" and "∇" refer to dot-product and gradient operations, respectively. Clearly, whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{F_{magnetic}}{6\pi r \eta_m}$$

where r is the particle radius and $\eta_m$ is the viscosity of the surrounding medium. Thus to achieve sufficiently large magnetic manipulation force, the following factors should be considered: (1) the volume susceptibility of the magnetic particles should be maximized; (2) magnetic field strength should be maximized; and (3) Magnetic field strength gradient should be maximized.

Paramagnetic particles are preferred whose magnetic dipoles are induced by externally applied magnetic fields and return to zero when external field is turned off. For such applications, commercially available paramagnetic or other magnetic particles may be used. Many of these particles are between below micron (e.g., 50 nm–0.5 micron) and tens of microns. They may have different structures and compositions. One type of magnetic particles has ferromagnetic materials encapsulated in thin latex, e.g., polystyrene, shells. Another type of magnetic particles has ferromagnetic nanoparticles diffused in and mixed with latex e.g., polystyrene, surroundings. The surfaces of both these particle types are polystyrene in nature and may be modified to link to various types of molecules.

The manipulation of magnetic particles requires the magnetic field distribution generated over microscopic scales. One approach for generating such magnetic fields is the use of microelectromagnetic units. Such units can induce or produce magnetic field when an electrical current is applied. The switching on/off status and the magnitudes of the electrical current applied to these units will determine the magnetic field distribution. The structure and dimension of the microelectromagnetic units may be designed according to the requirement of the magnetic field distribution. Manipulation of magnetic particles includes the directed movement, focusing and trapping of magnetic particles. The motion of magnetic particles in a magnetic field is termed "magnetophoresis". Theories and practice of magnetophoresis for cell separation and other applications may be found in various literatures (e.g., Magnetic Microspheres in Cell Separation, by Kronick, P. L. in Methods of Cell Separation, Volume 3, edited by N. Catsimpoolas, 1980, pages 115–139; Use of magnetic techniques for the isolation of cells, by Safarik I. And Safarikova M., in J. of Chromatography, 1999, Volume 722(B), pages 33–53; A fully integrated micromachined magnetic particle separator, by Ahn C. H. et al., in J. of Microelectromechanical systems, 1996, Volume 5, pages 151–157).

Microparticles may be manipulated using acoustic forces, i.e., using acoustic fields. In one case, standing-wave acoustic field is generated by the superimposition of an acoustic wave generated from an acoustic wave source and its reflective wave. Particles in standing-wave acoustic fields experience the so-called acoustic radiation force that depends on the acoustic impedance of the particles and their surrounding medium. The acoustic impedance is the product of the density of the material and the velocity of acoustic-wave in the material. Particles with higher acoustic impedance than its surrounding medium are directed towards the pressure nodes of the standing wave acoustic field. Particles experience different acoustic forces in different acoustic field distributions.

One method to generate the acoustic wave source is to use piezoelectric material. These materials, upon applying electrical fields at appropriate frequencies, can generate mechanical vibrations that are transmitted into the medium surrounding the materials. One type of piezoelectric materials is piezoelectric ceramics. Microelectrodes may be deposited on such ceramics to activate the piezoelectric ceramic and thus to produce appropriate acoustic wave fields. Various geometry and dimensions of microelectrodes may be used according to the requirement of different applications. The reflective walls are needed to generate standing-wave acoustic field. Acoustic wave fields of various frequencies may be applied, i.e., the fields at frequencies between kHz and hundred megahertz. In another case, one could use non-standing wave acoustic field, e.g., traveling-wave acoustic field. Traveling-wave acoustic field may impose forces on particles (see e.g., see, "Acoustic radiation pressure on a compressible sphere, by K. Yoshioka and Y. Kawashima in Acustica, 1955, Vol. 5, pages 167–173").

Particles not only experience forces from acoustic fields directly but also experience forces due to surrounding fluid because the fluid may be induced to move under traveling-wave acoustic field. Using acoustic fields, particles may be focussed, concentrated, trapped, levitated and transported in a microfluidic environment. Another mechanism for producing forces on particles in an acoustic field is through the acoustic-induced fluid convection. An acoustic field produced in a liquid may induced liquid convection. Such convection is dependent on the acoustic field distribution, properties of the liquid, the volume and structure of the chamber in which the liquid is placed. Such liquid convection will impose forces on particles placed in the liquid and the forces may be used for manipulating particles. One example of such manipulating forces may be exploited for enhancing mixing of liquid or mixing of particles into a liquid. For the present invention, such convection may be used to enhance the mixing of the binding partners with moiety in a suspension and to promote the interaction between the moiety and the binding partners.

A standing plane wave of ultrasound can be established by applying AC signals to the piezoelectric transducers. For example, the standing wave spatially varying along the z axis in a fluid can be expressed as:

$$\Delta p(z) = p_0 \sin(kz) \cos(\omega t)$$

where $\Delta p$ is acoustic pressure at z, $p_0$ is the acoustic pressure amplitude, k is the wave number ($2\pi/\chi$, where $\chi$ is the wavelength), z is the distance from the pressure node, $\omega$ is the angular frequency, and t is the time. According to the theory developed by Yoshioka and Kawashima (see, "Acoustic radiation pressure on a compressible sphere, by K. Yoshioka and Y. Kawashima in Acustica, 1955, Vol. 5, pages 167–173"), the radiation force $F_{acoustic}$ acting on a spherical particle in the stationary standing wave field is given by (see "Studies on particle separation by acoustic radiation force and electrostatic force by Yasuda K. et al. in Jpn. J. Appl. Physics, 1996, Volume 35, pages 3295–3299")

$$F_{acoustic} = -\frac{4\pi}{3} r^3 k E_{acoustic} A \sin(2kz)$$

where r is the particle radius, $E_{acoustic}$ is the average acoustic energy density, A is a constant given by $$A = \frac{5\rho_p - 2\rho_m}{2\rho_p + \rho_m} - \frac{\gamma_p}{\gamma_m}$$

where $\sigma_m$ and $\sigma_p$ are the density of the particle and the medium, $\gamma_m$ and $\gamma_p$ are the compressibility of the particle and medium, respectively. A is termed herein as the acoustic-polarization-factor.

When A>0, the particle moves towards the pressure node (z=0) of the standing wave.

When A<0, the particle moves away from the pressure node.

Clearly, particles having different density and compressibility will experience different acoustic-radiation-forces when they are placed into the same standing acoustic wave field. For example, the acoustic radiation force acting on a particle of 10 micron in diameter can vary somewhere between 0.01 and 1000 pN, depending on the established acoustic energy density distribution.

The piezoelectric transducers are made from "piezoelectric materials" that produce an electric field when exposed to a change in dimension caused by an imposed mechanical force (piezoelectric or generator effect). Conversely, an applied electric field will produce a mechanical stress (electrostrictive or motor effect) in the materials. They transform energy from mechanical to electrical and vice-versa. The piezoelectric effect was discovered by Pierre Curie and his brother Jacques in 1880. It is explained by the displacement of ions, causing the electric polarization of the materials' structural units. When an electric field is applied, the ions are displaced by electrostatic forces, resulting in the mechanical deformation of the whole material.

Microparticles may be manipulated using DC electric fields. DC electric field can exert an electrostatic force on charged particles. The force depends on the charge magnitude and polarity on the particles and depends on the field magnitude and direction. The particles with positive and negative charges may be directed to electrodes with negative and positive potentials, respectively. By designing microelectrode array in a microfluidic device, electric field distribution may be appropriately structured and realized. With DC electric fields, microparticles may be concentrated (enriched), focussed and moved (transported) in a microfluidic device. Proper dielectric coating may be applied on to DC electrodes to prevent and reduce undesired surface electrochemistry and to protect electrode surfaces.

The electrostatic force $F_E$ on a particle in an applied electrical field $E_z \vec{a}_z$ can be given by $$F_E = Q_p E_z \vec{a}_z$$

where $Q_p$ is the effective electric charge on the particle. The direction of the electrostatic force on the charged particle depends on the polarity of the particle charge as well as the applied-field direction.

Thermal convection forces refer to the forces acting on a moiety, e.g., a particle, due to the fluid-convection (liquid-convection) that is induced by a thermal gradient in the fluid. The thermal diffusion occurs in the fluid that drives the fluid towards a thermal equilibrium. This will cause a fluid convection. In addition, for an aqueous solution, the solution at a higher temperature tends to have a lower density than that at a lower temperature. Such a density difference is also not stable within the fluid so that convection will be setup. The use of thermal convection may facilitate liquid mixing. Certain directed thermal convection may act as an active force to bring down molecules from further distances.

Thermal gradient distributions may be established within a chip-based chamber where heating and/or cooling elements may be incorporated into the chip structures. A heating element may be a simple joule-heating resistor coil. Such coil could be microfabricated onto the chip. Take a coil having a resistance of 10 ohm as an example. Applying 0.2 A through the coil would result in 0.4 W joule heating-power. When the coil is located in an area <100 micron$^2$, this is an effective way of heat generation. Similarly, a cooling element may be a Peltier element that could draw heat upon applying electric potentials.

As an exemplary embodiment, the chip may incorporate an array of individually addressable heating elements. These elements are positioned or structurally arranged in certain order so that when each of or some of or all of elements are activated, thermal gradient distributions can be established to produce thermal convection. For example, if one heating element is activated, temperature increases in the liquid in the neighborhood of this element will induce fluid convection. In another exemplary embodiment, the chip may comprise multiple, interconnected heating units so that these units can be turned on or off in a synchronized order. Yet, in another example, the chip may comprise only one heating element that can be energized to produce heat and induce thermal convection in the liquid fluid.

Other physical forces may be applied. For example, mechanical forces, e.g., fluidic flow forces, may be used to transport microparticles. Optical radiation forces as exploited in "laser tweezers" may be used to focus, trap, levitate and manipulate microparticles. The optical radiation forces are the so-called gradient-forces when a material (e.g., a microparticle) with a refractive index different from that of the surrounding medium is placed in a light gradient. As light passes through polarizable material, it induces fluctuating dipoles. These dipoles interact with the electromagnetic field gradient, resulting in a force directed towards the brighter region of the light if the material has a refractive index larger than that of the surrounding medium. Conversely, an object with a refractive index lower than the surrounding medium experiences a force drawing it towards the darker region. The theory and practice of "laser tweezers" for various biological application are described in various literatures (e.g., "Making light work with optical tweezers, by Block S. M., in Nature, 1992, Volume 360, pages 493–496"; "Forces of a single-beam gradient laser trap on a dielectric sphere in the ray optics regime, by Ashkin, A., in Biophys. J., 1992, Volume 61, pages 569–582"; "Laser trapping in cell biology, by Wright et al., in IEEE J. of Quantum Electronics, 1990, Volume 26, pages 2148–2157"; "Laser manipulation of atoms and particles, by Chu S. in Science, 1991, Volume 253, pages 861–866"). The light field distribution and/or light intensity distribution may be produced with the built-in optical elements and arrays on a chip and the external optical signal sources, or may be produced with built-in the electro-optical elements and arrays on a chip and the external structures are electrical signal sources. In the former case, when the light produced by the optical signal sources passes through the built-in optical elements and arrays, light is processed by these elements/arrays through, e.g., reflection, focusing, interference, etc. Optical field distributions are generated in the regions around the chip. In the latter case, when the electrical signals from the external electrical signal sources are applied to the built-in electro-optical elements and arrays, light is produced from these elements and arrays and optical fields are generated in the regions around the chip.

F. Chips and Structures Internal and External to the Chips

The present methods can be used in any chip format. For example, the methods can be used on silicon, silicon dioxide, silicon nitride, plastic, glass, ceramic, photoresist or rubber chips. In addition, the methods can be used on a chemchip, i.e., on which chemical reactions are carried out, a biochip, i.e., on which biological reactions are carried out, or a combination of a biochemchip.

The physical forces used in the present methods are effected through a combination of the structure that is external to the chip and the structure that is built-in in the chip. The external structures are energy sources that can be connected to the built-in structures for energizing the built-in structures to generate a physical force such as dielectrophoresis force, magnetic force, acoustic force, electrostatic force, mechanical force or optical radiation force. The built-in structures comprise a single unit or a plurality of units, each unit is, when energized and in combination of the external structure, capable of effecting the physical force on the binding partner. In the case of a plurality of units, the built-in structure may further comprise the means for selectively energizing any one of the plurality of units.

In one example, when magnetic force is used to manipulate a complex of a moiety (e.g., DNA molecules) and its binding partner (e.g., surface modified magnetic beads that allows for binding of DNA molecules), the electromagnetic chip disclosed in the co-pending U.S. patent application Ser. No. 09/399,299, filed Sep. 16, 1999, which is incorporated by reference in its entirety, can be used in the methods. Typically, such electromagnetic chips with individually addressable micro-electromagnetic units comprise: a substrate; a plurality of micro-electromagnetic units on the substrate, each unit capable of inducing magnetic field upon applying electric current; means for selectively energizing any one of a plurality of units to induce a magnetic field therein. Preferably, the electromagnetic chips further comprise a functional layer coated on the surface of the chips for immobilizing certain types of molecules. In this example of magnetic manipulation of moiety-binding partner complexes, microelectromagnetic units are the built-in structures internal to the chip and the electrical current source that is connected to the microelectromagnetic units is the structures external to the chip. When the electric current from the external current source is applied to the microelectromagnetic units, magnetic fields will be generated in the regions around the microelectromagnetic units and magnetic forces will be produced on magnetic particles that are present in the region around the microelectromagnetic units. Typically, for the case of manipulation force being magnetic force, the built-in structures are electromagnetic units that are incorporated on a chip and the external structures are the electrical signal sources (e.g., current sources). When the appropriately designed and fabricated electromagnetic units are energized by the electrical signal sources, magnetic fields are generated in the regions around the chip. When the binding partner or binding partner-moiety complexes are subjected to such magnetic fields, magnetic forces are produced on them, and such forces are dependent on the magnetic field distribution, the magnetic properties of the binding partner or binding partner-moiety complexes and the magnetic properties of the medium that surrounds the binding partner or binding partner-moiety complexes.

In another example, when dielectrophoresis force and traveling-wave dielectrophoresis force are used to manipulate a complex of a moiety (e.g., protein molecules) and its binding partner. (e.g., surface modified polystyrene beads that allows for binding of protein molecules), the spiral electrode array on a glass chip, together with a phase-quadrature AC electrical signal source, can be used in the methods (see "Dielectrophoretic manipulation of cells using spiral electrodes by Wang, X-B. et al., in *Biophys. J.* Volume 72, pages 1887–1899, 1997"). In this example of dielectrophoretic manipulation of moiety-binding partner complexes, spiral electrode array is the built-in structures internal to the chip and the AC electrical signal source that is connected to the spiral electrodes is the structures external to the chip. When the AC electrical signals of appropriate phases from the external signal source are applied to the spiral electrode array, electrical fields will be generated in the regions around the spiral electrode array. Dielectrophoretic and traveling-wave dielectrophoretic forces will be produced on moiety-binding partner complexes that are present in the region around the spiral electrode array. Typically, for the case of manipulation force being dielectrophoresis and/or dielectrophoresis force, the built-in structures are the electrode elements and electrode arrays that are incorporated on a chip and the external structures are electrical signal sources. When the appropriately designed electrode elements and electrode arrays are energized by the electrical signal sources, non-uniform electrical fields are generated in the regions around the chip. When the binding partner or binding partner-moiety complexes are subjected to such non-uniform electrical fields, dielectrophoresis and/or traveling-wave dielectrophoresis forces acting on the binding partners or binding partner-moiety complexes are produced. Such forces are dependent on the interaction between the electrical field distributions and field induced dielectric polarization.

In still another example, when acoustic force is used to manipulate a complex of a moiety (e.g., cells) and its binding partner (e.g., surface modified polystyrene beads that allows for binding of cells), the phased array of piezoelectric transducers described in U.S. Pat. No. 6,029,518 by Oeftering, R. can be used in the methods. In this example of acoustic manipulation of moiety-binding partner complexes, the phased array of piezoelectric transducers is the built-in structures internal to the chip and the AC electrical signal source that is connected to the phased array is the structures external to the chip. When the AC electrical signals from the external signal source are applied to the phased array of piezoelectric transducers, acoustic wave will be generated from the piezoelectric transducers and transmitted into the regions around the piezoelectric transducer. Depending on the chamber structure comprising such a piezoelectric transducer, when moieties and moiety-binding partner complexes in a liquid suspension are introduced into the chamber, acoustic radiation forces will be produced on moieties and moiety-binding partner complexes. Typically, for the case of manipulation force being acoustic forces, the built-in structures are the piezoelectric elements or structures that are incorporated on a chip and the external structures are electrical signal sources. When the appropriately designed piezoelectric elements or structures are energized by the electrical signal sources, acoustic waves are generated from piezoelectric elements or structures and acoustic-wave fields are produced in the regions around the chip. When the binding partner or binding partner-moiety complexes are subjected to such acoustic fields, acoustic forces are produced on the binding partners or binding partner-moiety complexes and such forces are dependent on acoustic-wave field distribution, acoustic properties of the binding partners or binding partner-moiety complexes and acoustic properties of the medium that surrounds the binding partners or binding partner-moiety complexes.

For the case of manipulation force being electrostatic force, the built-in structures are the electrode elements and electrode arrays that are incorporated on a chip and the external structures are electrical signal sources (e.g., a DC current source). When the appropriately designed electrode elements and electrode arrays are energized by the electrical signal sources, electrical fields are generated in the regions around the chip. When the binding partner or binding partner-moiety complexes are subjected to electrical fields, electrostatic forces acting on the binding partners or binding partner-moiety complexes are produced. Such forces depend on the electrical field distributions and charge properties of the binding partners or binding partner-moiety complexes.

For the case of manipulation force being optical radiation force, one example of the built-in structures is the optical elements and arrays that are incorporated on a chip and the external structures is optical signal sources (e.g., a laser source). When the light produced by the optical signal sources passes through the built-in optical elements and arrays, optical fields are generated in the regions around the chip and the optical field distribution is dependent on the geometrical structures, sizes and compositions of the built-in optical elements and arrays. When the binding partner or binding partner-moiety complexes are subjected to optical fields, optical radiation forces acting on the binding partners or binding partner-moiety complexes are produced. Such forces depend on the optical field distributions and optical properties of the binding partners or binding partner-moiety complexes. In other examples, the built-in structures are the electro-optical elements and arrays that are incorporated on a chip and the external structures are electrical signal sources (e.g., a DC current source). When the electrical signals from the external electrical signal sources are applied to the built-in electro-optical elements and arrays, light is produced from these elements and arrays and optical fields are generated in the regions around the chip. When the binding partner or binding partner-moiety complexes are subjected to optical fields, optical radiation forces acting on the binding partners or binding partner-moiety complexes are produced. Such forces depend on the optical field distributions and optical properties of the binding partners or binding partner-moiety complexes.

For the case of manipulation force being mechanical force, the built-in structures may be the electromechanical elements/devices that are incorporated on a chip and the external structures are electrical signal sources (e.g., a DC current source). The electromechanical devices may be a microfabricated pump that can generate pressures to pump fluids. When the appropriately designed electromechanical elements/devices are energized by the electrical signal sources, mechanical forces exerting on the fluid that is introduced to the spaces around the chip (e.g., on the chip) are generated. Thus, the binding partner or binding partner-moiety complexes in the fluid will experience mechanical forces. The forces on binding partner or binding partner-moiety complexes depend on the mechanical forces on the fluid and depend on the size, composition and geometry of the binding partners or binding partner-moiety complexes.

G. Exemplary Uses of the Present Methods

The present methods are generally applicable to microfluidic devices and systems, i.e., the use of microscale devices, e.g., the characteristic dimension of basic structural elements is in the range between less than 1 micron to cm scale, for fluidic manipulation and process, typically for performing specific biological, biochemical or chemical reactions and procedures. The specific areas include, but not limited to, biochips, i.e., microchips for biologically related reactions and processes, chemchips, i.e., microchips for chemical reactions, or a combination thereof. In microfluidic devices and systems, manipulation and transportation of the moieties, e.g., molecules, is often a basic requirement. For example, an ideal biochip-based analytical apparatus may involve steps such as blood cell processing and isolation, target cell lysis and mRNA extraction, mRNA transportation, reverse transcription, PCR amplification and finally target DNA molecule detection. The apparatus may include a number of biochip-based, interconnected reaction chambers. The molecules processed over one chip may need to be sent over to a second chip, and the handling, processing, manipulation and directed movement of target molecules is a basic step for such applications. By coupling molecules onto the binding partners, the present methods can be used to perform multiple bioprocessing steps in such multiple, biochip-based, interconnected reaction chambers. For example, one type of beads may be used as binding partners for isolate target cells from blood under appropriate physical forces (e.g., dielectrophoresis force). After target cell-binding partner complexes are isolated from the blood cell mixture, the cells are lysed. Then, the binding partner beads for binding the cells are removed, and a second type of binding partners (a different type of beads) is introduced for mRNA molecules in the cell lysate to specifically bind to the surfaces of the binding partners to form mRNA-binding partner complexes. The mRNA-binding partner complexes are then manipulated and transported to a different chamber where reverse transcription reactions may be performed.

The present methods can be used for any type of manipulations. Non-limiting examples of the manipulations include transportation, focusing, enrichment, concentration, aggregation, trapping, repulsion, levitation, separation, isolation or linear or other directed motion of the moieties. The following description illustrates the exemplary uses of the present methods. The first example relates to "separation of target molecules" over a biochip. The steps may include the following: 1) a molecule mixture that contains two or more-than-two types of molecules is introduced into a biochip-based reaction chamber and of all the molecule types in the mixture, there is a target, molecule type; 2) add microbeads (binding partners), onto which the target molecules can bind, into the reaction chamber; 3) incubate the microbeads with the molecule mixture so that the target molecules bind specifically to microbeads, and if required, appropriate temperature is maintained and mixing mechanism may be applied to mix the microbeads with the molecules; 4) apply certain types of physical forces to harvest microbeads, and if the microbeads are paramagnetic, magnetic fields may be applied to these microbeads by turning on microelectromagnetic array that is fabricated into biochip and the microbeads are attracted and trapped to the microelectromagnets; 5) an external fluid flow force may be applied to the fluid in the chamber to flush out the buffer while simultaneously the microelectromagnets retain and hold microbeads; and 6) microelectromagnets may be turned off to release microbeads from their holding locations, and optionally, the target molecules may then be released from microparticle surfaces and are separated for further uses.

The second example relates to "transportation of target molecules" over certain distance on a biochip. The steps involved are somewhat similar to the first example, except that during the manipulation step (4), physical forces are applied to transport microparticles. The examples of physical forces for such transportation may be traveling-wave dielectrophoresis, electrophoresis and dielectrophoresis. Furthermore, there is no need for steps (5) and (6) in this example. The third example relates to "focusing of target molecules" onto certain regions on a biochip. The steps involved are similar to the second example, except that during the manipulation step (4), physical forces are applied to direct and focus microparticles on specific regions. The examples of physical forces for such transportation may be dielectrophoresis, magnetophoresis, and traveling-wave dielectrophoresis. After microparticles are focused onto such regions, the molecules linked on the microparticles may be detached and further processed for participating in certain biochemical reactions.

Various manipulations, such as levitation, trapping, transportation, circulation and linear motion can be achieved using the present methods with a suitable force for example, dielectrophoresis (DEP) force (Wang, et al., *Biochim. Biophys. Acta.* 1243:185–194 (1995)). Several electrode configurations designed to produce electric fields capable of inducing DEP and traveling wave DEP forces for the purpose of manipulating particles can be used (see e.g., Wang, et al., *IEEE Trans. Ind. Appl.* 33:660–669 (1997)). The types of manipulations disclosed in the following references can also be achieved using the present methods: Wang, et al., *Biophys. J.* 72:1887–1899 (1997) (concentration, isolation and separation using spiral electrodes); Wang, et al., *Biophys. J.* 74:2689–2701 (1998), Huang, et al., *Biophys. J.* 73:1118–1129 (1997) and Yang, et al., *Anal. Chem.* 71(5): 911–918 (1999) (levitation, repulsion from electrodes and separation by dielectrophoretic field-flow-fractionation); Gascoyne, et al., *IEEE Trans. Ind. Apps.* 33(3):670–678 (1997), Becker, et al., *Proc. Natl. Acad. Sci. USA* 92:860–864 (1995) and Becker, et al., *J. Phys. D: Appl. Phys.* 27:2659–2662 (1994) (trapping, repulsion, redistribution and separation, separation by dielectrophoretic migration, separation by dielectrophoresis retention); Huang, et al., *J. Phys. D: Appl. Phys.* 26:1528–1535 (1993) (transportation and trapping by traveling-wave-dielectrophoresis); and Wang, et al., *J. Phys. D: Appl. Phys.* 26:1278–1285 (1993) (trapping, separation and repulsion, separation by dielectrophoretic migration). The target objects for manipulation in these references are bioparticles such as cells and surface-coated beads. The manipulation steps and devices can also be applied for manipulating binding partners, moiety-binding partner complexes as described in this invention.

Other examples of manipulation that are reported in the literature and may be adapted for manipulating moieties using the present methods with a suitable force, preferably dielectrophoresis (DEP) force, include: separation of bacteria from blood cells, and of different types of microorganisms (Hawkes, et al., *Microbios.* 73:81–86 (1993); and Cheng, et al., *Nat. Biotech.* 16:547–546 (1998)); enriching CD34+ stem cells from blood (Stephens, et al., *Bone Marrow Transplantation* 18:777–782 (1996)); DEP collection of viral particles, sub-micron beads, biomolecules (Washizu, et al., *IEEE Trans. Ind. Appl.* 30:835–843 (1994); Green and Morgan, *J. Phys. D: Appl. Phys.* 30:L41–L44 (1997); Hughes, et al., *Biochim. Biophys. Acta.* 1425:119–126 (1998); and Morgan, et al., *Biophys J.* 77:516–525 (1999)); DEP levitation for cell characterization (Fuhr, et al., *Biochim. Biophys. Acta.* 1108:215–233 (1992)); single-particle homogeneous manipulation (Washizu, et al., *IEEE Trans. Ind. Appl.* 26:352–358 (1990); Fiedler, et al., *Anal. Chem.* 70:1909–1915 (1998); and Müller, et al., *Biosensors and Bioelectronics* 14:247–256 (1999)); dielectrophoretic field cages (Schnelle, et al., *Biochim. Biophys. Acta.* 1157:127–140 (1993); Fiedler, et al. (1995); Fuhr, et al. (1995a); Fiedler, et al. (1998); Müller, et al. (1999)); traveling-wave DEP manipulation of cells with linear electrode arrays (Hagedorn, et al., *Electrophoresis* 13:49–54 (1992); Fuhr, et al., *Sensors and Actuators A:* 41:230–239 (1994); and Morgan, et al., *J. Micromech. Microeng.* 7:65–70 (1997)).

In addition to the examples of microparticle or molecule manipulation described above, many other on-chip methods or approaches may be used for manipulating microparticles. For example, the dielectrophoretic field cages constructed using three-dimensional electrode elements may be used to trap, position, and handle and manipulate molecules and molecule-microparticle complexes. Indeed, the electrode structures and the processes for manipulating microparticles described in the following articles may all be used for manipulating molecule-microparticle complexes: "Three-dimensional electric field traps for manipulation of cells—calculation and experimental verification by Schnelle T., et al., in *Biochim. Biophys. Acta. Volume* 1157, 1993, pages 127–140", "A 3-D microelectrode system for handling and caging single cells and particles, by Müller, T., et al., in *Biosensors and Bioelectronics, Volume* 14, pages 247–256, 1999"; "Dielectrophoretic field cages: technique for cell, virus and macromolecule handling, by Fuhr, G., et al., in *Cellular Engineering. Autumn: pages* 47–57, 1995"; "Electrocasting—formation and structuring of suspended microbodies using A.C. generated field cages, by Fiedler S. et al., in. *Microsystem Technologies.* Volume 2: pages 1–7, 1995"; "Dielectrophoretic sorting of particles and cells in a microsystem, by Fiedler, S., et al., in *Anal. Chem.* Volume 70: pages 1909–1915, 1998".

The following further examples relate to the manipulation of nucleic acid molecules and blood cells:

1. Isolation of mRNA Molecules

A fluidic chamber comprising a chip on the bottom surface is used. A microelectromagnetic array is fabricated on the chip. The units within the microelectromagnetic array can be turned on or off through switching methods between the chip and external electrical signal sources. The magnetic fields can be further increased or decreased by varying magnitudes of external electrical signals. Paramagnetic microparticles, e.g., 0.5–5 micron, are used. The polyT (T-T-T-T . . . ) molecules are covalently linked to the surfaces of the magnetic particles. When the particles are incubated with a solution containing mRNA molecules, e.g., cell lysate, or tissue lysate, poly A residues at the 3' end of most mature mRNAs and the polyT molecules on the paramagnetic microparticles will be bound by base-pairing mechanism. The incubation solutions are introduced into the microfluidic chamber by introducing mRNA and beads into the chamber through different inlets and the incubation process occurs in the chamber. By applying electrical current sources to microelectromagnets on the chip surfaces, magnetic fields are turned on at certain locations of the chip. Magnetic particles may be concentrated or directed or focused towards these locations regions on the chip, i.e., concentrating or transporting magnetic particles. Thus, mRNAs are concentrated to these regions. With the magnetic fields on, washing buffer may be introduced so that only magnetic particles and their associated mRNAs are retained on the chip. Other molecules in the solution will be washed away. mRNAs may then be eluted from the microparticles in DEPC-treated water (High pH) or by raising temperature and can be used in further reactions such as RT-PCR, in vitro transcription, etc.

2. Isolation of DNA Molecules

This example is similar to the above example (1). Here, the surfaces of the magnetic particles may be carboxyl-terminated, or siliconized. The surfaces of the magnetic particles may be modified in other ways so that DNA molecules may bind to the particles. During the incubation process, DNA molecules from the solution non-specifically bind to paramagnetic particles under high concentration of salt, e.g., 2–3 M guanidine HCl. Once bound, the DNA is stable and may be easily eluted from the paramagnetic particles in various aqueous, low-salt, buffers, such as Tris. Similar process to the above example is used for directing, concentrating and focusing magnetic particles on target regions by applying electrical current to the microelectromagnetic units on the chip surface.

3. Transportation of mRNA or DNA Molecules

The fluidic chamber similar to the above examples is constructed. The chip on the chamber bottom contains a electrode array that can transport particles by applying phase-sequenced signals to the electrode array. A traveling-wave electrical field is generated in the chamber and, when particles are introduced into the chamber, traveling-wave dielectrophoresis forces are generated on the particles to move and transport them. Thus, after mRNA (or DNA) molecules are bound to microparticles, molecule-microparticle complexes are transported along certain paths to specified locations on biochip surfaces. Thus, mRNA or DNA molecules are transported.

The above examples employ microparticles that are manipulatable by traveling-wave dielectrophoresis because of their dielectric properties. Other particles may be used if acoustic forces or magnetic forces are exploited for similar manipulations.

4. Separation of White Blood Cells from a Whole Human Blood 4.1. Linking or Coupling Target White Blood Cells to Magnetic Bead Surfaces We performed experiments to demonstrate the separation of white blood cells from a whole human blood using the methods in this invention. The paramagnetic beads supplied from Dynal (4.5 micron M-450 beads) were used. These beads were coated with either CD15 or CD45 antibodies and were used to bind CD15 positive and CD45 positive human leukocytes. First, these two types of the paramagnetic beads were mixed together by transferring 12.5 microliter bead suspension (having $5 \times 10^6$ beads) of each of the two type of beads supplied from Dynal. The bead mixtures were then washed three times in a PBS solution (phosphate-buffered-saline). The beads were then harvested and mixed with 100 microliter whole human blood in an Eppendorf tube. The mixture was incubated at 4° C. on an apparatus that allows gentle tilting and rotation for ten minutes. This caused that white blood cells were bound to the paramagnetic beads. Typically, one white blood cell was bound to a magnetic bead or a couple of magnetic beads.

4.2. Introducing the Mixture of Magnetic Beads and Blood into a Chamber Comprising an Electromagnetic Chip on the Bottom A circular, plastic disc spacer that had been cut in the center was glued to an electromagnetic chip. The center-cut hole was round in the shape and formed the chamber volume. The electromagnetic chip had microfabricated electromagnetic units that comprised magnetic cores wrapped with electrical wire coils. When an electrical current up to four hundred microamperes was applied to an electrical coil, the magnetic field was induced in the vicinities of the magnetic unit. The white blood cell/paramagnetic bead complexes were then attracted to the regions of maximum magnetic field strength. Several minutes after electrical current was applied, all the magnetic beads and magnetic bead-coupled white-blood-cell complexes were attracted at the poles of the magnetic units. A fluid flow was then introduced in the chamber to wash off the red blood cells that were not attached to magnetic beads. Thus, this process left behind white-blood-cell/magnetic bead complexes in the chamber. Depending on the applications, various methods may then be applied to detach white blood cells from magnetic beads.

5. Isolation and Transportation of Protein Molecules

A fluidic chamber comprising a chip on the bottom surface is used. A traveling-wave dielectrophoresis array as shown in FIG. 5 is fabricated on the chip. The electrode array can be energized to produce traveling-wave electric filed to induce traveling wave dielectrophoresis forces on particles in the vicinity of array. Polystyrene beads, e.g., 2–20 micron, are used. The antibodies that are specific against target protein molecules are linked to the surfaces of the beads. The bead suspension and a molecule mixture containing target protein molecules will be introduced to the chamber through different inlets. The incubation process occurs in the chamber to allow target proteins to bind to the bead surfaces. By applying appropriate electrical signals to the electrode array, protein-bead complexes may be directed and trapped on the electrode array. With the electric field on, washing buffer may be introduced so that only protein-bead complexes are retained on the chip. Other molecules in the solution will be washed away. A different electrical signal may then be applied to transport the protein-bead complexes by using traveling wave dielectrophoresis forces. The proteins may then be detected on the bead, or released from the bead for further analysis.

H. Variations of the Manipulation Methods, Kits and Uses Thereof

The present manipulation methods can have infinite variations and can be used for many suitable purposes such as isolation, preparation, detection, diagnosis, prognosis, monitoring and screening, etc.

In one specific embodiment, the moiety to be manipulated is a cell and the cell specifically binds to the surfaces of a binding partner (e.g. magnetic beads) that is modified to contain specific antibodies against the cells. In this way, any target cells can be manipulated using binding partners with requisite specific antibody(ies).

In another specific embodiment, the moiety to be manipulated is substantially coupled onto surface of the binding partner to increase the manipulation efficiency. Preferably, the moiety to be manipulated is completely coupled onto surface of the binding partner. For example, if mRNA is the moiety to be manipulated, the mRNA molecules should substantially bind to their binding partners, e.g., microparticles. Depending on the specific applications, the percentage of mRNA molecules that should be coupled to the microparticles may be different. For example, in some applications, "the mRNA molecules substantially binding to their binding partners" means that about 5% of mRNA molecules should be coupled to the binding partners when 5% of mRNA molecules is a sufficient quantity for the follow-up manipulations and assays. In other applications, "substantially binding to their binding partners" means that about 80% of mRNA molecules should be coupled to the binding partners. If the binding partners are microparticles, the mRNA molecules that "substantially bind to the binding partners" may bind to one single microparticle, or may bind to multiple or many microparticles. Preferably, the mRNA molecules are completely bind to such microparticles, although not necessarily to a single or single kind of microparticles.

Although the present method can be used to manipulate a single moiety at a time, the present method is preferably used to manipulate a plurality of moieties, whether sequentially or simultaneously, because the present method is easily amenable to automation. The plurality of moieties can be manipulated via a single binding partner or a plurality of binding partners. Preferably, the plurality of moieties is manipulated via a plurality of corresponding binding partners.

When a plurality of moieties is manipulated simultaneously, the present method can be used in large-scale detecting, monitoring or screening procedures, e.g., screening for drug or other desirable bioactive substances. For example, the method can be used in detecting or monitoring target cells' response, in terms of gene expression pattern and protein expression and/or localization pattern, to the treatment of drug candidates in drug screening or development procedures. In these procedures, the target cells can be first manipulated or isolated using the present method with a first type of binding partner (e.g., magnetic beads that specifically recognize and bind to the target cells). Then, mRNAs and/or proteins can be manipulated and/or isolated from the isolated target cells using the present methods. Here certain treatment of the target cells may first be performed to obtain the mRNAs and proteins from the target cells. The target cells may be lysed so the cell lysate solutions contain many biomolecules from the cells, e.g., proteins, RNAs, DNAs, lipids, etc. Then a second type of binding partner for the target proteins and a third type of binding partner for the mRNAs would be used to selectively manipulate proteins and mRNAs. For example, both types of binding partners may be dielectric microparticles but possess different dielectric properties so that one type may exhibit positive dielectrophoresis and the other type under same conditions experience negative dielectrophoresis. These types of binding partners may be separated and selectively manipulated using certain dielectrophoretic manipulation method (e.g., the methods described in section G) after they have the proteins and mRNA molecules bound to them. The selectively manipulated mRNAs and proteins may then be further analyzed and assayed to obtain various information such as their quantities and activities. The mRNA and/or protein expression patterns thus obtained in the presence of the drug candidate treatment can be compared to that in the absence of the same treatment to assess the efficacy of the drug candidate.

The invention is also directed to a method for isolating an intracellular moiety from a target cell, which method comprises: a) coupling a target cell to be isolated from a biosample onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) obtaining an intracellular moiety from said isolated target cell; d) coupling said obtained intracellular moiety onto surface of a second binding partner of said intracellular moiety to form an intracellular moiety-binding partner complex; and e) isolating said intracellular moiety-binding partner complex with a physical force in a chip format, wherein said isolation is effected through a combination of a structure that is external to said chip and a structure that is built-in in said chip. The isolated intracellular moiety may be further detected, analyzed or assayed.

The intracellular moiety can be isolated from any target cell(s). Preferable, the intracellular moiety can be isolated from any target cell(s) in a biosample. Non-limiting examples of target cells include animal, plant, fungi, bacteria, recombinant or cultured cells, or cells derived from any particular tissues or organs. Preferably, the biosample is a body fluid, e.g., blood, urine, saliva, bone marrow, sperm or other ascitic fluids, and subfractions thereof, e.g., serum or plasma. Other non-fluidic biosamples, such as samples derived from solid tissues or organs, can be used in the present method. Preferably, the method is used in prognosis, diagnosis, drug screening or development, and the target cells are physiologically normal cells, physiologically abnormal cells, e.g., derived from patients with certain diseases, disorders or infections, or cells treated with drug candidate.

Any desired intracellular moiety can be isolated from the target cell(s). For example, cellular organelles, molecules or an aggregate or complex thereof can be isolated. Non-limiting examples of such cellular organelles include nucleus, mitochondria, chloroplasts, ribosomes, ERs, Golgi apparatuses, lysosomes, proteasomes, secretory vesicles, vacuoles or microsomes. Molecules can be inorganic molecules such as ions, organic molecules or a complex thereof. Non-limiting examples of ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of organic molecules include amino acids, peptides, proteins, nucleosides, nucleotides, oligonucleotides, nucleic acids, vitamins, monosaccharides, oligosaccharides, carbohydrates, lipids, enzymes, e.g., kinases, hormones, receptors, antigens, antibodies, molecules involved in signal transduction, or a complex thereof.

The intracellular moiety can be obtained from the target cell-binding complex by any methods known in the art. In some cases, the target cells may be lysed to obtain the intracellular moiety. However, in other cases, target cells can be made sufficiently permeable so that the intracellular moiety to be obtained can move across the cell membrane and/or wall, and complete cell lysis is not necessary. For example, if the intracellular moiety to be obtained resides in the periplasm of plant or bacterium cells, such intracellular moiety can be obtained by removing the cell walls while maintaining the plasma membrane intact. Similarly, if the intracellular moiety to be obtained resides in the cytoplasm, such intracellular moiety can be obtained by breaking the plasma membrane while maintaining other cellular organelles or structures intact. Other suitable variations are possible and are apparent to skilled artisans.

The method can comprise additional steps such as decoupling, transporting and/or detecting steps. In a specific embodiment, the method can further comprise a step of decoupling the first binding partner from the target cell-binding partner complex before obtaining the intracellular moiety from the isolated target cell.

In one specific embodiment, the method can further comprise a step of transporting the obtained intracellular moiety to a new location for coupling the obtained intracellular moiety onto surface of a second binding partner, or a step of transporting the intracellular moiety-binding partner complex to a new location for isolating the intracellular moiety-binding partner complex.

In another specific embodiment, the method can further comprise a step of detecting the isolated intracellular moiety-binding partner complex, or a step of transporting the isolated intracellular moiety-binding partner complex to a new location for detecting the intracellular moiety-binding partner complex, e.g., for detecting, monitoring, diagnosis, prognosis or other suitable purposes, and these analysis can be qualitative or quantitative. Depending on the types of the intracellular moiety, the analyses can be performed through many different means on a biochip or off a biochip. The detection method, the quantification method or the analysis method for the activity of the intracellular moieties are well known to those skilled in the art, e.g., in the field of cell biology, molecular biology, immunology and clinical chemistry. For example, reverse transcription of mRNAs to cDNAs followed by a cDNA amplification and hybridization detection may be used if the interested intracellular moiety is mRNAs. Various enzyme assay methods may be used for the enzymatic activity if the interested intracellular moiety is an enzyme molecule(s).

In still another specific embodiment, the method can further comprise a step of decoupling the intracellular moiety from the isolated intracellular moiety-binding partner complex and detecting the decoupled intracellular moiety, or a step of transporting the decoupled intracellular moiety to a new location for detecting the intracellular moiety, e.g., for detecting, monitoring, diagnosis, prognosis or other suitable purposes, and these analysis can be qualitative or quantitative.

The methods contemplated herein generally have two steps, isolating target cells and processing the isolated target cells for other purpose(s). Either of the two steps may be realized using the present invention. The target cells may be isolated by using the binding partners and manipulation of target cell-binding partner complexes in a chip format. The further processing of the isolated target cells may also involve the use of the binding partners and the manipulation of species in a chip format. Alternatively, both these two steps may be realized using the present invention. In some embodiments, the isolated target cells themselves can be analyzed, e.g., for detecting, monitoring or screening purposes. The analysis of the cells may be performed off-chip using the common methods used in cell biology, for example, the fluorescent-activated-cell-sorting analysis after labeling cells with certain fluorescent antibodies. The analysis of the cells may also be performed on a biochip that may be part of the biochip for cell isolation or may be a different chip that may be integrated with the cell isolation chip. The biochip analysis of the cells may be through various characterization approaches, for example, the dielectric characterization method of electrorotation may be used to measure cell dielectric properties. Or the electrochemical detection sensors or electrical impedance sensors may be used to analyzed the cell properties. Or a fluorescent analysis and detection may be used after labeling cells with certain fluorescent antibodies. Those skilled in the art of electrorotation, electrochemical detection and dielectric impedance detection may readily design appropriate chip structures and methods for these cell analyses.

In other embodiments, certain intracellular moieties can be isolated from the isolated target cells for further analysis. For example, DNA can be isolated for further hybridization, sequencing, mutant or polymorphism, e.g., single nucleotide polymorphism (SNP), analysis. mRNA can be isolated to assess gene expression. The isolation of DNA or mRNA in these examples may employ the method described in the present invention (e.g., see the examples described in Section G). The further analysis on isolated DNA molecules (e.g., by hybridization, sequencing, mutant or polymorphism, e.g., single nucleotide polymorphism (SNP), analysis) or on isolated mRNA molecules (e.g., by hybridization, reverse-transcription to cDNAs followed by amplification and detection/quantification) may be performed in a biochip format or off-a-biochip. Common molecular biology techniques employed in the lab for analyses of DNA and mRNA molecules may be used for such off-a-biochip analysis. Those skilled in molecular biology may choose appropriate protocols for such analyses. Various biochip-based methods may be used for the detection and analysis of DNA and RNA, for example, capillary-electrophoresis and electroosmosis driven separation of molecules, electronically-driven hybridization, and hybridization on a DNA array.

Proteins, e.g., kinases, enzymes, can be isolated for proteomics studies, e.g., assessing the level, post-translational modification, cellular location or function of the isolated proteins. The isolation of protein molecules may employ the method described in the present invention (e.g., see the examples described in Section G). Like the cases for isolated DNAs and mRNAs, the isolated protein molecules may be further analyzed either in a biochip-format or off-a-biochip using molecular biology, immunology, and protein-assay methods. Other small biomolecules (e.g., hormone and polysaccharides) can also be isolated and analyzed. Again, the isolation of small biomolecules may employ the method described in the present invention through the use of the binding partners and manipulation forces produced by a biochip. The isolated biomolecules may then be further analyzed either in a biochip-format or off-a-biochip format using molecular biology, protein assay and other biochemical assay methods.

The manipulation, isolation or analysis of the isolated target cells or intracellular moieties can be qualitative as well as quantitative. Although single target cell or intracellular moiety can be manipulated, isolated or analyzed, it is preferable that a plurality of target cells or intracellular moieties is manipulated, isolated or analyzed. For example, a plurality of target cells or intracellular moieties that are structurally connected, e.g., isolated from the same tissue or organ, functionally connected, e.g., involved in the same biological pathway, or both, e.g., involved in the same developmental stage, can be manipulated, isolated or analyzed by the present method. In the case of manipulating a plurality of intracellular moieties from the isolated target cells, a plurality of the binding partners may be used, each of which will be used for binding a single type of intracellular moiety. For example, magnetic beads may be used as a binding partner for binding mRNAs, simultaneously, surface coated polystyrene beads, glass beads, certain metallic beads may be used as binding partners for binding DNAs, proteins, and small biomolecules, respectively. These different binding partners may be selectively manipulated in a chip format, so that mRNAs, DNAs, proteins and small biomolecules may be separately manipulated and analyzed.

In one specific example, the invention is directed to a method for generating a cDNA library in a microfluidic application, which method comprises: a) coupling a target cell to be isolated onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) lysing said isolated target cell; d) decoupling and removing said first binding partner from said lysed target cell; e) coupling mRNA to be isolated from said lysed target cell onto surface of a second binding partner of said mRNA to form a mRNA-binding partner complex; f) isolating said mRNA-binding partner complex with a physical force in a chip format, wherein said isolation is effected through a combination of a structure that is external to said chip and a structure that is built-in in said chip, and g) transporting said isolated mRNA-binding partner complex to a different chamber and reverse transcribing said transported mRNA into a cDNA library. The target cell may be from many different sources, e.g., from a blood sample, or from other body fluids, a cultured cell sample.

In another specific example, the invention is directed to a method for studying expressions of certain genes in target cells in a microfluidic application, which method comprises: a) coupling a target cell to be isolated onto surface of a first binding partner of said target cell to form a target cell-binding partner complex; b) isolating said target cell-binding partner complex with a physical force in a chip format, wherein said isolation is effected through a combination of a structure that is external to said chip and a structure that is built-in in said chip, c) lysing said isolated target cell; d) decoupling and removing said first binding partner from said lysed target cell; e) coupling target mRNA molecules to be isolated from said lysed target cell onto surface of a second binding partner of said mRNA to form a mRNA-binding partner complex; f) isolating said mRNA-binding partner complex with a physical force in a chip format, wherein said isolation is effected through a combination of a structure that is external to said chip and a structure that is built-in in said chip; and g) quantifying the levels of isolated target mRNA molecules. The quantification of mRNA levels may be performed via various molecular biology methods. For example, mRNA may be first reverse-transcribed to cDNA, the cDNA may then be hybridized onto a DNA array on which the single stranded DNA that are complementary to the cDNA to be analyzed are immobilized. The target cells may be derived from various sources, e.g., from cells that have been exposed to drug molecules or candidate drug molecules.

In still another aspect, the invention is directed to a kit for manipulating a moiety in a microfluidic application, which kit comprises: a) a binding partner onto the surface of which a moiety to be manipulated can be coupled to form a moiety-binding partner complex; b) means for coupling said moiety onto the surface of said binding partner; and c) a chip on which said moiety-binding partner complex can be manipulated with a physical force that is effected through a combination of a structure that is external to said chip and a structure that is built-in in said chip. Preferably, the kit can further comprise instruction(s) for coupling the moiety onto the surface of the binding partner and/or manipulating the moiety-binding partner complex on the chip. Other suitable elements, such as means for decoupling said moiety from the surface of said binding partner, means for detecting or monitoring said manipulated moiety, means for transporting said manipulated moiety to a new location and means for collecting said manipulated moiety, can also be include in the kit.

I. Detailed Description of Methods and Apparatuses Illustrated in Drawings

FIG. 1 is a schematic drawing for an illustrative example of on-chip manipulation of molecules based on microparticles. This is a cross-sectional view of a biochip 10 on which a liquid suspension containing molecules 20 to be manipulated is placed. The biochip has a parallel electrode array 30 fabricated on its surface. The parallel electrode array is an array of linear line electrodes that are parallel to one another and are connected alternatively. A detailed description of the electrode shapes could be found in "Dielectrophoretic Manipulation of Particles by Wang et al, in *IEEE Transaction on Industry Applications, Vol.* 33, No. 3, May/June, 1997, pages 660–669". The chip could be fabricated from silicon, glass, plastic, ceramics, or other solid substrates. The substrate could be made of porous or non-porous materials. The electrode elements could be fabricated using photolithography on the substrate material and realized with thin metal films or other conductive layers. An example of electrode materials may be a 1000-Angstrom thick gold film over a 70-Angstrom thick chromium, as described in "Dielectrophoretic Manipulation of Particles by Wang et al, in *IEEE Transaction on Industry Applications, Vol.* 33, No. 3, May/June, 1997, pages 660–669". Those skilled in the art of microfabrication or micromachining could readily determine or choose or develop appropriate fabrication processes and materials for fabricating the electrode elements based on the required geometries and dimensions.

Figure 1A:
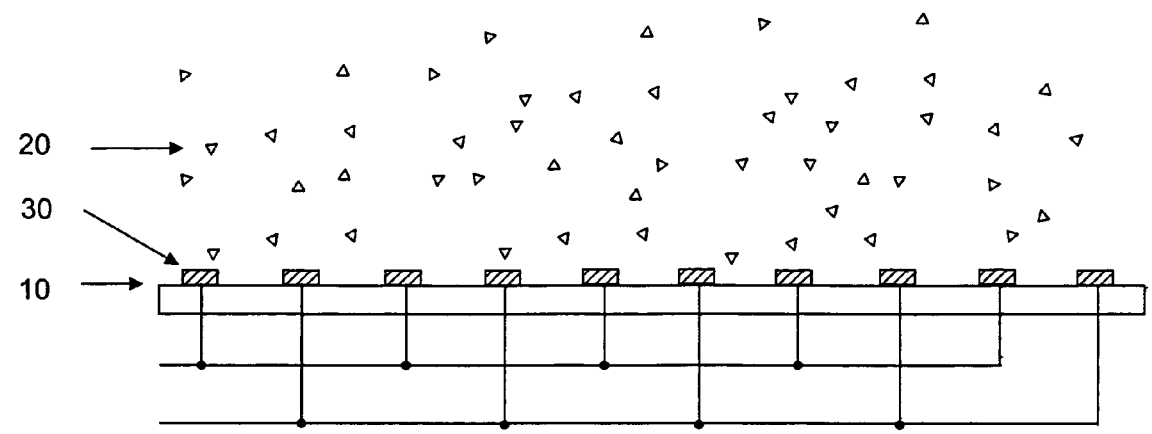
FIG. 1 depicts schematic drawing for illustrating the method of binding partner, e.g., micro-particle, based on-chip manipulation (levitation) of moieties to be manipulated, e.g., molecules.
Figure 1B:
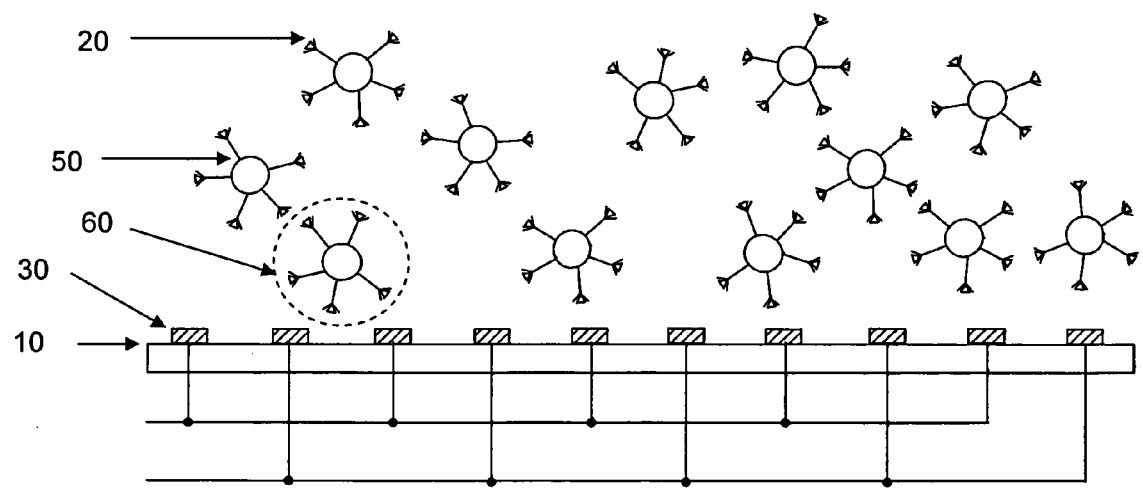
Figure 1C:
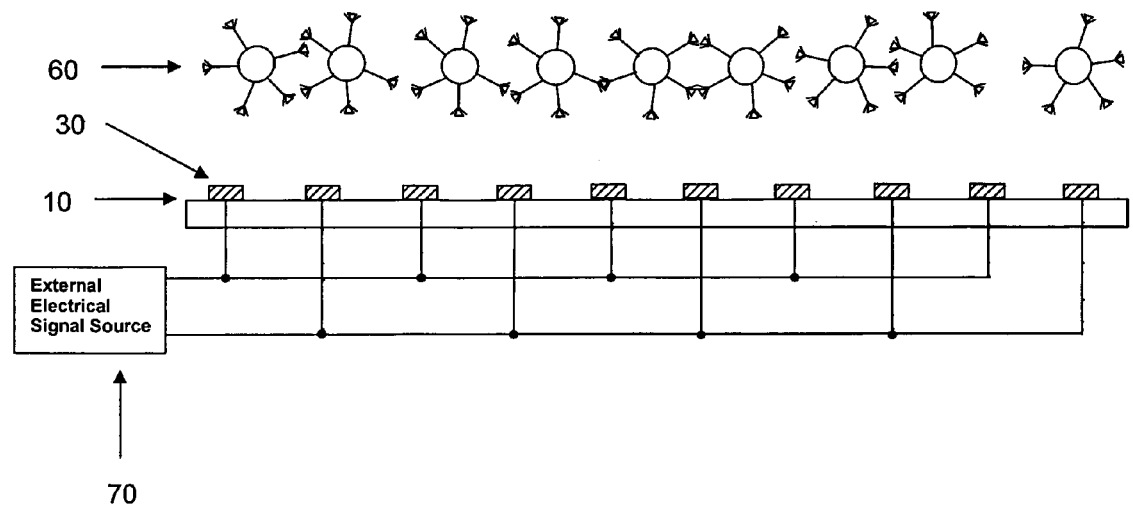

FIG. 1(A) shows that molecules 20 in a liquid solution are placed on the biochip (10) surface. FIG. 1(B) shows that molecules 20 are coupled into or linked to the surfaces of micro-particles 50 to form molecule-microparticle complexes 60. The linkage or coupling of molecules onto microparticle surfaces could be through various mechanisms. For example, for protein molecules to be manipulated, antibodies against such proteins could be first coupled to the microparticle surfaces. Then the coupling of proteins to the microparticle surfaces may be achieved through antibody-protein binding. FIG. 1(C) shows that upon the application of appropriate electrical signals from a signal source 70 to the electrode array 30, dielectrophoretic forces exerted on the microparticle-molecule complexes due to the non-uniform electrical fields generated in the spaces above the electrode array levitate molecule-microparticles to certain heights above the electrode plane. In this example, manipulation refers to levitation of molecules to certain heights above the chamber bottom surface. The waveform, frequency, magnitude and other properties of electrical signals may be chosen based on the dielectric and physical properties of microparticle-molecule complexes. The related theories in dielectrophoresis and dielectrophoretic levitation can be found in "Dielectrophoretic Manipulation of Particles by Wang et al, in *IEEE Transaction on Industry Applications, Vol.* 33, No. 3, May/June, 1997, pages 660–669" and "Introducing dielectrophoresis as a new force field for field-flow-fractionation by Huang et al, in *Biophysical Journal*, Volume 73, August 1997, page 1118–1129". Those who are skilled in dielectrophoresis and dielectrophoretic levitation of particles can readily choose or determine appropriate electrical signals used for such dielectrophoretic levitation.

To practice the molecule manipulation method shown in FIG. 1, a fluidic chamber may be constructed. FIG. 2 shows an example of such chambers. Here, the chamber comprises a biochip 10 on the bottom, a spacer 80 that is cut in the middle to define the chamber thickness, a top plate 90 that has input fluidic input port 100 and output port 110 incorporated on the plate 90. These three parts are bond together to form a fluidic chamber. For illustration, these three parts are not drawn together. The biochip 10 has parallel electrode elements 30 incorporated on its surface. For demonstration purpose, these electrode elements are the same as those in FIG. 1. Typically, for manipulating microparticles, these electrodes have dimensions for electrode width and gap between 1 micron and 5000 microns, and preferably, between 10 microns and 200 microns. Note for clarity, the electrodes are not drawn to scale. These parallel electrode elements can be used for a number of different manipulation applications such as levitation, trapping, immobilization and separation. In such cases, dielectrophoretic forces exerted on particles due to non-uniform electrical fields are utilized.

Figure 3A:
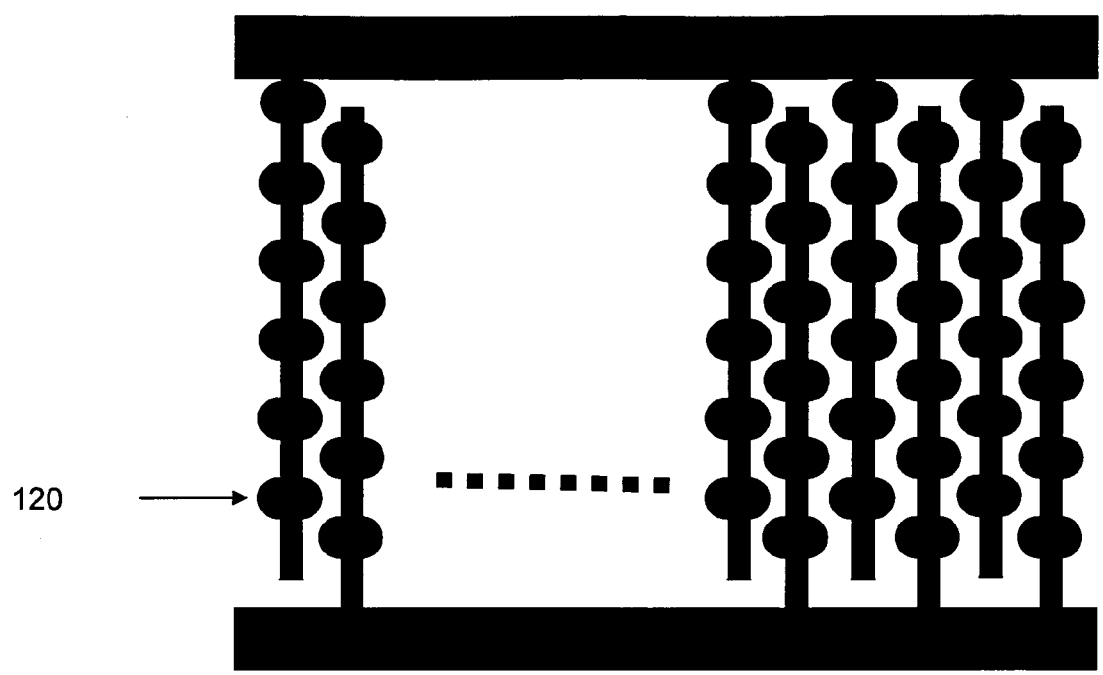
Figure 3B:
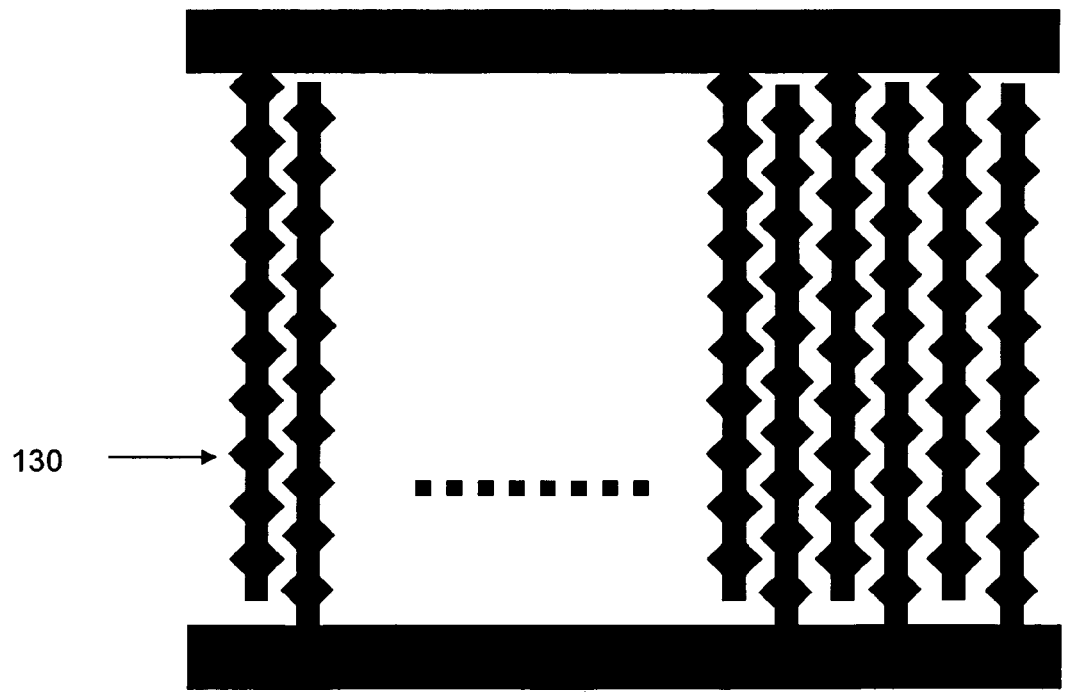

In addition to the parallel electrodes depicted in FIGS. 1 and 2, other electrode geometries could be used. For example, the interdigitated/castellated electrodes and polynomial electrodes described in "Dielectrophoretic Manipulation of Particles by Wang et al, in IEEE Transaction on Industry Applications, Vol. 33, No. 3, May/June, 1997, pages 660–669", interdigitated/semicircle-ended electrodes used in "Separation of human breast cancer cells from blood by differential dielectric affinity by Becker et al, in *Proc. Natl. Acad. Sci., Vol.*, 92, January 1995, pages 860–864", and other electrode geometries used in "Selective dielectrophoretic confinement of bioparticles in potential energy wells by Wang et al. in J. Phys. D: Appl. Phys., Volume 26, pages 1278–1285" could be used. FIGS. 3(A) and 3(B) show two other examples of interdigitated electrodes with different modified electrode edges, i.e., semicircle edges 120 in FIG. 3(A) and triangle edges 130 in FIG. 3(B). Again, these electrodes could be readily microfabricated on a substrate material using photolithography techniques.

FIG. 4 shows an example of fluidic chambers where acoustic forces are used to manipulate molecules and molecule-microparticle complexes. The chamber comprises a piezoelectric transducer element 140 at the chamber bottom, a spacer 150 that defines the chamber thickness and a top acoustic reflective plate 160. In operation, the spacer is bond together with the piezoelectric transducer. The liquid sample containing the molecules to be manipulated is introduced onto the chamber defined by the center cut at the spacer. Upon application of appropriate electrical signals 70 to the acoustic transducer 140, the acoustic wave produced on the transducer 140 will be emitted/transmitted/coupled into the liquid above the piezoelectric transducer. The acoustic wave travels to the top plate and is then partially reflected back into the liquid. The wave then follows similar "traveling" and "reflection" path at the bottom transducer surface. These transmitting and reflective acoustic waves in the chamber superimpose on each other, leading to a standing acoustic wave component and a travelling acoustic wave component. Such acoustic waves produce forces acting on the particles and molecules. For example, particles suspended in a liquid suspension can be subjected to radiation forces that drive particles to the pressure node or anti-node of the standing wave, depending on the acoustic properties of the particles in respect to those of the particle-suspending medium. The acoustic radiation forces exerted on molecules are in general quite small because of the molecules' small dimensions. Thus, molecules that can be first coupled onto the surfaces of the micro-particles may then subjected to acoustic manipulation forces. For example, direct acoustic manipulation of molecules in a standing acoustic wave may be difficult. Yet, choosing micro-particles with appropriate acoustic properties, molecules may then be indirectly transported or focused onto the layers in a standing acoustic wave, which correspond to either the node or anti-node of the pressure distribution of the standing wave. The detailed description of manipulation of microparticles in a standing acoustic wave may be found in various literatures including "Ultrasonic manipulation of particles and cells" by Coakley et al. *Bioseparation.* 1994. 4: 73–83", "Particle column formation in a stationary ultrasonic field" by Whitworth et al., *J. Accost. Soc. Am.* 1992. 91: 79–85", "Manipulation of particles in an acoustic field by Schram, C. J. *In Advances in Sonochemistry*; Mason, T. J., Ed.; JAI Press Ltd., London, 1991; Vol. 2: pp293–322", "Enhanced sedimentation of mammalian cells following acoustic aggregation by Kilburn et al., *Biotechnol. Bioeng.* 1989. 34: pp. 559–562".

Figure 5A:
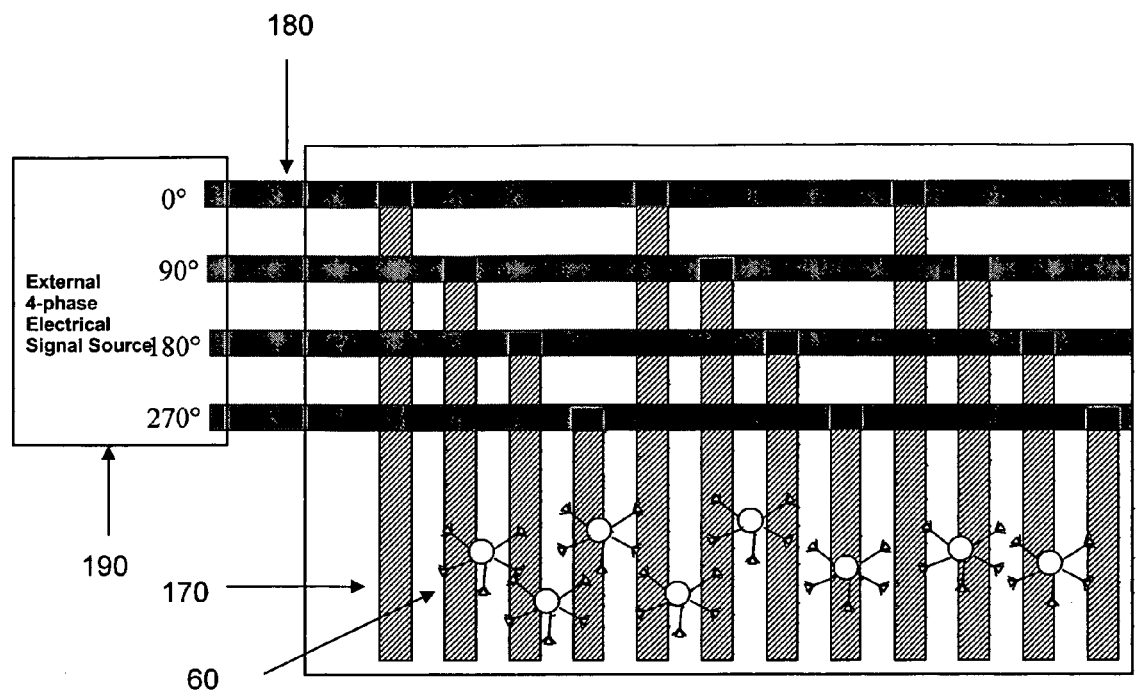
Figure 5B:
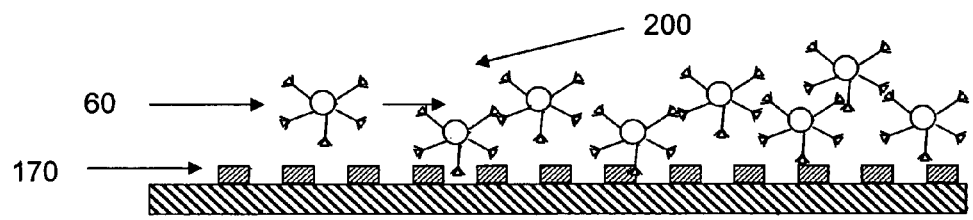
Figure 5C:
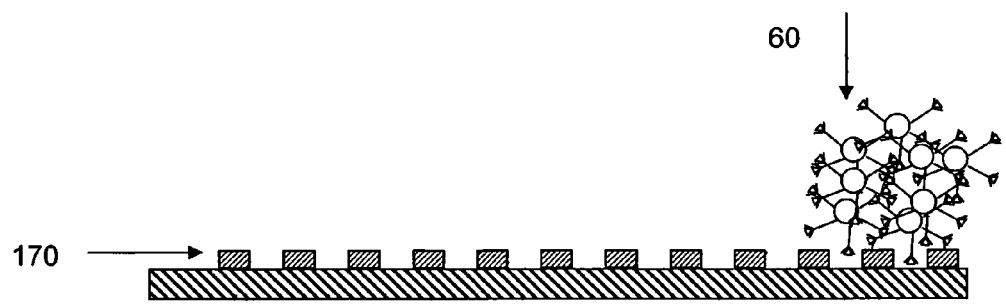

FIG. 5 shows an example of transporting molecule-microparticle complexes with traveling-wave-dielectrophoresis. FIGS. 5(A) and 5(B) show the top view and the cross-sectional view, respectively, of a linear electrode array. The linear electrode elements 170 are connected to a 4-phase signal source 190 through electrode bus 180 in such a way that every 4-electrode element is connected together. The phase sequential signals at phase 0, 90, 180 and 270 degrees addressed to the electrode elements produce a traveling wave electric field in the regions above the electrode elements 170. Molecule-microparticle complexes 60 in such a traveling field experience a dielectrophoretic force F 200 that is with or against the traveling direction of the traveling-wave field. Under a cross-sectional view, FIG. 5(C) shows that molecule-microparticle complexes 60 are transported to the end of the electrode array. By using traveling-wave-dielectrophoresis, molecules may be transported on a bio-chip in any direction or along any path dependent on the used electrode array configuration. Again, the general steps include first coupling molecules onto microparticle surfaces, then transporting molecule-microparticle complexes to desired locations, and then decoupling molecules from microparticles. The theories and practices of traveling-wave-dielectrophoresis may be found in the literatures, including "Dielectrophoretic Manipulation of Particles by Wang et al, in IEEE Transaction on Industry Applications, Vol. 33, No. 3, May/June, 1997, pages 660–669", "Electrokinetic behavior of colloidal particles in traveling electric fields: studies using yeast cells by Huang et al, in *J. Phys. D: Appl. Phys.*, Vol. 26, pages 1528–1535", "Positioning and manipulation of cells and microparticles using miniaturized electric field traps and traveling waves. By Fuhr et al., in Sensors and Materials. Vol. 7: pages 131–146", "Non-uniform Spatial Distributions of Both the Magnitude and Phase of AC Electric Fields determine Dielectrophoretic Forces by Wang et al., in *Biochim Biophys Acta Vol.* 1243, 1995, pages 185–194."

FIG. 6 shows an example of focusing, transporting, isolating and directing molecule-microparticle complexes through traveling-wave dielectrophoresis on a spiral electrode array 210. In this example, the spiral electrode array comprises four parallel, concentric, linear spiral elements. The spiral elements are energized sequentially with electrical signals of having phases of 0, 90, 180 and 270 degrees from an external signal generator 190. Under such signal application, a non-uniform, traveling wave electric field is produced in the spaces above the electrode array. Molecule-microparticle complexes 60 introduced in such a field may experience dielectrophoresis forces that has a vertical component in the direction normal to the electrode plane and a horizontal component that in the direction parallel to the electrode plane. The horizontal force component 220 arises mainly from traveling-wave-dielectrophoresis and may direct the molecule-microparticle complexes 60 either towards or away from the center of the spiral electrode array, depending on particle dielectric properties and the phase sequence of the applied electrical signals. The operational principle of the spiral electrode array and particle manipulation methods using the spiral electrode array may be found in "Dielectrophoretic manipulation of cells using spiral electrodes by Wang, X-B. et al., in *Biophys. J.* Volume 72, pages 1887–1899, 1997". Thus, one application of using the spiral electrode array is to concentrate or isolate target molecules from a molecule mixture to the center of the electrode array through binding target molecules on microparticles, transporting/manipulating microparticles to the center of the array and then decoupling the target molecules from microparticles.

Figure 7A:
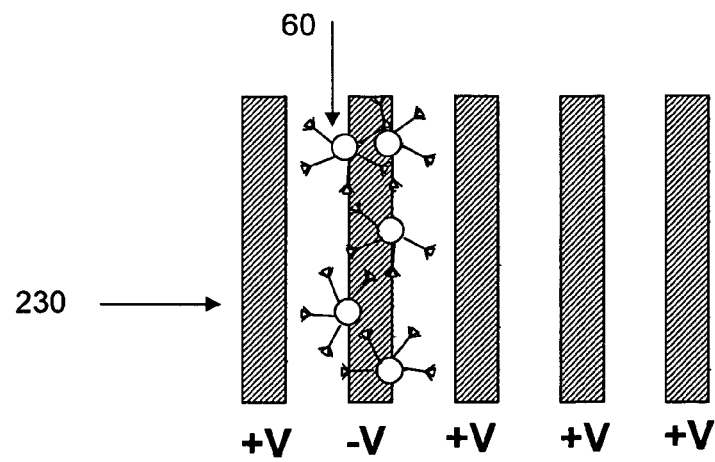
Figure 7B:
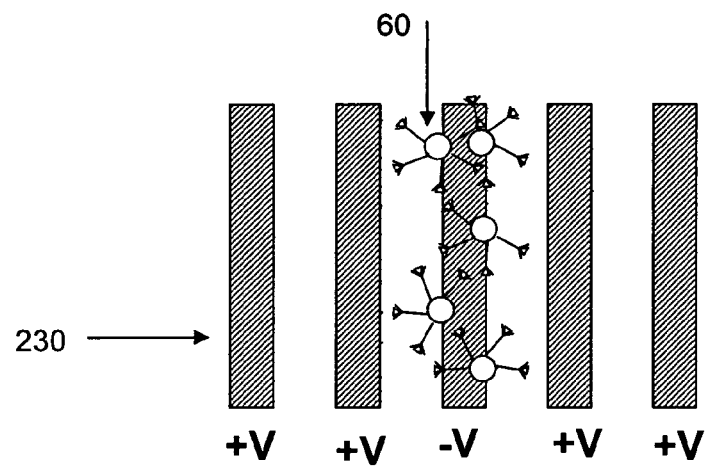
Figure 7C:
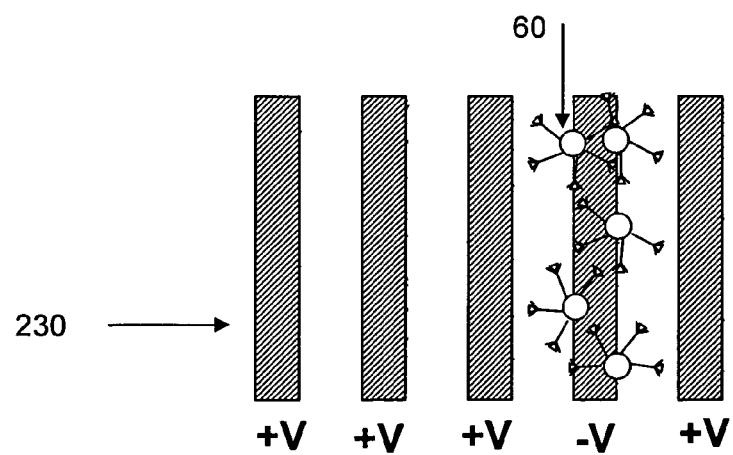

FIG. 7 shows an example of transporting molecule-microparticle complexes using traveling-wave electrophoresis induced by a parallel electrode array. In this case, microparticles are electrically charged and manipulation of particles is through the use of DC electrical fields for generating electrophoretic forces. In FIG. 7, microparticles are positively charged so that DC electrical field will drive the particles towards the electrodes that are negatively biased. FIG. 7(A) shows an intermediate state of particle transportation in which only one of the electrode elements is negatively biased and molecule-microparticle complexes 60 are collected at this electrode. All the other electrode elements are positively charged and microparticles are repelled from these electrodes. In FIG. 7(B), the electrical signal with the negative potential is then shifted to the next electrode whilst all other electrodes are positively biased. Thus, molecule-microparticle complexes are then directed and collected at the current negatively-biased electrode. In FIG. 7(C), the negative electrical signal shifted further to next electrode element and so did the molecule-microparticle complexes. In such a transportation case, the movement of molecule-microparticle is synchronized with the application of the negative electrical signals to the electrode elements. Because the motion of molecule-microparticles is based on electrophoresis and we applied electrical signals in a sequential fashion to induce an electrical field that travels, we thus refer this effect as traveling-wave electrophoresis. It is obvious to those who are skilled in understanding and practicing electrophoresis that various modifications to the present embodiment of traveling-wave electrophoresis could be realized. For example, if we choose negatively-charged microparticles, positively-applied electrical signals may be utilized to drive and transport particles. Utilizing this basic principle, transportation of molecules could be realized on a biochip by designing appropriate electrode arrays and applying suitable electric signals for specific types of molecules and microparticles.

Figure 8A:
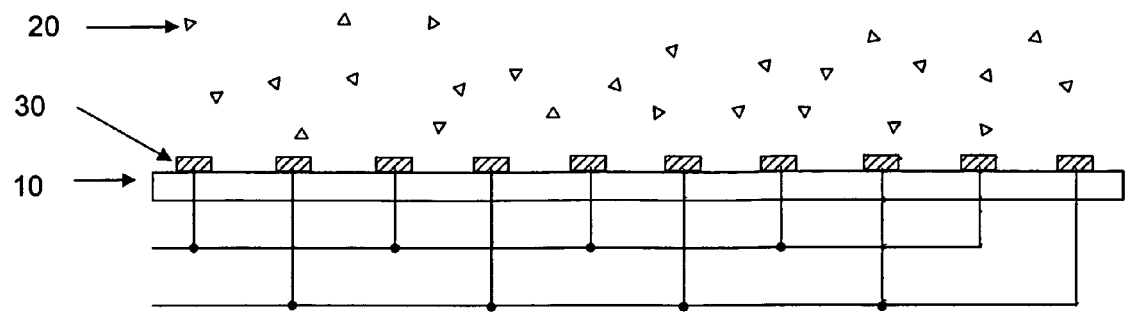
Figure 8B:
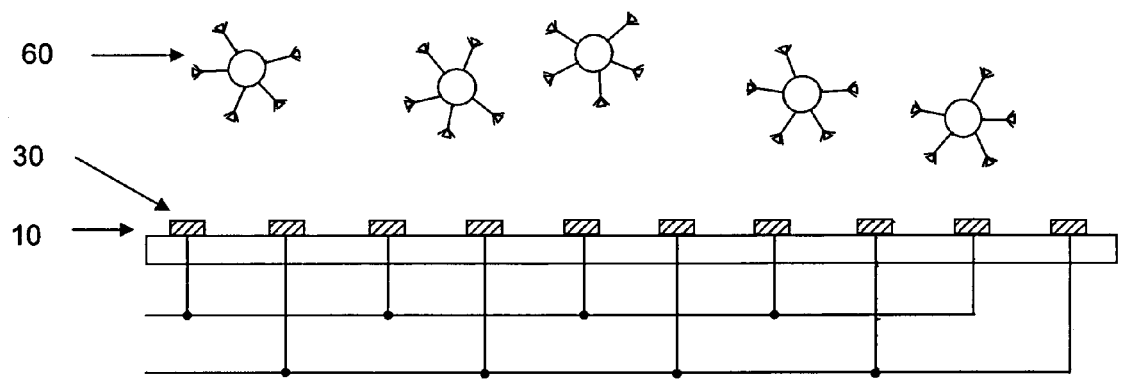
Figure 8C:
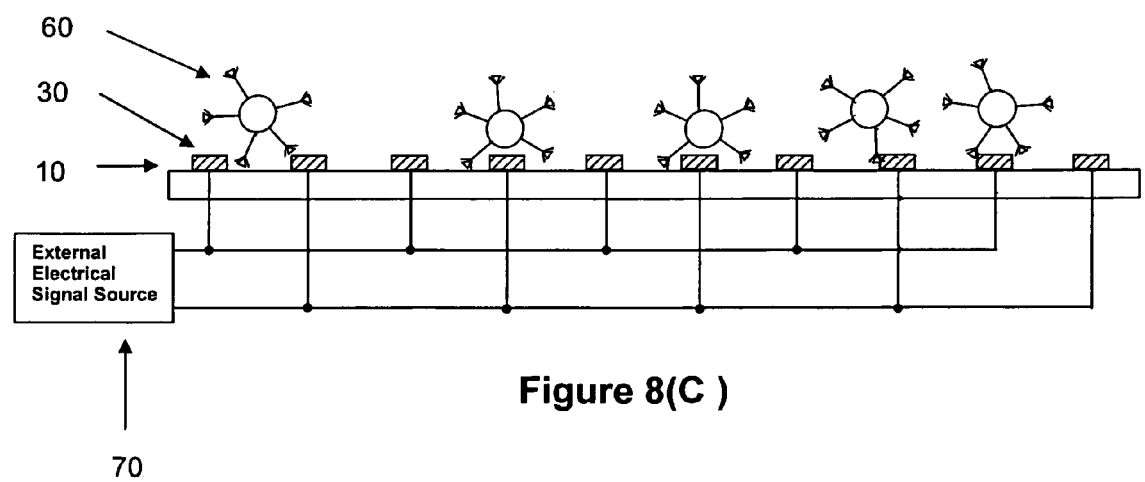

FIGS. 8(A)–(C) show an example of directing and transporting molecules to the surfaces of biochip 10 through dielectrophoresis. The biochip has a parallel electrode array 30 incorporated on the chip surface. FIG. 8(A) shows that molecules are suspended in a liquid solution that is introduced onto biochip. FIG. 8(B) shows that molecules are bound/linked onto the surfaces of microparticles to form the molecule-microparticle complexes 60. FIG. 8(C) shows that upon applying electrical signals at appropriate frequencies and magnitudes from signal source 70, molecule-microparticle complexes are focused or manipulated or brought down to the chip surface. The molecules may then be further disassociated from the microparticle surfaces and used for further biochemical reactions, e.g., reacting with molecules that are pre-immobilized on the chip surface. The fluidic chamber employed for manipulating molecules in this example is similar to that shown in FIG. 2. Details in using parallel electrode array for directing/manipulating microparticles to a biochip surface may be found in the article "Dielectrophoretic Manipulation of Particles by Wang et al, in IEEE Transaction on Industry Applications, Vol. 33, No. 3, May/June, 1997, pages 660–669."

Figure 9A:
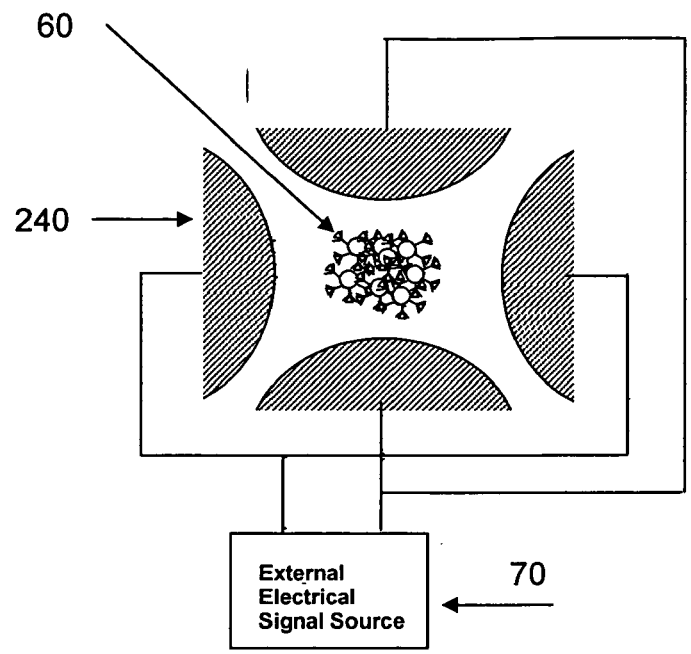
Figure 9B:
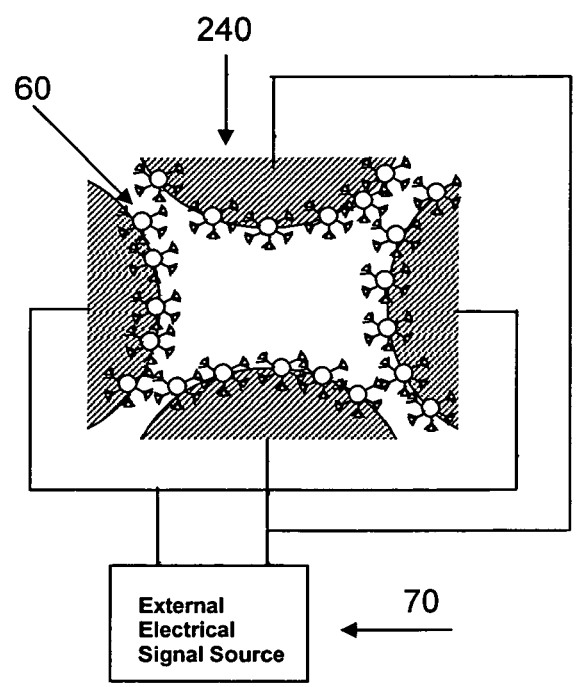

FIG. 9 shows the use of polynomial electrode array 240 for manipulating molecule-microparticle complexes. The detailed description for the geometry and operational principle of polynomial electrodes may be found in the article "Electrode design for negative dielectrophoresis, by Huang and Pethig, in *Meas. Sci. Technol. Volume* 2, 1991, pages 1142–1146." FIG. 9(A) shows that molecule-microparticle complexes 60 are concentrated into the central regions between the four electrode elements 240 up on applying appropriate electrical signals from signal source 70. FIG. 9(B) shows that molecule-microparticle complexes 60 are directed/manipulated to the edges of polynomial electrodes. The polynomial electrodes may be further employed for separating different types of microparticles or molecule-microparticle complexes. The examples of using polynomial electrodes for such separation may be found in the article "Selective dielectrophoretic confinement of bioparticles in potential energy wells, by Wang et al., in *J. Phys D: Appl Phys. Volume* 26, 1993, pages 1278–1285."

Figure 10A:
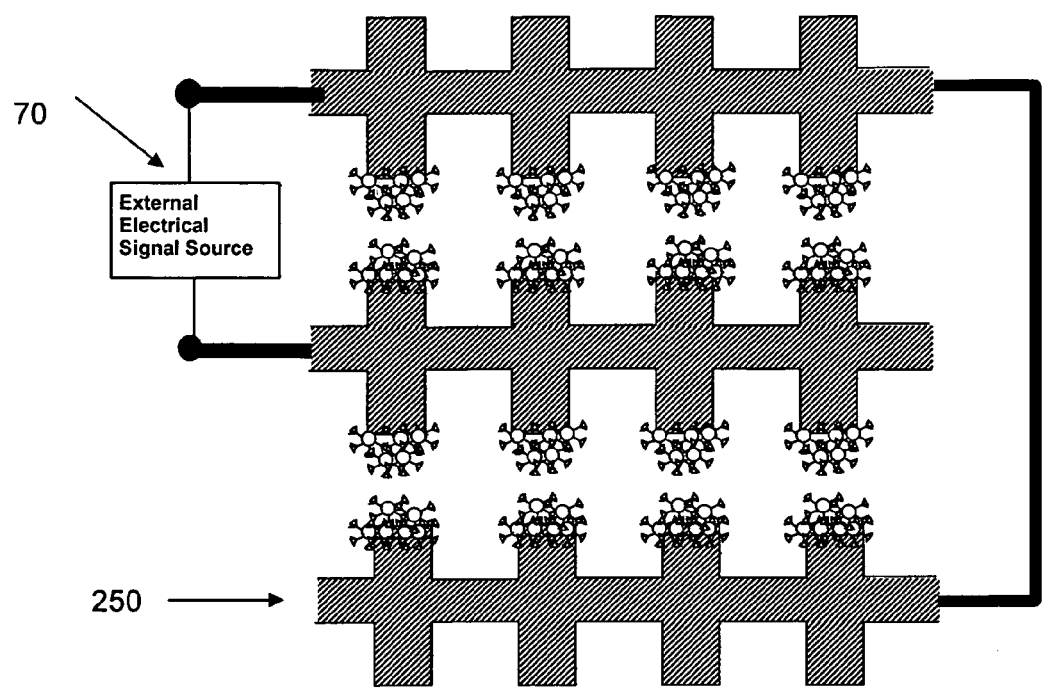
Figure 10B:
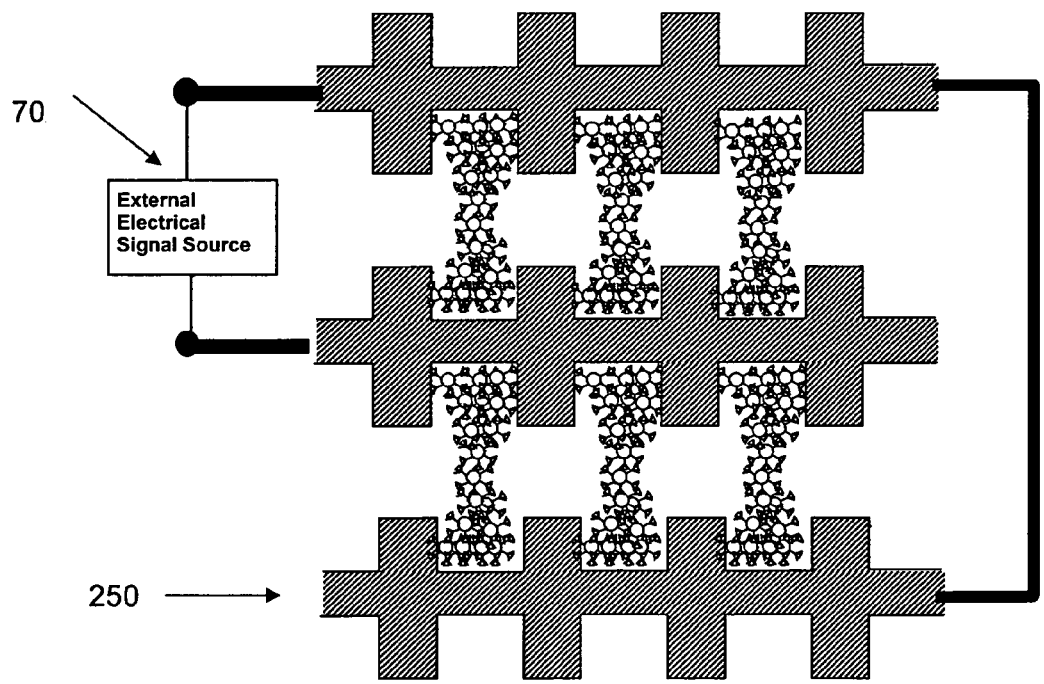
Figure 11A:
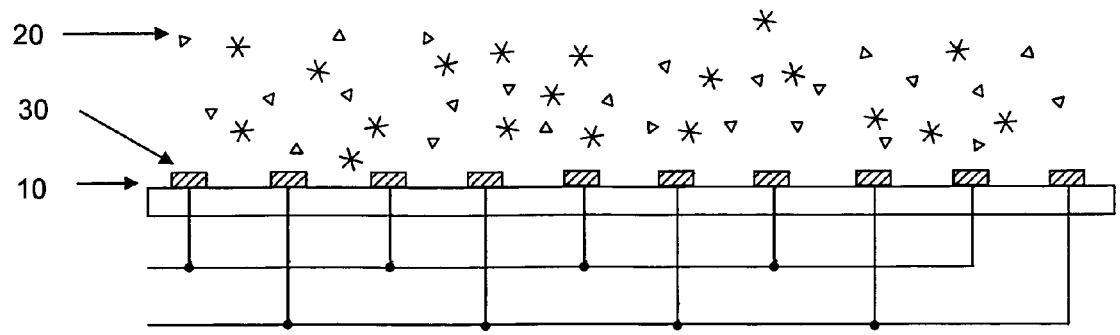
Figure 11B:
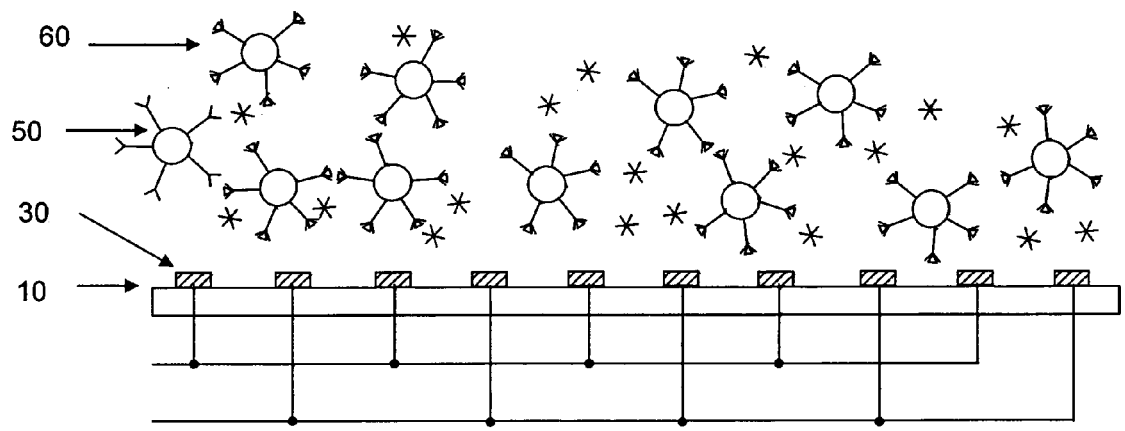
Figure 11C:
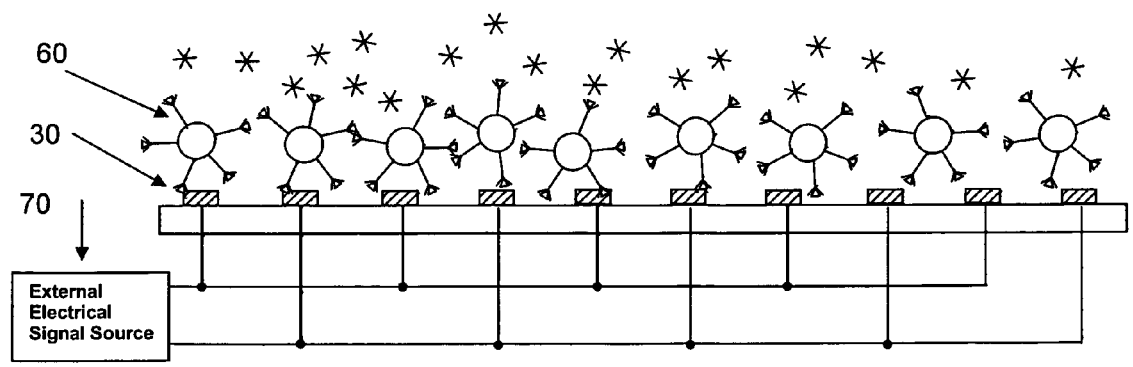
Figure 11D:
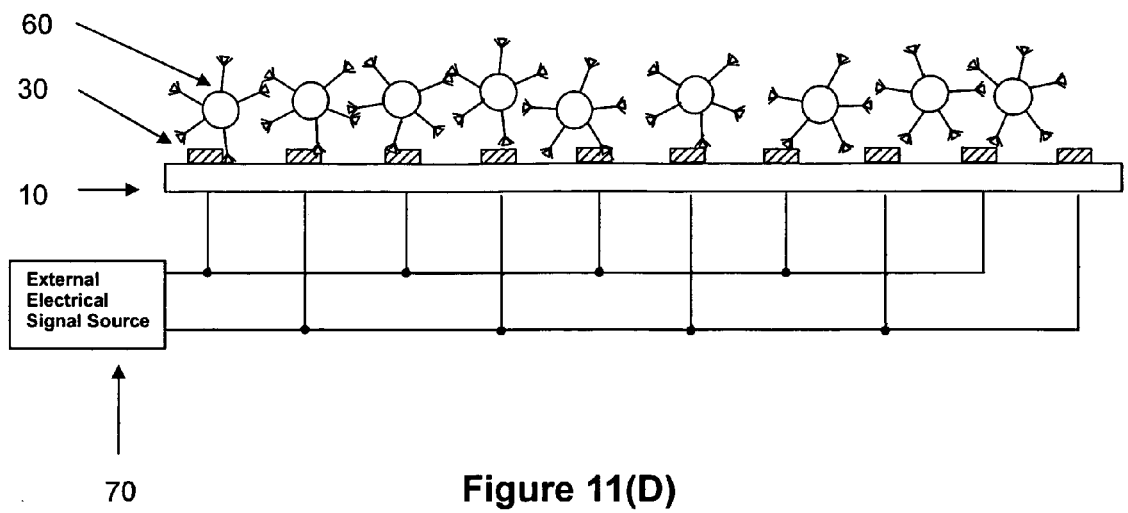
Figure 11E:
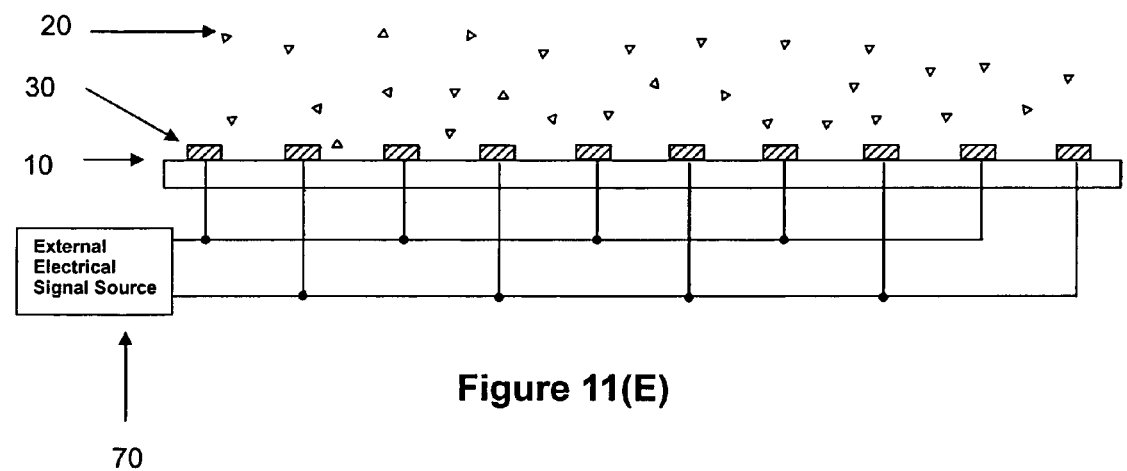
Figure 12A:
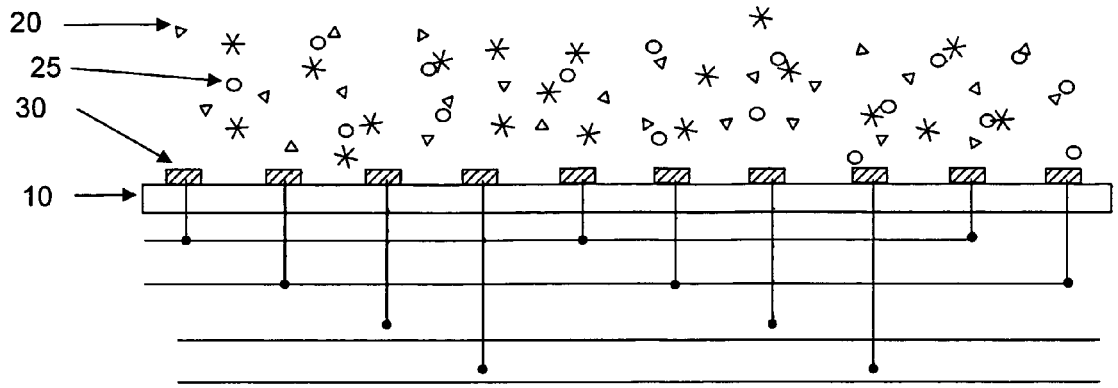
Figure 12B:
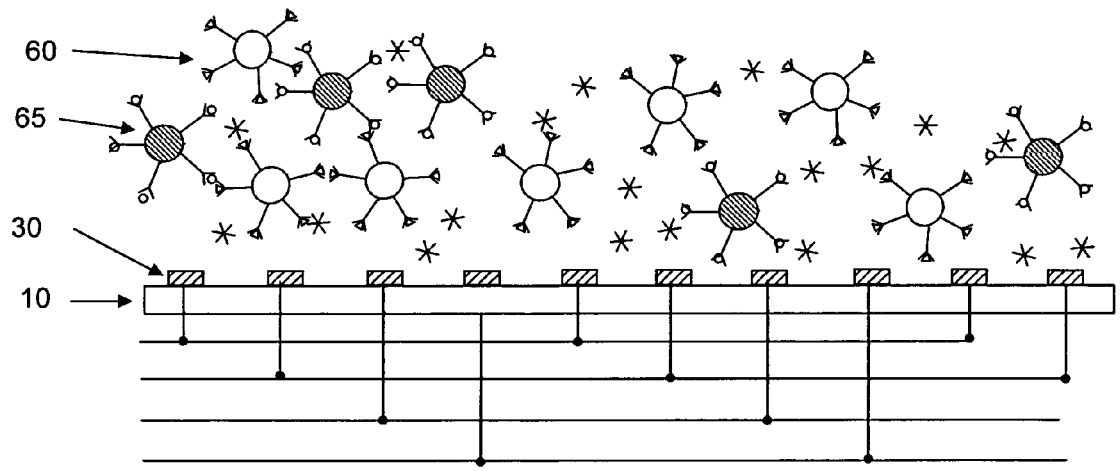
Figure 12C:
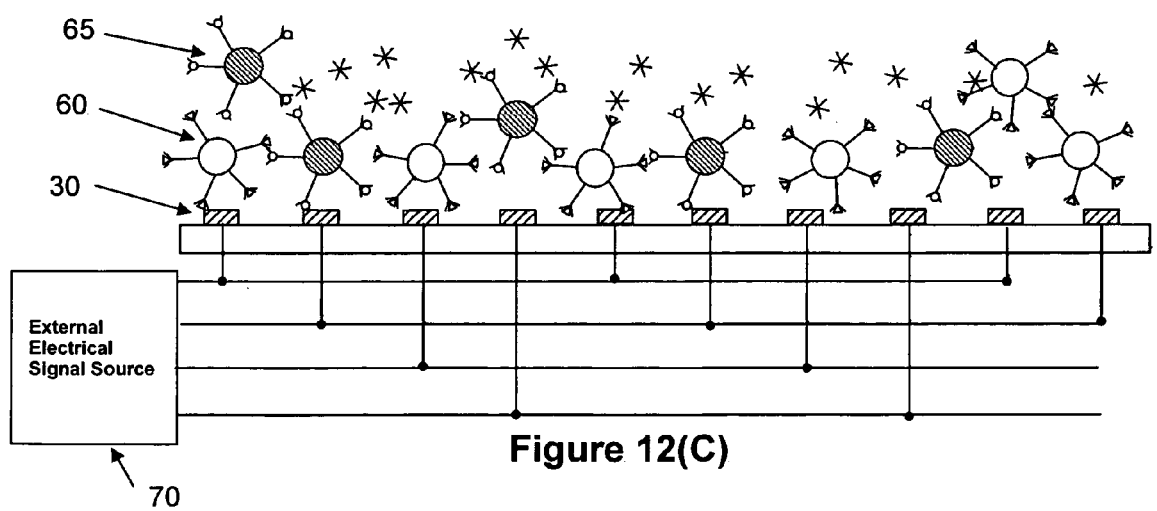
Figure 12D:
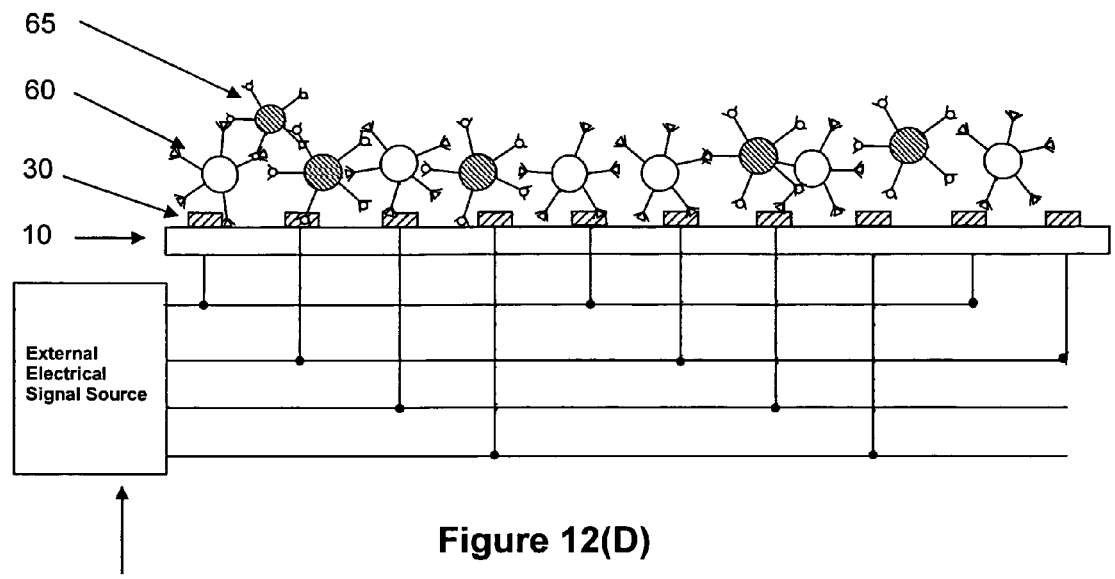
Figure 12E:
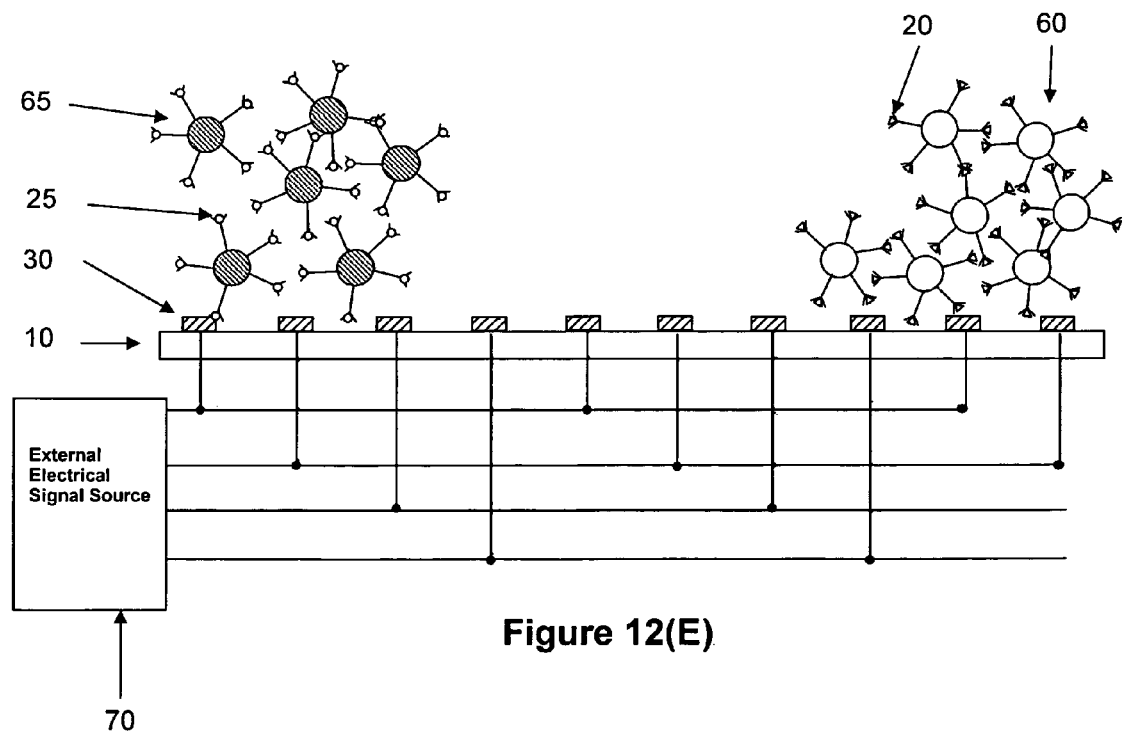

FIG. 10 shows the use of interdigitated, castelled electrode array 250 for manipulating molecule-microparticle complexes. FIG. 10(A) shows that molecule-microparticle complexes 60 are directed into and trapped at the edges of the electrode elements 250 when molecule-microparticles experience positive dielectrophoresis under appropriate electrical signals from signal source 70. FIG. 10(B) shows that molecule-microparticle complexes are directed and aggregated into the bay regions between adjacent electrode tips when they experience negative dielectrophoresis. This electrode array in FIG. 10 is similar to an interdigitated electrode array described in "Positive and negative dielectrophoretic collection of colloidal particles using interdigitated castellated microelectrodes by Pethig et al., in *J. Phys. D: Appl Phys., Volume* 25, 1992, pages 881–888". Thus further application of the interdigitated electrode array in FIG. 10 for manipulation and separation of molecules or molecule-microparticle complexes or microparticles may be found in the article "Positive and negative dielectrophoretic collection of colloidal particles using interdigitated castellated microelectrodes by Pethig et al., in *J. Phys. D: Appl Phys., Volume* 25, 1992, pages 881–888", and "Selective dielectrophoretic confinement of bioparticles in potential energy wells, by Wang et al., in *J. Phys D: Appl Phys. Volume* 26, 1993, pages 1278–1285". Furthermore, electrode arrays depicted in FIGS. 3(A) and 3(B) may also employed for similar types of manipulations.

FIG. 11 shows an example of manipulation and separation of target molecules from a molecule mixture using a biochip that has incorporated a parallel microelectrode array 30 on its surface. The electrode geometry and the fluidic chamber for such manipulation are similar to those described in FIGS. 1 and 2. FIG. 11(A) shows that molecule mixtures including target molecules 20 are placed in a chamber comprising a biochip 10 at a chamber bottom. FIG. 11(B) shows that microparticles 50 are used to couple/link/bind target molecules 20 from a molecule mixture to form molecule-microparticle complexes 60. FIG. 11(C) shows that appropriate electrical signals from a signal source 70 are applied to the electrode elements 30 to attract molecule-microparticle complexes 60 towards the electrode plane and trap them there. After the molecule-microparticle complexes are trapped onto the electrode plane under dielectrophoretic forces exerting on the molecule-microparticle complexes, additional forces such as fluid flow forces are applied so the molecules other than target molecules are removed from the chamber. FIG. 11(D) shows that molecule-microparticle complexes remain on the electrode edges after the unwanted molecules are washed away. FIG. 11(E) shows that target molecules are disassociated from or removed from the microparticles. Through this process, only target molecules are kept in the chamber whilst other molecules are removed. Dependent on the application, microparticles may then be removed or manipulated away from the chamber. The target molecules may then be further used for biochemical reactions.

FIG. 12 shows an example of manipulation and separation of two types of target molecules (e.g., mRNA molecules and certain protein molecules) from a molecule mixture using a biochip that has incorporated a parallel microelectrode array 30 on its surface. The electrode geometry and the fluidic chamber for such manipulation are similar to those described in FIGS. 5 and 2. The electrode structures used here may generate dielectrophoresis forces as well as traveling wave dielectrophoresis forces on particles subjected to the induced electrical field. FIG. 12(A) shows that molecule mixtures including target molecules 20 and 25 are placed in a chamber comprising a biochip 10 at a chamber bottom. FIG. 12(B) shows that two types of microparticles are used to couple/link/bind target molecules 20 from a molecule mixture to form molecule-microparticle complexes 60 and 65. FIG. 12(C) shows that an appropriate electrical signals from a signal source 70 are applied to the electrode elements 30 to attract molecule-microparticle complexes 60 and 65 towards the electrode plane and trap them there. After the molecule-microparticle complexes are trapped onto the electrode plane under dielectrophoretic forces exerting on the molecule-microparticle complexes, additional forces such as fluid flow forces are applied so the molecules other than target molecules are removed from the chamber. FIG. 12(D) shows that molecule-microparticle complexes remain on the electrode edges after the unwanted molecules are washed away and after the additional forces that have removed the molecules other than the target molecules have stopped. FIG. 12(E) shows that the two types of target molecule-microparticle complexes are separated by traveling-wave-dielectrophoresis forces that drive the two types of complexes to different directions under applied field of a different condition. This different condition may include a different field frequency, a different magnitude and a different signal excitation mode that allows for the generation of a traveling wave electrical field. Through this process, only the two types of target molecules are kept in the chamber whilst other molecules are removed, and furthermore, the two types of molecules are separated on electrode structures. Dependent on the application, microparticles may then be removed or manipulated away from the chamber. The target molecules may then be further used for biochemical reactions. For the example shown in FIG. 12 to work, the dielectric properties of two types of microparticles should be chosen appropriately so that under the first applied field condition both particles exhibit positive dielectrophoresis as shown in FIG. 12C and under the second field condition the two types of particles exhibit traveling-wave-dielectrophoresis that drive them in opposite directions. Those who are skilled in dielectrophoresis and traveling-wave dielectrophoresis may readily determine what properties the particles should possess in terms of size, composition and geometry in order for them to behave properly in this example. Furthermore, those skilled in dielectrophoresis and traveling-wave dielectrophoresis may use a different dielectrophoresis manipulation method to achieve similar effects to those shown in FIG. 12—isolating two types of target molecules from a molecule mixture.

FIGS. 13A–13C show an example of manipulating two types of target molecules from a molecule mixture simultaneously using a fluidic chamber similar to that shown in FIG. 2. The chamber consists of an interdigitated electrode array 250 on the chamber bottom. FIG. 13A illustrates the top view of the electrode system 250 for the situation after a molecule mixture is introduced. The molecule mixture comprises two types of target molecules 300 and 310, other molecules 320, and two types of binding partners 330 and 340. The binding partners in this case are microparticles that can be manipulated by dielectrophoresis forces. The molecule mixture may be a cell lysate and the target molecules may be mRNA molecules and certain protein molecules. FIG. 13 B shows that the target molecules have bound to their corresponding binding partners to from molecule-binding partner complexes 350 and 360. FIG. 13 C shows that under appropriately applied electrical signals from signal source 70, the molecule-binding partner complexes have been selectively manipulated and separated onto strong and weak field regions of the electrode system. In this case, the binding partners 330 and 340 should be chosen to ensure that they have appropriate dielectric properties. At the applied field frequency, the binding partner 340 is more electrically polarizable (large conductivity and/or permittivity) than the surrounding medium and exhibits positive dielectrophoresis. The binding partner 330 is less electrically-polarizable (small electrical conductivity and/or permittivity) than the surrounding medium, and exhibits negative dielectrophoresis. Those who are skilled in the area of dielectrophoresis manipulation and dielectric characterization of materials may readily choose appropriate binding partners in terms of their size, shape, structure and composition. Such a manipulation step can be used to detect the target molecules, and is particular useful for the situations where the concentration of the target molecules is low and difficult to measure or quantify. By coupling the target molecules onto the surfaces of the binding partners and concentrating the molecule-binding partner complexes on certain locations within the chamber, the identification and quantification of the target molecules are made easier. For example, if the target molecules are pre-labeled with fluorescent molecules, fluorescent detection may be used in the regions to which the molecule-binding partner complexes have been manipulated. Furthermore, the example in FIG. 13 shows that two types of target molecules may be manipulated and analyzed simultaneously.

FIG. 14 shows an example of manipulating two types of target molecules from a molecule mixture simultaneously using a fluidic chamber similar to that shown in FIG. 2. The chamber consists of a spiral electrode array 210 on the chamber bottom. FIG. 14A illustrates the top view of the electrode system for the situation after a molecule mixture is introduced. The molecule mixture comprises two types of target molecules 330 and 310, other molecules 320, and two types of binding partners 330 and 340. The binding partners in this case are microparticles that can be manipulated by dielectrophoresis and traveling-wave dielectrophoresis forces. The molecule mixture may be a cell lysate and the target molecules may be DNA molecules and certain protein molecules. FIG. 14 B shows that the target molecules have bound to their corresponding binding partners to from molecule-binding partner complexes 350 and 360. FIG. 14 C shows that under appropriately applied electrical field conditions, traveling-wave dielectric field is produced in the chamber and under the influence of the field, one type of the molecule-binding partner complexes 350 has been moved towards the center of the spiral electrode array and the other type 360 has been moved towards the peripheral region of the electrode array. In this case, the binding partners 330 and 340 should be chosen to ensure that they have appropriate dielectric properties. Those who are skilled in the area of dielectrophoresis and traveling-wave dielectrophoresis manipulation and dielectric characterization of materials may readily choose appropriate binding partners in terms of their size, shape, structure and composition. The governing equation for such a choice is the traveling-wave force equation and the factor $\zeta_{TWD}=\mathrm{Im}(\epsilon_p^*-\epsilon_m^*/(\epsilon_p^*+2\epsilon_m^*))$ described in Section F. Similar to the example in FIG. 13, such a manipulation step can be used to detect the target molecules, and is particular useful for the situations where the concentration of the target molecules is low and difficult to measure or quantify.

FIGS. 15A–15B show an example of manipulating a molecule mixture in an acoustic fluidic chamber similar to that shown in FIG. 4. The chamber comprises a piezoelectric element 140 on the chamber bottom, a spacer and a top plate 160 (see FIG. 4). FIG. 15A shows the cross-sectional view of the acoustic chamber for the situation after a molecule mixture is introduced. Here, the two types of the target molecules 300 and 310 have been coupled onto the surfaces of their corresponding binding partners to form molecule-binding partner complexes 350 and 360. FIG. 15B shows that when electrical signals from signal source 70 are applied to the piezoelectric elements 140 on the chamber bottom, acoustic wave is generated on the element and transmitted into the fluid chamber. A standing wave will be generated inside the chamber after the acoustic wave is reflected from the top plate. Under such a standing wave, binding partners experience acoustic radiation forces so that the molecule-binding partner complexes move to certain locations within the standing wave. The two types of molecule-binding partner complexes 350 and 360 are moved to different heights within the chamber. The positions to which the molecule-binding partner complexes settle correspond to the locations where the acoustic radiation force and the gravitational force acting on the complexes balance to each other. The acoustic radiation force depends on the acoustic properties of the binding partners (see the acoustic force equation in Section F). The gravitation forces depend on the size and relative specific density of the binding partner with respect to the surrounding medium. Thus, by choosing the binding partners with different properties, e.g., specific density, acoustic impedance, size), their corresponding molecules may be selectively manipulated in the acoustic chamber.

The above examples are included for illustrative purposes only and is not intended to limit the scope of the invention. Since modifications will be apparent to those of skill in this art, it is intended that this invention be limited only by the scope of the appended claims.

The invention claimed is:

1. A method for manipulating a moiety in a microfluidic application, which method comprises:
   a) coupling a moiety to be manipulated onto a surface of a binding partner of said moiety to form a moiety-binding partner complex; and
   b) manipulating said moiety-binding partner complex with a physical force in a microfluidic application chip format, wherein said manipulation is effected through a combination of a signal source that is external to said chip and a structure that is built into or on said chip, thereby said moiety is manipulated, and wherein said moiety is not directly manipulatable by an acoustic force and the moiety-binding partner complex is manipulated by an acoustic force.

2. The method of claim 1, wherein the moiety to be manipulated is selected from the group consisting of a cell, a cellular organelle, a virus, a molecule and an aggregate or complex thereof.

3. The method of claim 2, wherein the cell is selected from the group consisting of an animal cell a plant cell, a fungus cell, a bacterium cell and a recombinant cell.

4. The method of claim 2, wherein the cellular organelle is selected from the group consisting of a nuclei, a mitochondrion, a chloroplast, a ribosome, an ER, a Golgi apparatus, a lysosome, a proteasome, a secretory vesicle, a vacuole and a microsome.

5. The method of claim 2, wherein the molecule is selected from the group consisting of an inorganic molecule, an organic molecule and a complex thereof.

6. The method of claim 5, wherein the inorganic molecule is an ion selected from the group consisting of a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron and an arsenic ion.

7. The method of claim 5, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

8. The method of claim 1, wherein the binding partner is a microparticle.

9. The method of claim 8, wherein the dimension of the microparticle is from about 0.01 micron to about several thousand microns.

10. The method of claim 8, wherein the microparticle is selected from the group consisting of a plastic particle, a polystyrene microbead, a glass bead, a magnetic bead, a hollow glass sphere, a metal particle, a particle of complex composition, and a microfabricated free-standing microstructure.

11. The method of claim 1, wherein the moiety is coupled to the surface of the binding partner directly or via a linker.

12. The method of claim 11, wherein the linker is a cleavable linker, and upon cleavage, the moiety is cleaved from the binding partner.

13. The method of claim 1, wherein the moiety is coupled to the surface of the binding partner via a covalent or a non-covalent linkage.

14. The method of claim 13, wherein the linkage between the moiety and the surface of the binding partner is effected via a specific or a non-specific binding.

15. The method of claim 13, wherein the linkage between the moiety and the surface of the binding partner is a cleavable linkage.

16. The method of claim 15, wherein the linkage is cleavable by a chemical, physical or an enzymatic treatment.

17. The method of claim 1, wherein the acoustic force is effected via a standing-wave acoustic field or a traveling-wave acoustic field.

18. The method of claim 1, wherein the acoustic force is effected via an acoustic field produced by piezoelectric material.

19. The method of claim 1, wherein the chip is selected from the group consisting of a silicon dioxide, a silicon nitride, a plastic, a glass, a ceramic, a photoresist and a rubber chip.

20. The method of claim 1, wherein the manipulation is selected from the group consisting of transportation, focusing, enrichment, concentration, aggregation, trapping, repulsion, levitation, separation, fractionation, isolation and linear or other directed motion of the moiety.

21. The method of claim 1, further comprising a step of decoupling the moiety from the surface of the binding partner after the moiety is manipulated.

22. The method of claim 1, wherein the moiety is a DNA, the binding partner is a porous bead and the DNA is reversibly absorbed onto the surface of the porous bead in a buffer containing high salt concentration.

23. The method of claim 1, wherein the moiety is a mRNA and the mRNA specifically binds to the surface of a binding partner that is modified to contain oligo-dT polynucleotide.

24. The method of claim 1, wherein the moiety is a protein and the protein non-specifically binds to the surface of a binding partner that is modified with a detergent.

25. The method of claim 24, wherein the detergent is SDS.

26. The method of claim 1, wherein the moiety is not directly manipulatable by a dielectrophoresis force and the moiety-binding partner complex is manipulated by a dielectrophoresis force.

27. The method of claim 1, wherein the moiety is not directly manipulatable by a traveling-wave dielectrophoresis force and the moiety-binding partner complex is manipulated by a traveling-wave dielectrophoresis force.

28. The method of claim 1, wherein the moiety is not directly manipulatable by an electrostatic force and the moiety-binding partner complex is manipulated by an electrostatic force.

29. The method of claim 1, wherein the moiety is not directly manipulatable by an optical radiation force and the moiety-binding partner complex is manipulated by an optical radiation force.

30. The method of claim 1, wherein at least 5% of the moiety to be manipulated is coupled onto surface of the binding partner.

31. The method of claim 1, wherein at least 90% of the moiety to be manipulated is coupled onto surface of the binding partner.

32. The method of claim 1, wherein a plurality of moieties is manipulated.

33. The method of claim 32, wherein the plurality of moieties is manipulated via a plurality of corresponding binding partners.

34. The method of claim 32, wherein the plurality of moieties is manipulated sequentially or simultaneously.

35. The method of claim 1, further comprising manipulating said moiety-binding partner complex by a physical force selected from the group consisting of a dielectrophoresis, a traveling-wave dielectrophoresis, a magnetic, an electrostatic, a mechanical, an optical radiation force and a thermal convection force.

36. The method of claim 35, wherein the dielectrophoresis force or the traveling wave dielectrophoresis is effected via electrical fields produced by electrodes.

37. The method of claim 35, wherein the magnetic force is effected via a magnetic field produced by a ferromagnetic material.

38. The method of claim 35, wherein the magnetic force is effected via a magnetic field produced by a microelectromagnetic unit.

39. The method of claim 35, wherein the electrostatic force is effected via a direct current (DC) electric field.

40. The method of claim 35, wherein the mechanical force is a fluidic flow force.

41. The method of claim 35, wherein the optical radiation force is effected via a laser tweezers.

42. The method of claim 1, wherein the moiety is a DNA and the DNA specifically binds to the surface of a binding partner via sequence specific hybridization or binding to an anti-DNA antibody.

43. The method of claim 1, wherein the moiety is a protein and the protein specifically binds to the surface of a binding partner that is modified with an antibody that specifically recognizes the protein.

44. The method of claim 1, wherein the moiety is not directly manipulatable by a magnetic force.

45. A kit for manipulating a moiety in a microfluidic application, which kit comprises:

a) a binding partner onto the surface of which a moiety to be manipulated can be coupled to form a moiety-binding partner complex;

b) means for coupling said moiety onto the surface of said binding partner; and c) a chip on which said moiety-binding partner complex can be manipulated with a physical force that is effected through a combination of a signal source that is external to said chip and a structure that is built into or on said chip, and wherein said moiety is not directly manipulatable by an acoustic force and the moiety-binding partner complex is manipulated by an acoustic force.

46. The kit of claim 45, further comprising instruction(s) for coupling the moiety onto the surface of the binding partner and/or manipulating the moiety-binding partner complex on the chip.

* * * * *